US010660899B2

(12) United States Patent
Schultz et al.

(10) Patent No.: US 10,660,899 B2
(45) Date of Patent: May 26, 2020

(54) DIRECTED DIFFERENTIATION OF OLIGODENDROCYTE PRECURSOR CELLS TO A MYELINATING CELL FATE

(71) Applicants: The Scripps Research Institute, La Jolla, CA (US); Novartis AG, Basel (CH)

(72) Inventors: Peter Schultz, La Jolla, CA (US); Luke Lairson, San Diego, CA (US); Vishal Deshmukh, La Jolla, CA (US); Costas Lyssiotis, Boston, MA (US)

(73) Assignees: The Scripps Research Institute, La Jolla, CA (US); Novartis AG, Basel (CH)

( * ) Notice: Subject to any disclaimer, the term of this patent is extended or adjusted under 35 U.S.C. 154(b) by 0 days.

(21) Appl. No.: 14/973,105

(22) Filed: Dec. 17, 2015

(65) Prior Publication Data

US 2016/0166687 A1   Jun. 16, 2016

Related U.S. Application Data

(62) Division of application No. 13/985,342, filed as application No. PCT/US2012/025712 on Feb. 17, 2012, now Pat. No. 9,592,288.

(Continued)

(51) Int. Cl.
*A61K 31/13* (2006.01)
*A61K 31/44* (2006.01)
(Continued)

(52) U.S. Cl.
CPC ........ *A61K 31/5415* (2013.01); *A61K 31/135* (2013.01); *A61K 31/137* (2013.01);
(Continued)

(58) Field of Classification Search
CPC ....... A61K 31/46; A61K 31/40; A61K 31/137
(Continued)

(56) References Cited

U.S. PATENT DOCUMENTS 7,301,071 B2   11/2007   Zheng
9,592,288 B2   3/2017   Schultz et al.
(Continued)

FOREIGN PATENT DOCUMENTS

JP   10-218867   8/1998
JP   2008-518896   5/2008
(Continued)

OTHER PUBLICATIONS

Almeida et al. "Methylphenidate-induced Akathisia in a Patient with Multiple Sclerosis", Prim Care Companion J Clin Psychiatry, 2006, vol. 8(6), pp. 379-380.*
(Continued)

*Primary Examiner* — Shengjun Wang
(74) *Attorney, Agent, or Firm* — Kilpatrick Townsend & Stockton LLP

(57) ABSTRACT

The present invention provides methods of inducing differentiation of oligodendrocyte progenitor cells to a mature myelinating cell fate with a neurotransmitter receptor modulating agent. The present invention also provides methods of stimulating increased myelination in a subject in need thereof by administering said neurotransmitter receptor modulating agent. Methods of treating a subject having a demyelinating disease using a neurotransmitter receptor modulating agent are also provided.

9 Claims, 52 Drawing Sheets

Related U.S. Application Data

(60) Provisional application No. 61/444,666, filed on Feb. 18, 2011.

(51) Int. Cl.

| | |
|---|---|
| A61K 31/40 | (2006.01) |
| A61K 31/5415 | (2006.01) |
| A61K 31/439 | (2006.01) |
| A61K 31/138 | (2006.01) |
| A61K 31/135 | (2006.01) |
| A61K 31/137 | (2006.01) |
| A61K 38/21 | (2006.01) |
| A61K 39/395 | (2006.01) |
| A61K 31/216 | (2006.01) |
| A61K 31/46 | (2006.01) |
| A61K 31/495 | (2006.01) |

(52) U.S. Cl.
CPC .......... *A61K 31/138* (2013.01); *A61K 31/216* (2013.01); *A61K 31/40* (2013.01); *A61K 31/439* (2013.01); *A61K 31/46* (2013.01); *A61K 31/495* (2013.01); *A61K 38/215* (2013.01); *A61K 39/3955* (2013.01)

(58) Field of Classification Search
USPC ........................................ 514/304, 428, 653
See application file for complete search history.

(56) References Cited

U.S. PATENT DOCUMENTS

| | | | |
|---|---|---|---|
| 2003/0225072 | A1 | 12/2003 | Welsh et al. |
| 2006/0258735 | A1 | 11/2006 | Meng et al. |
| 2009/0155207 | A1 | 6/2009 | Hariri et al. |
| 2010/0189698 | A1 | 7/2010 | Willis |
| 2012/0264719 | A1* | 10/2012 | Boulton ............... A61K 31/137 514/114 |
| 2014/0038949 | A1 | 2/2014 | Schultz et al. |
| 2017/0136029 | A1 | 5/2017 | Schultz et al. |

FOREIGN PATENT DOCUMENTS

| | | |
|---|---|---|
| JP | 2010-533656 A | 10/2010 |
| WO | 2008/143913 A1 | 11/2008 |
| WO | 2009/068668 | 6/2009 |
| WO | 2009/153291 | 12/2009 |
| WO | 2010075239 A1 | 7/2010 |

OTHER PUBLICATIONS

PCT/US2012/25712, "International Search Report and Written Opinion", dated May 30, 2012, 15 pages.

Mendes et al., "Classical immunomodulatory therapy in multiple sclerosis: how it acts, how it works", Arq Neuropsiquiatr., vol. 69, No. 3, Jun. 2011, pp. 536-543.

Stevens, et al., "Adenosine: A Neuron Glial Transmitter Promoting Myelination in the CNS in Response to Action Potentials", Neuron, vol. 36(5), Dec. 5, 2002, 855-868.

Butt et al., "Neurotransmitter-Mediated Calcium Signalling in Oligodendrocyte Physiology and Pathology," Sep. 2006, Wiley InterScience , pp. 665-675.

Magnaghi et al., "Novel Pharmacological Approaches To Schwann cells As Neuroprotective Agents For Peripheral Nerve Regeneration", International Review Of Neurobiology, 2009, vol. 07, pp. 295-312, DOI: 10.1016.

Bangham et al., HTLV-1-associated myelopathy/tropical spastic paraparesis. Nature Reviews, Article No. 15012, Published online: doi:10_1038/nrpd.2015.12, 16 pages, Jun. 18, 2015.

Guerreiro et al., Levels of serum chemokines discriminate clinical myelopathy associated with human T lymphotropic virus type 1 (HTLV-1)/tropical spastic paraparesis (HAM/TSP) disease from HTLV-1 carrier state. Clinical and Experimental Immunology, 145:296-301, 2006.

Linker and Lee, Models of autoimmune demyelination in the central nervous system: on the way to translational medicine. Experimental & Translational Stroke Medicine, 1(5):10 pages, 2009.

Mayo et al., The Innate immune system in demyelinating disease. Immunol Review, 248(1):170-187, 2012.

Merrill, *In Vitro* and *In Vivo* pharmacological models to access demyelination and remyelination. Neuropsychopharmacology Reviews, 34:55-73, 2009.

Rangachari and Kuchroo, Using EAE to better understand principles of immune function and autoimmune pathology. J.Autoimmun., 45:31-39, 2013.

Reeves and Swenson, *Disorders of the Nervous System*. Chapter 23, "Demyelinating diseases of the nervous system." reprinted from the Internet: https://www.dartmouth.edu/~dons/part3/chapter_23.html Apr. 27, 2016, 7 pages.

Spalice et al., Clinical and pharmacological aspects of inflammatory demyelinating diseases in childhood: An update. Current Neuropharmacology, 8:135-148, 2010.

Steinman, Assessment of animal models for MS and demyelinating disease in the design of rational therapy. Neuron, 24:511-514, 1999.

Swanborg, Short Analytical Review. Animal models of human disease. Experimental Autoimmune encephalomyelitis in rodents as a model for human demyelinating disease. Clinical Immunology and Immunopathology, 77(1):4-13, 1995.

Deshmukh et al., "A regenerative approach to the treatment of multiple sclerosis," Nature, Oct. 2013, vol. 502(7471), pp. 327-332, DOI: 10.1038/nature12647.

Stangel et al., "Remyelination Strategies: New Advancements Toward a Regenerative Treatment in Multiple Sclerosis," Current Neurology and Neuroscience Reports, May 2006, vol. 6(3), pp. 229-235.

EP Patent Application No. 12 74 7134, Supplementary Search Report, dated Jun. 18, 2014, 3 pages.

Chang et al., "Premyelinating Oligodendrocytes in Chronic Lesions of Multple Sclerosis," N Engl J Med, 2002, vol. 346, 165.

Chari et al.,"Efficient Recolonisation of Progenitor-Depleted Areas of the CNS by Adult Oligodendrocyte Progenitor Cells," Glia, 2002, 37: 307-313.

Chari et al., "Dysfunctional Oligodendrocyte Progenitor Cell (OPC) Populations May Inhibit Repopulation of OPC Depleted Tissue," J. Neurosci Res, 2003, 73: 787-793.

Chong et al., "Tapping into the glial reservoir: cells committed to remaining uncommitted," J Cell Biol 2010, 188(3), pp. 305-312.

De Angelis et al., "Muscarinic Receptor Subtypes as Potential Targets to Modulate Oligodendrocyte Progenitor Survival, Proliferation, and Differentiation," Dev Neurobiol, 2012, 72: 713-728.

Gobert et al., "Convergent functional genomics of oligodendrocyte differentiation identifies multiple autoinhibitory signaling circuits," Molecular and Cellular Biology, 2009, 29:1538.

Joubert et al., "Chemical inducers and transcriptional markers of oligodendrocyte differentiation," Journal of Neuroscience Research, 2010, 88: 2546-2557.

Kremer et al., "The Complex World of Oligodendroglial Differentiation Inhibitors," Ann Neurol, 2011, 69: 602-618.

Kuhlmann et al., "Differentiation block of oligodendroglia progenitor cells as a cause for remyelination failure in chronic multiple sclerosis," Brain, 2008, 131, 1749-1758.

Patel et al., "Mediators of oligodendrocyte differentiation during remyelination," FEBS Lett, 2011, 585, 3730-3737.

Wolswijk, "Chronic Stage Multiple Sclerosis Lesions Contain a Relatively Quiescent Population of Oligodendrocyte Precursor Cells," J. Neurosci, 1998, 18(2), pp. 601-609.

Khoury et al., "A Randomized Controlled Double-Masked Trial of Albuterol Add-on Therapy in Patients With Multiple Sclerosis," Arch Neurol. 2010;67(9):1055-1061.

Walgaard et al. "Emerging drugs for Guillain-Barre syndrome" Expert Opinion of Emerging Drugs, Feb. 25, 2011, vol. 16, issue 1, pp. 105-120.

Collongues et al. "Current and future treatment approaches for neuromyelitis optica" Therapeutic Advances in Neurological Disorders, 2011, vol. 4, issue 2, pp. 111-121.

(56) References Cited

OTHER PUBLICATIONS

Oh et al. "Treatment of HTLV-1-Associated Myelopathy/Tropical Spastic Paraparesis: Towards Rational Targeted Therapy," Neurol Clin., 2008, vol. 26, issue 3, pp. 781-796 (printed as 1-15).

Alexander et al. "Acute disseminating encephalomyeitis: Treatment guidelines" Ann Indian Acad Neurol, 2011, vol. 14, suppl1, S60-S64 (printed as pp. 1-12).

The TMA, "Animal Models to Study NMO and TM", Nov. 23, 2015, https://myelitis.org/animal-models-to-study-nmo-andtm/, printed Jul. 14, 2016, pp. 1-7.

Tian et al. "Neuropathic Pain in Animal Models of Nervous System Autoimmune Diseases" Mediators of Inflammation, 2013, pp. 1-13.

Kraker et al. "Autoimmune Neuromuscular Disorder", Current Neuropharmacology, 2011, vol. 9, pp. 400-408.

Lehmann et al. "Pathogenesisi and treatment of immune-mediated neuropathies" Therapeutic Advances in Neurological Disorders, 2009, vol. 2, issue 4, pp. 261-281.

Ragheb et al., "Pharmacological and functional characterization of muscarinic receptor subtypes in developing oligodendrocytes," Journal of Neurochemistry, 2001, vol. 77, pp. 1396-1406.

Smith et al., "Recent developments in drug therapy for multiple sclerosis," Multiple Sclerosis, 1999, vol. 5, 110-120.

Nakano et al., "Antagonizing dopamine D1-like receptor inhibits Th17 cell differentiation: Preventive and therapeutic effects on experimental autoimmune encephalomyelitis," Biochemical and Biophysical Research Communications, 2008, vol. 373, pp. 286-291.

Waggoner et al., "Presynaptic Regulation of Tyrosine Hydroxylase Activity in Rat Striatal Synaptosomes by Dopamine Analogs," Molecular Pharmacology, 1980, vol. 18, pp. 91-99.

Molina-Holgado et al. "Regulation of muscarinic receptor function in developing oligodendrocytes by agonist exposure" British Journal of Pharmacology, 2003, 138, pp. 47-56. (Year: 2003).

Yong et al. "Interferon beta in the treatment of multiple sclerosis mechanisms of action" Neurology, 1998, vol. 51(3), pp. 1-38. (Year: 1998).

Kubo et al. "Antimuscarinic Effects of Antihistamines: Quantitative Evaluation by Receptor-Binding Assay" Japan J. Pharmacol., 1987, vol. 43, pp. 277-282. (Year: 1987).

Cui, et al. "Muscarinic Acetylcholine Receptors Mediate Oligodendrocyte Progenitor Survival Through Src-Like Tyrosine Kinases and P13K/Akt Pathways," Neurochemistry International, vol. 48, Issue 5, Apr. 2006, pp. pp. 383-393.

EP18208362.6, "Extended European Search Report," dated Apr. 26, 2019, 5 pages.

* cited by examiner

*Fig. 1A*
A.
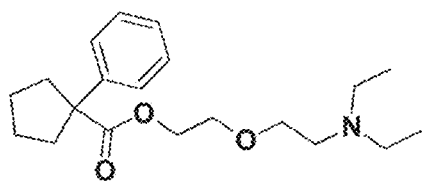
Carbetapentane: EC₅₀= 260 nM
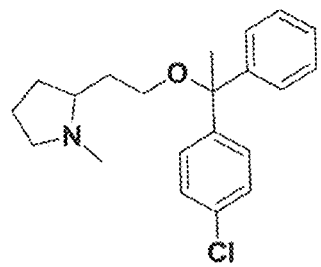
Clemastine: EC₅₀= 780 nM
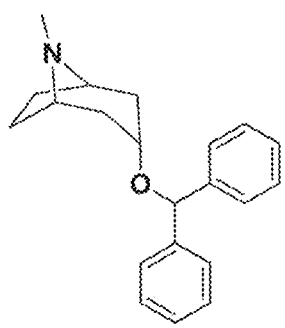
Benztropine: EC₅₀= 250 nM
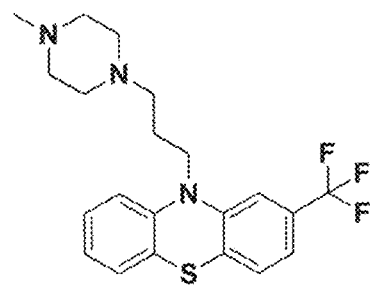
Trifluoperazine: EC₅₀= 30 nM
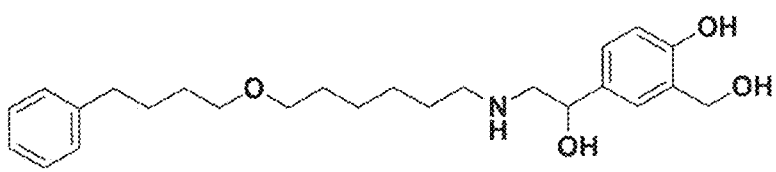
Salmeterol: EC₅₀= 770 nM
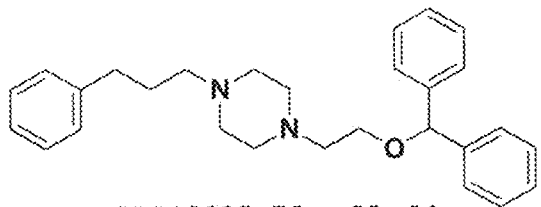
GBR12935: EC₅₀= 80 nM Fig. 1B-C
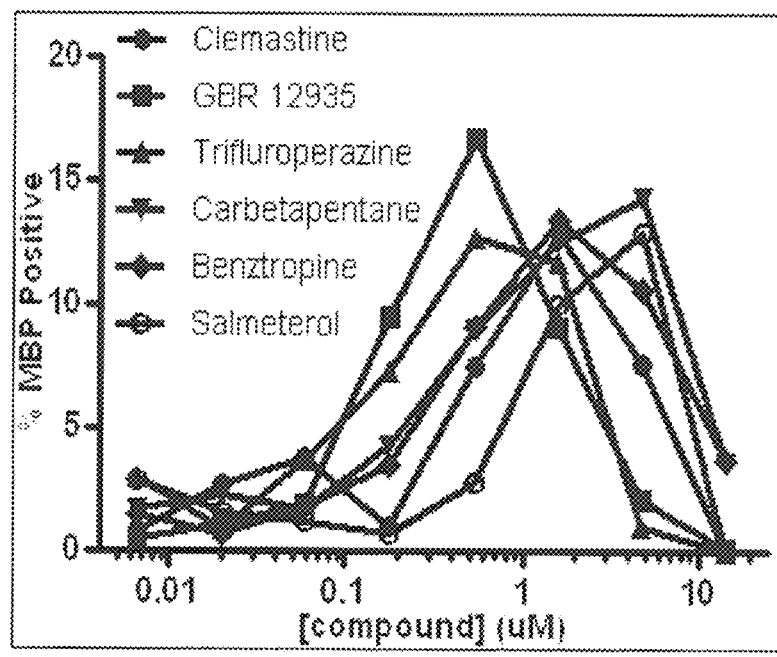
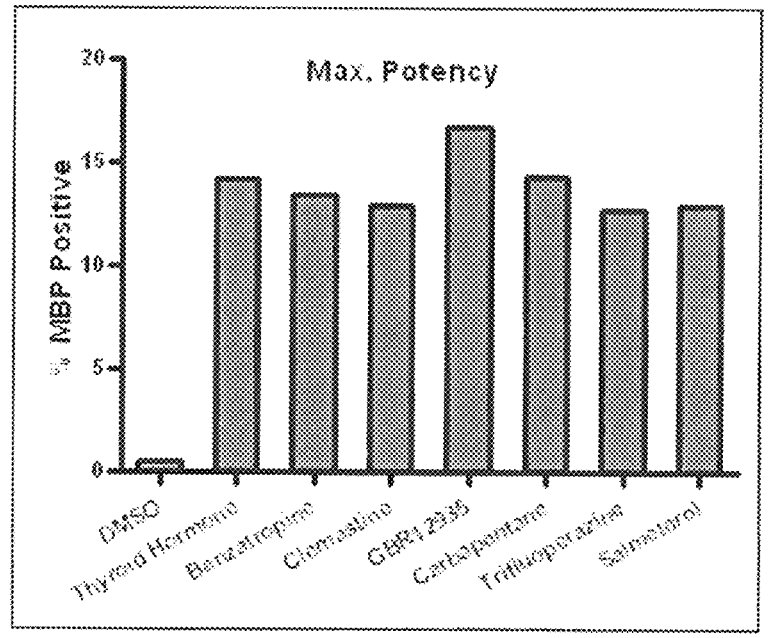

*Fig. 2B-C*
B.
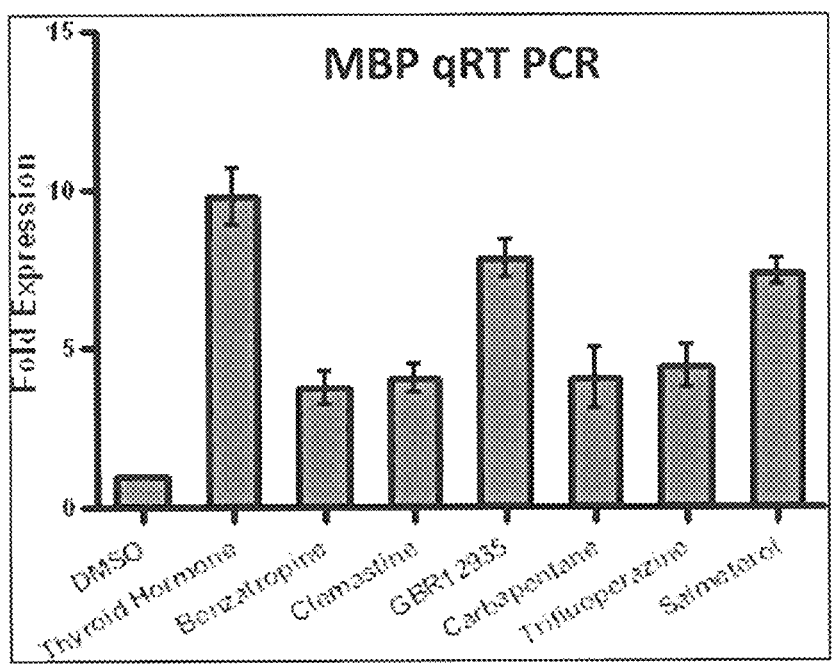
C.
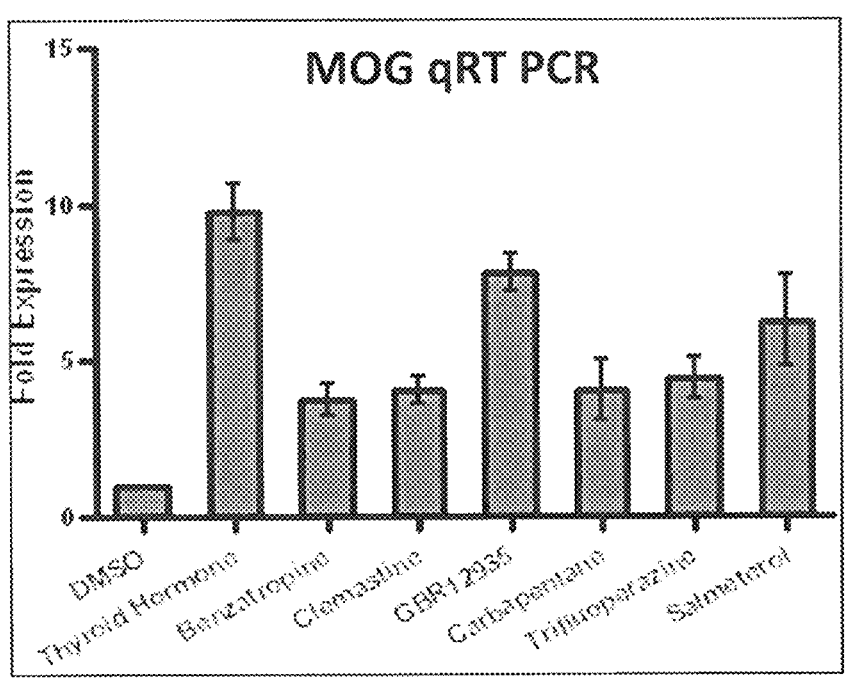

*Fig. 5B-C*
B.
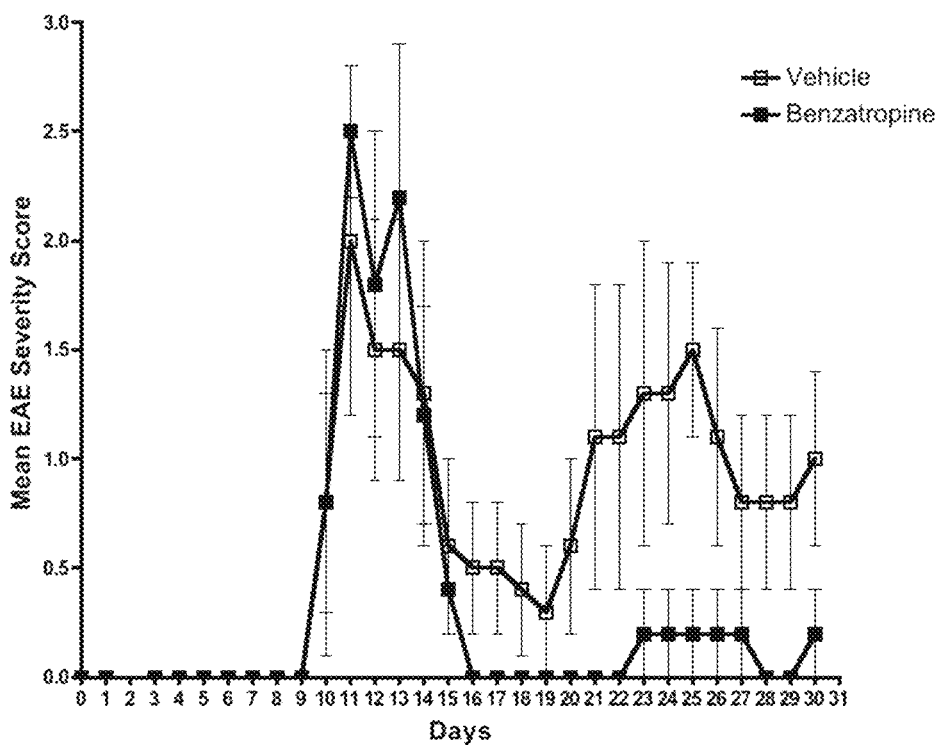
C.
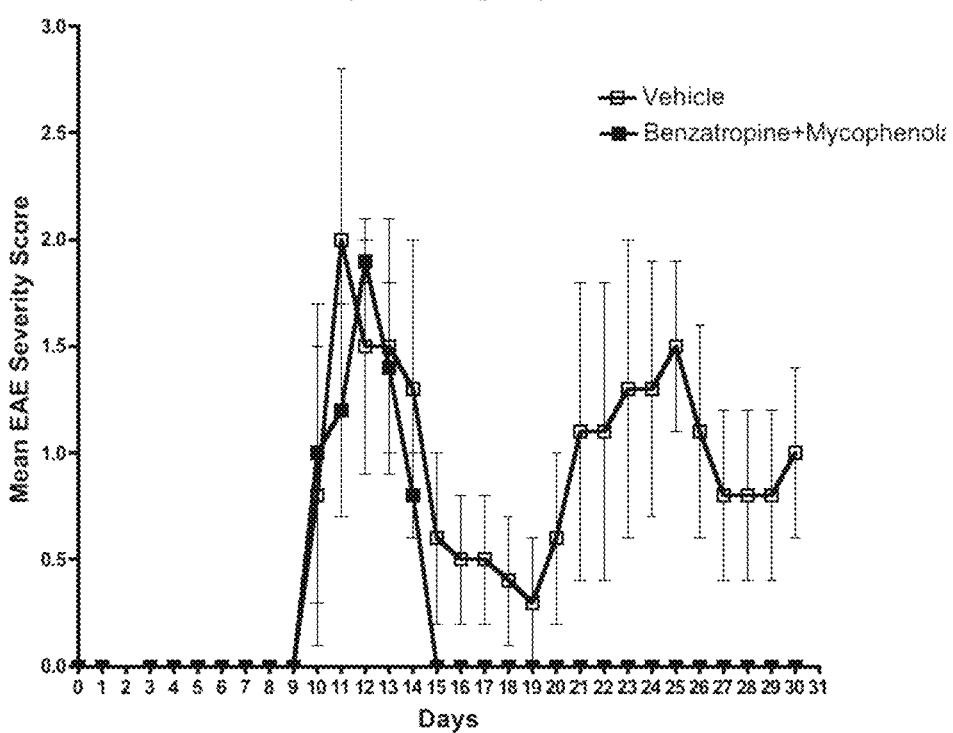

*Fig. 5D-E*
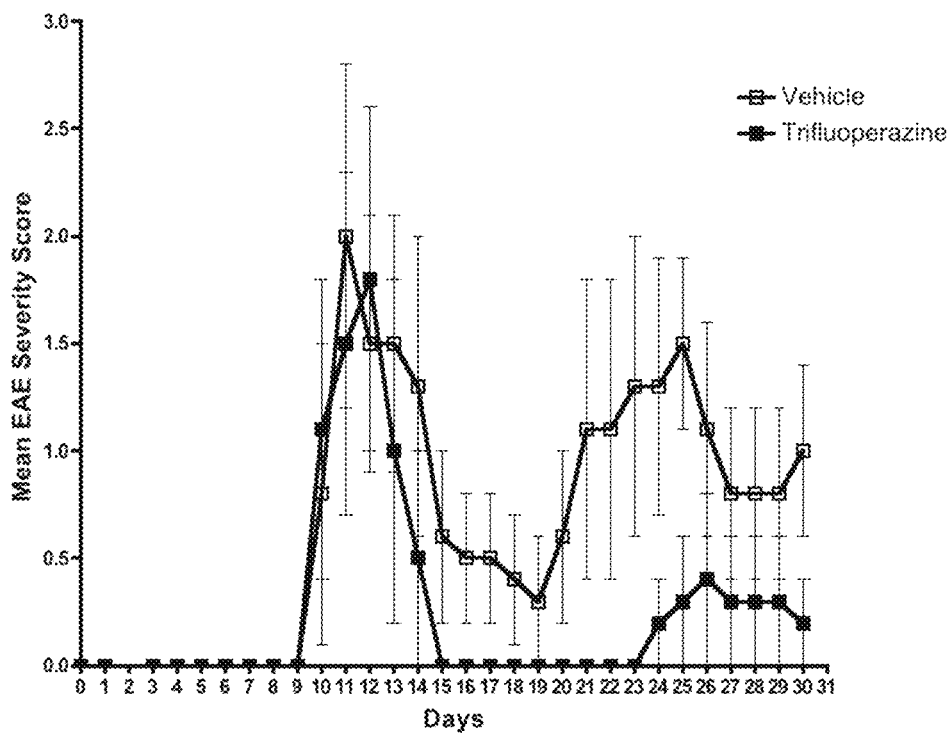
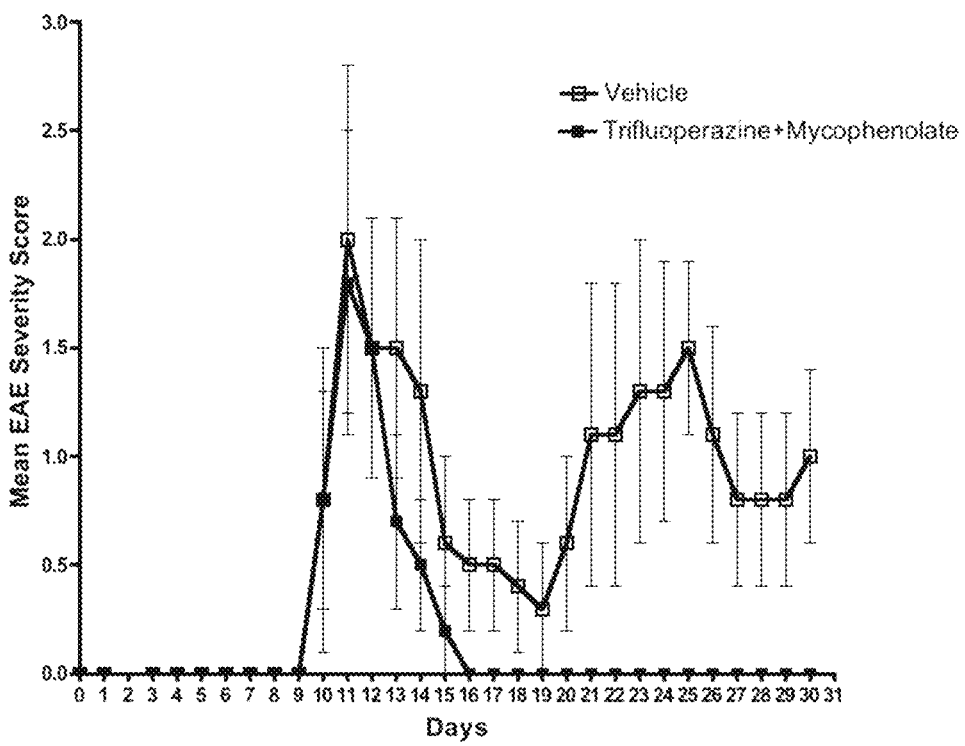

*Fig. 6A-B*
A.
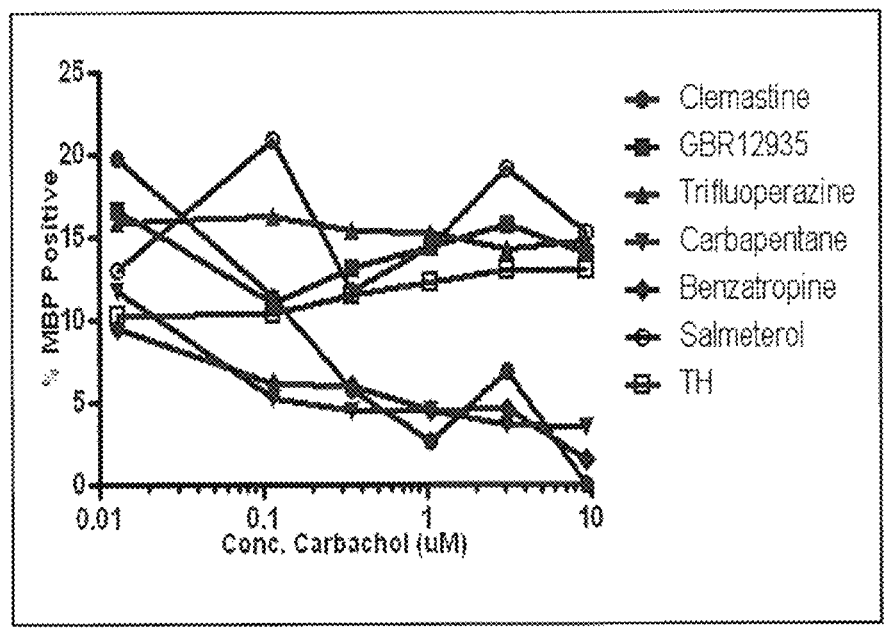
B.
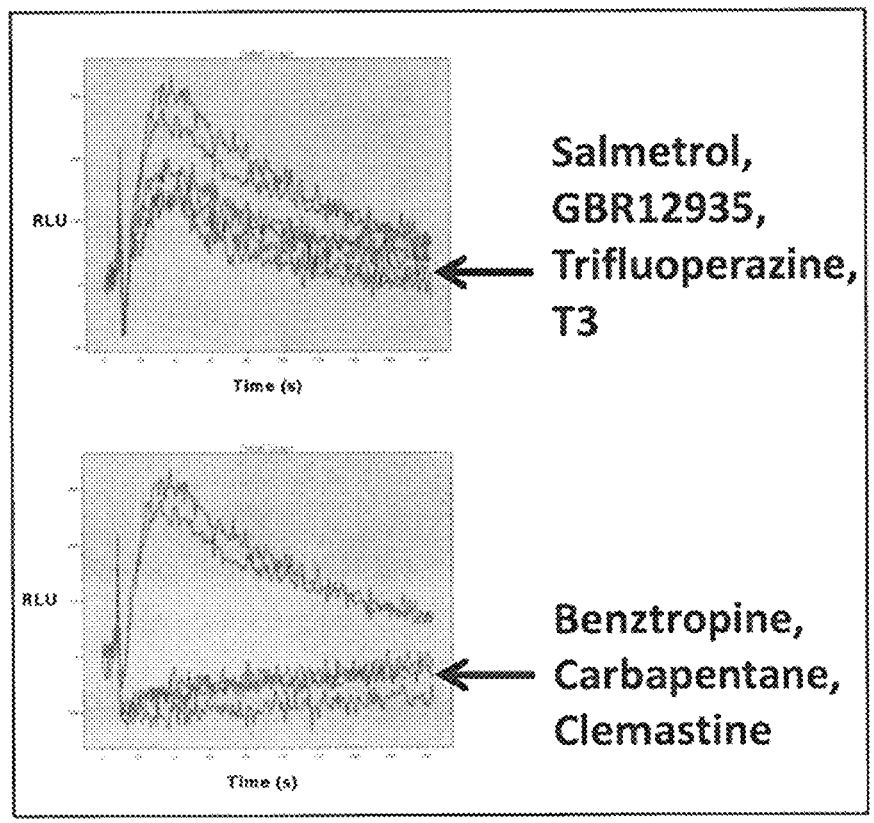

Fig. 7A-C
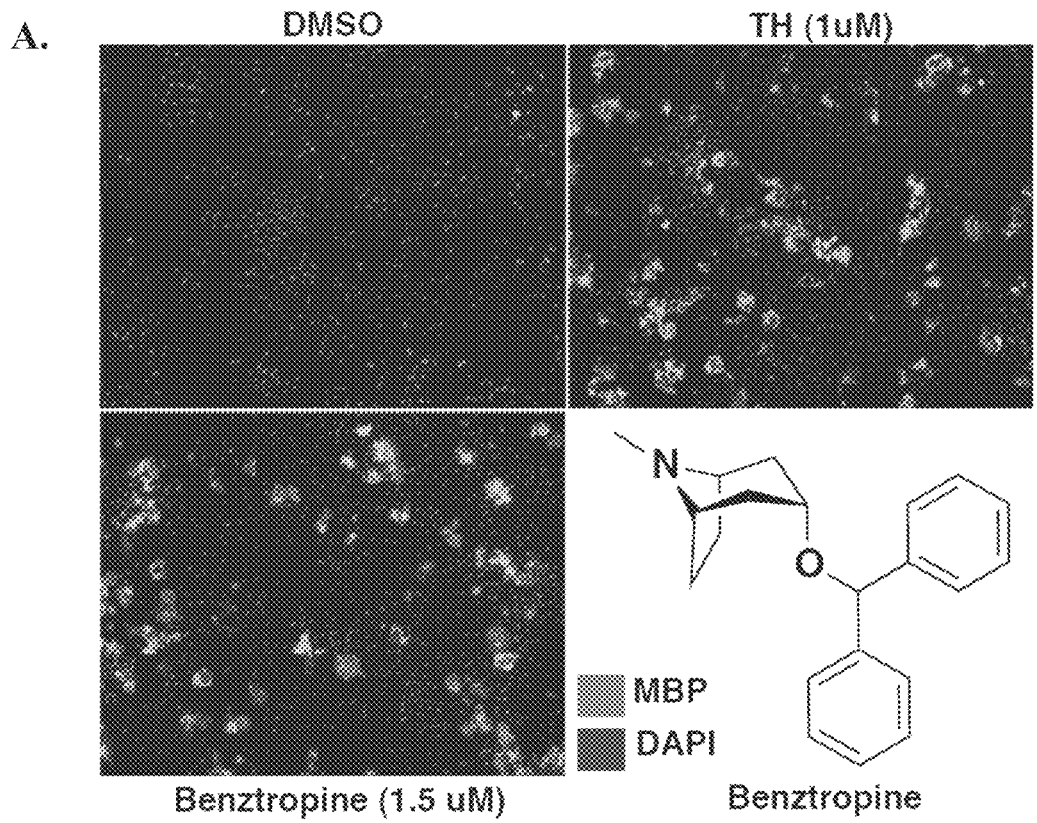
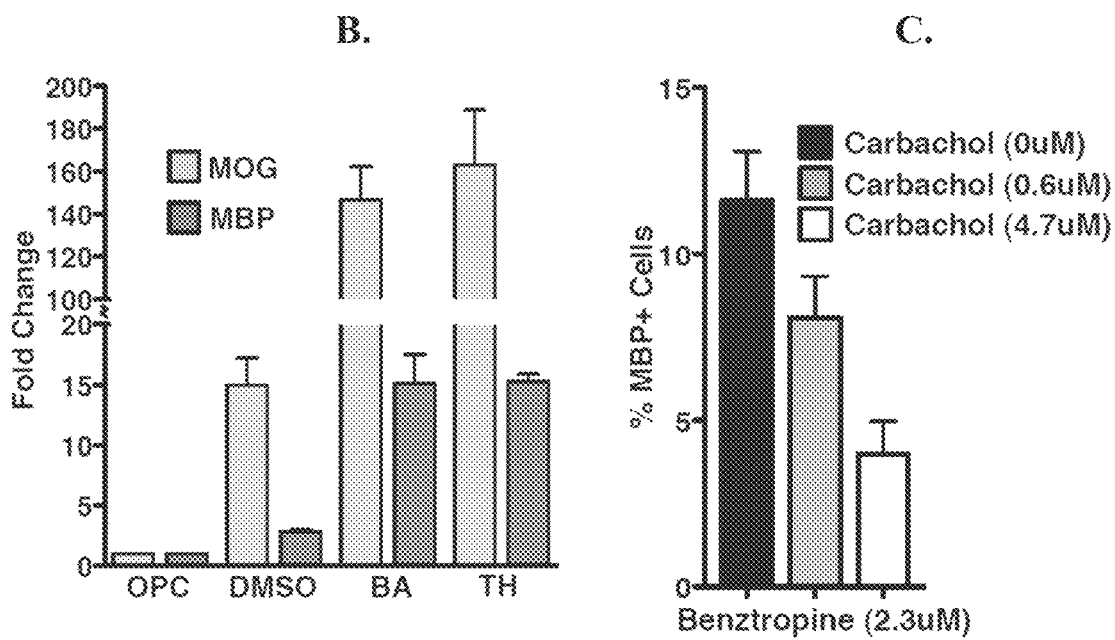

Fig. 8A-B
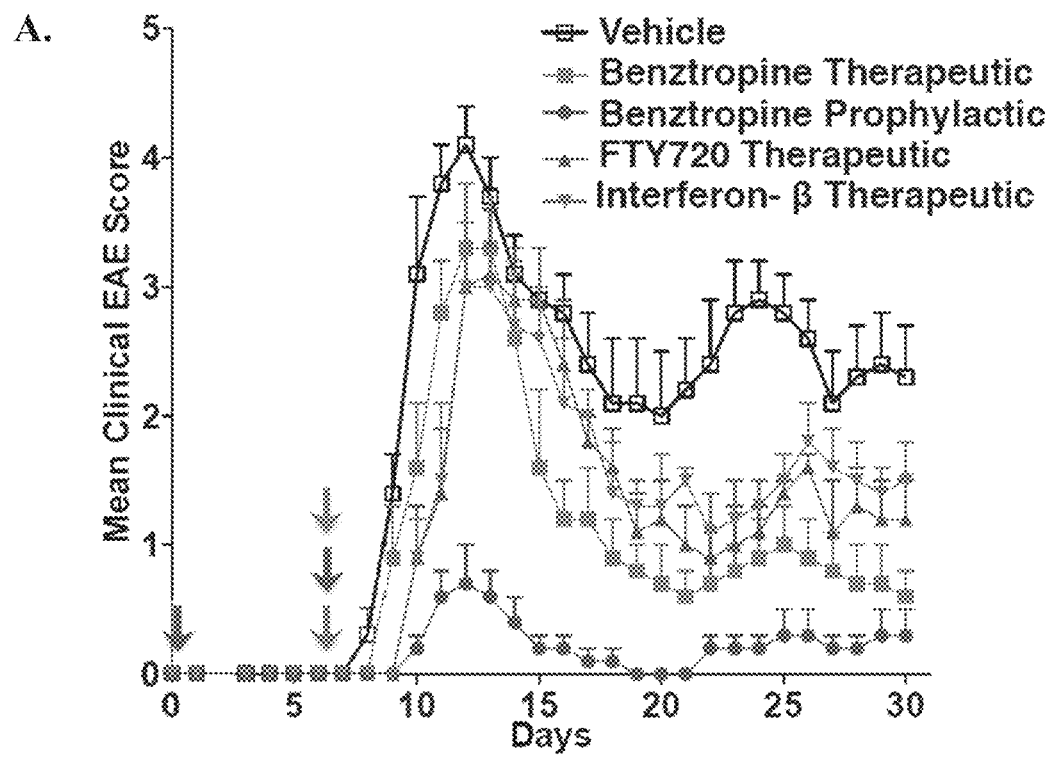
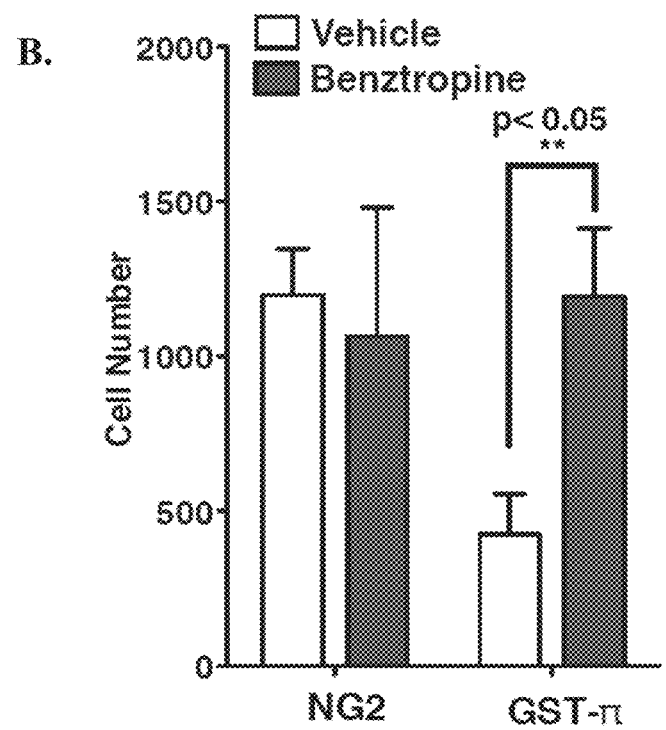

Fig. 9A-B
A.
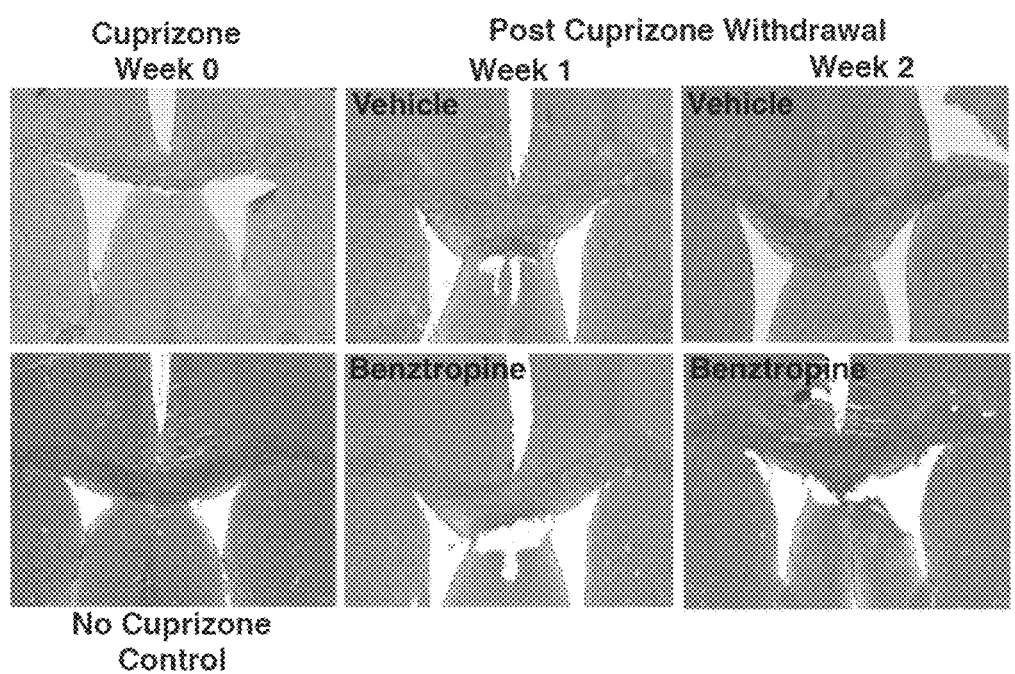
B.
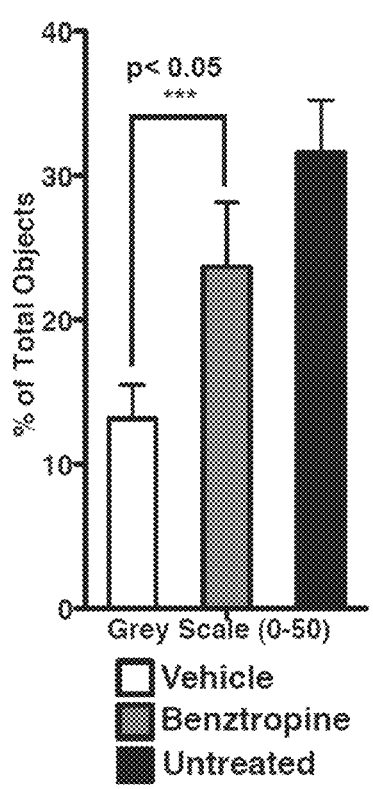

*Fig. 10A-B*
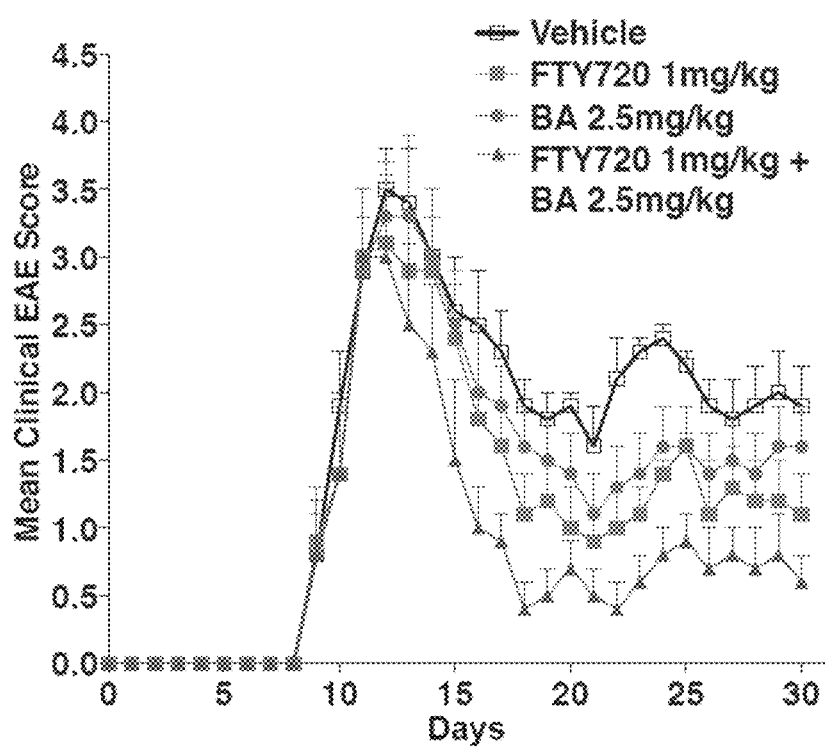
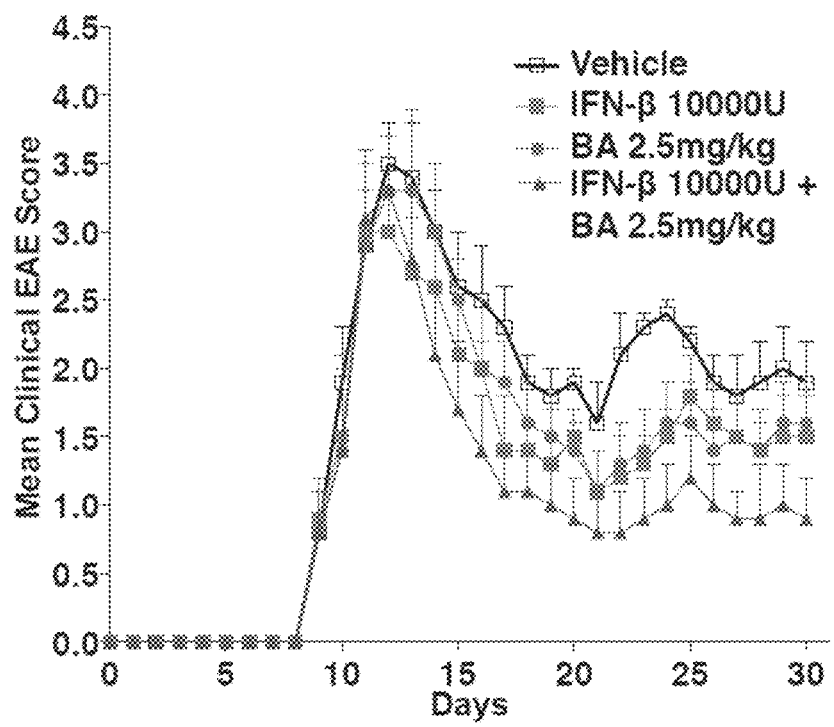

Fig. 10C-D
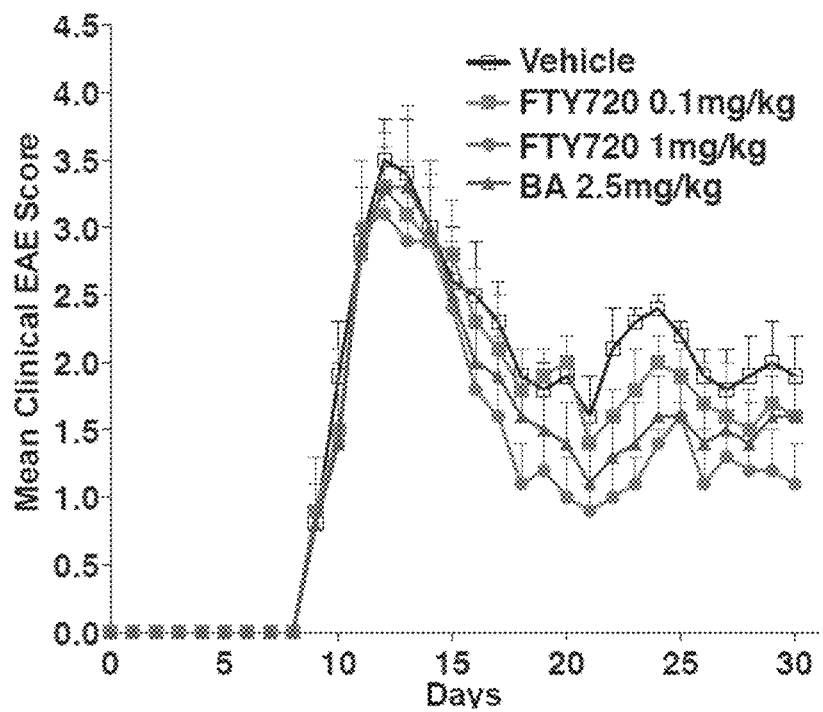
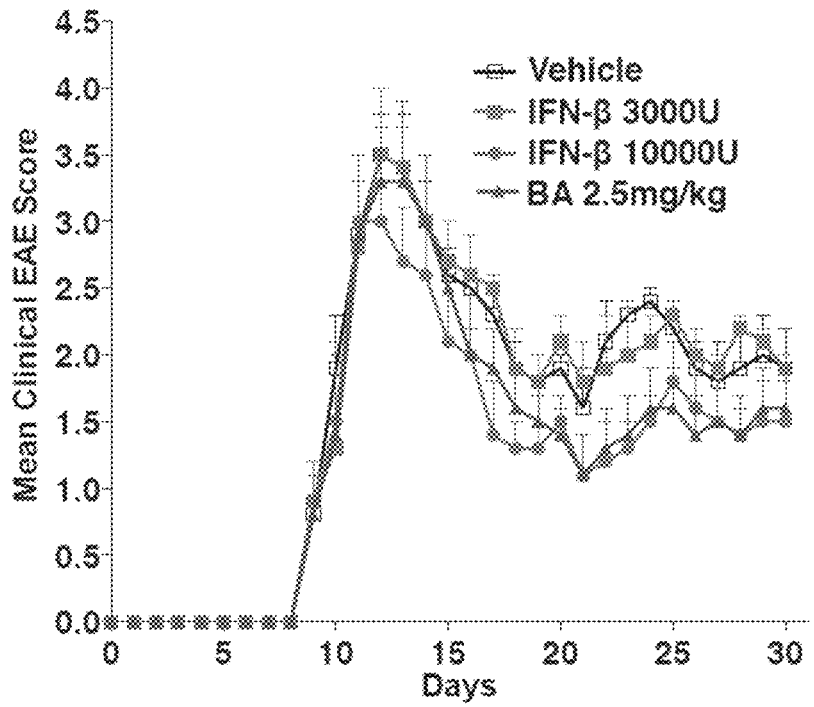

Fig. 10E-F
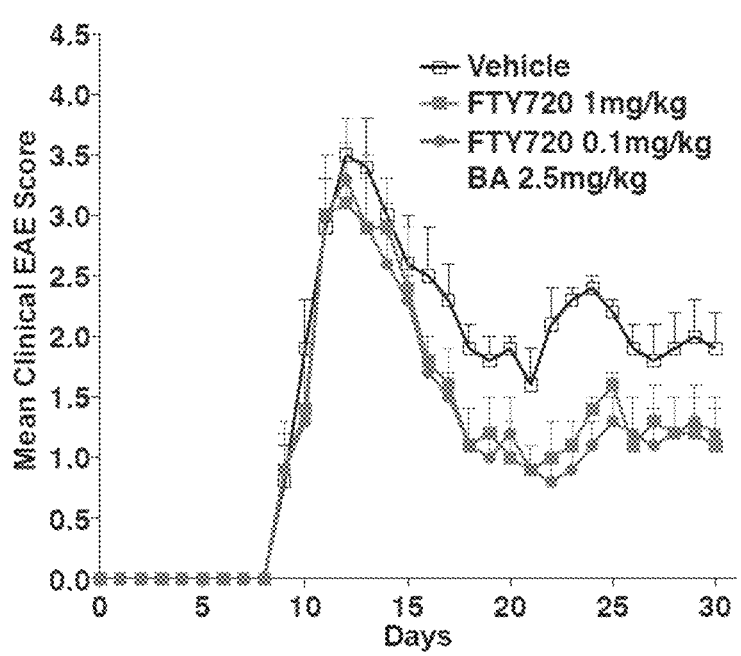
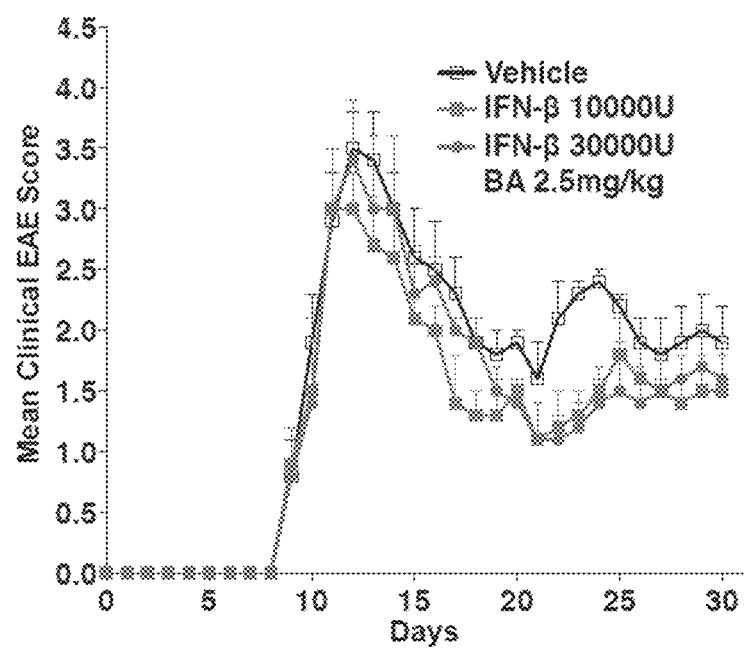

Fig. 11A-B
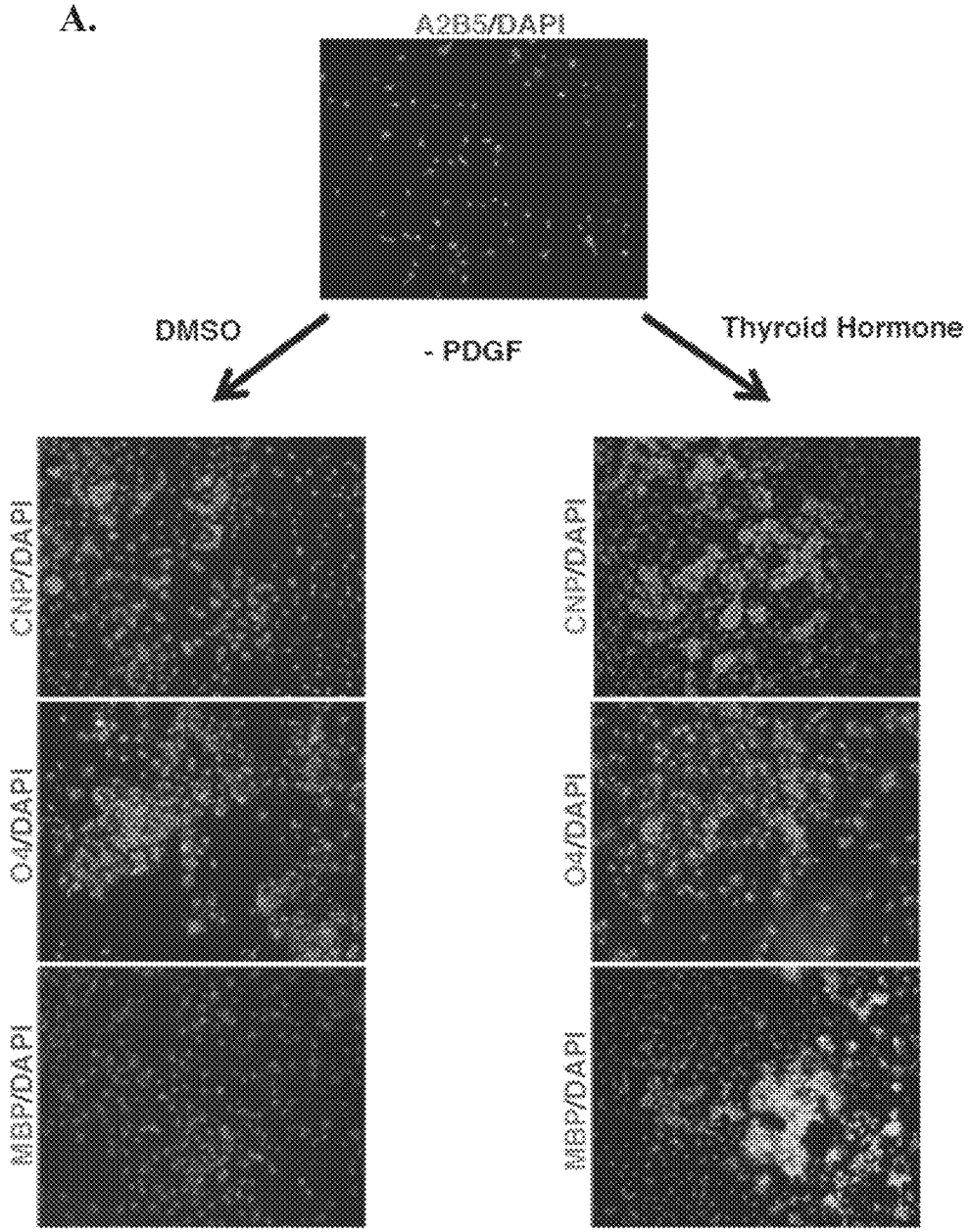
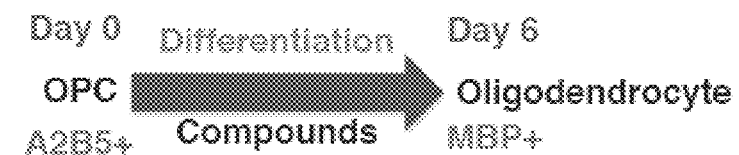

Fig. 12A-B
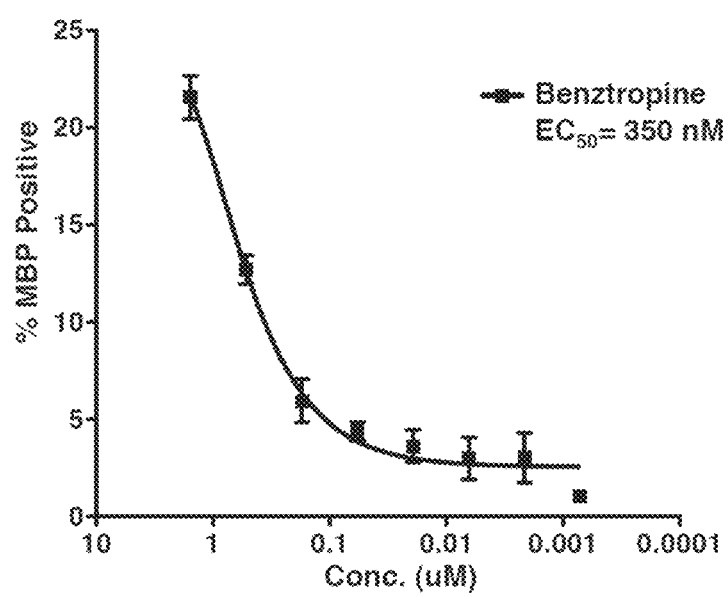
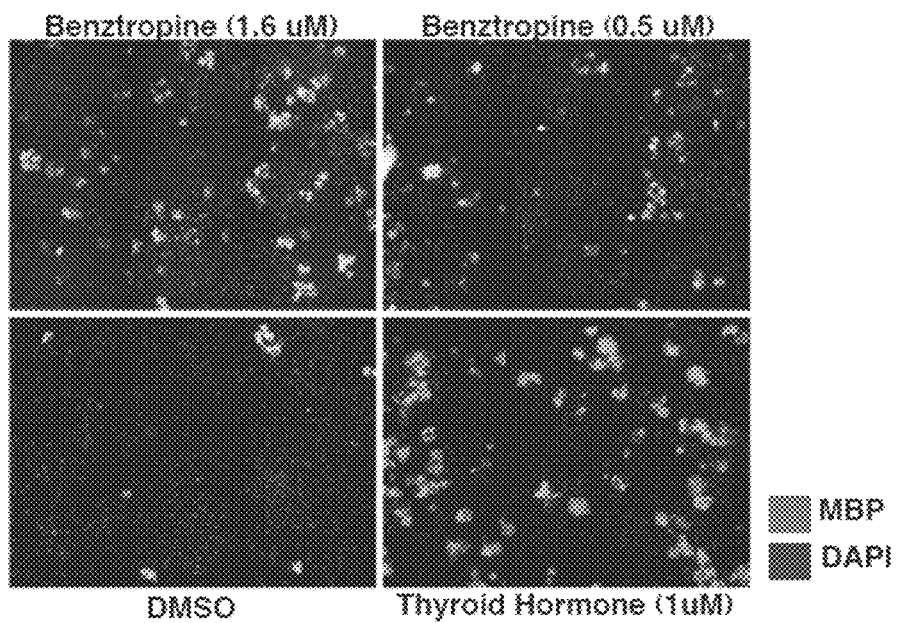

| | OPC/DMSO | Benztropine/DMSO | Thyroid Hormone/DMSO |
|---|---|---|---|
| Apod | 0.58 | 10.79 | 11.21 |
| Enpp6 | 0.14 | 11.58; | 9.06 |
| Mag | 0.10 | 3.70 | 4.64 |
| Mbp | 0.51 | 3.82 | 3.55 |
| Mobp | 0.46 | 2.04 | 67.70 |
| Mog | 0.12 | 7.98 | 29.23 |
| Olig1 | 0.96 | 10.97 | 10.75 |
| Plp | 0.17 | 1.97 | 2.33 |
| Pnlip | 0.44 | 3.34 | 3.01 |
| Tpd52 | 0.24 | 2.28 | 2.15 |

B.

| | OPC/DMSO | Benztropine/DMSO | Thyroid Hormone/DMSO |
|---|---|---|---|
| Ccnd2 | 1.93 | 1.00 | 1.00 |
| Cited2 | 0.99 | 1.10 | 0.98 |
| E2f1 | 0.96 | 0.75 | 0.80 |
| Egr1 | 1.19 | 0.04 | 0.02 |
| Mki67 | 1.18 | 0.67 | 0.81 |
| Nptxr | 1.44 | 0.82 | 0.84 |
| Scd1 | 0.92 | 1.07 | 0.43 |
| Sox11 | 0.87 | 0.36 | 0.23 |
| Top2a | 1.03 | 0.67 | 1.00 |
| Uhrf1 | 1.18 | 0.51 | 0.60 |

Fig. 17A-B
A.
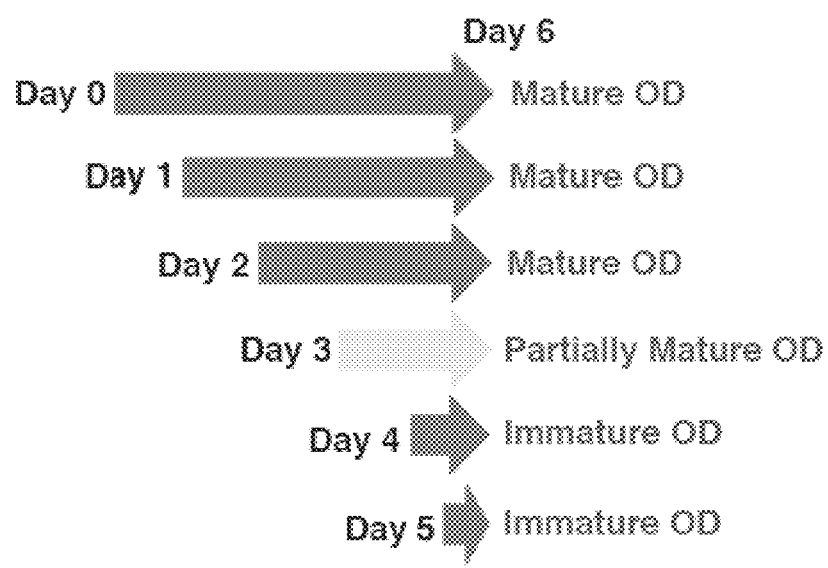
B.
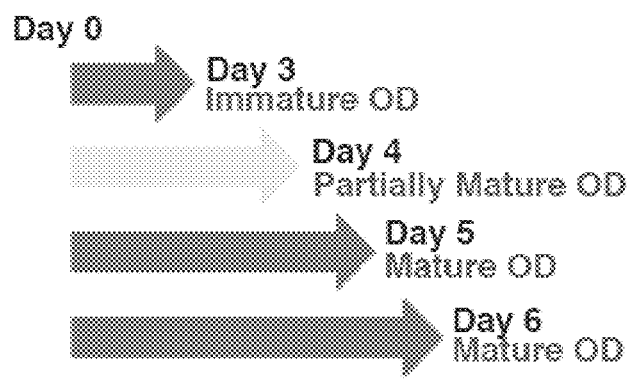

*Fig. 17C-D*
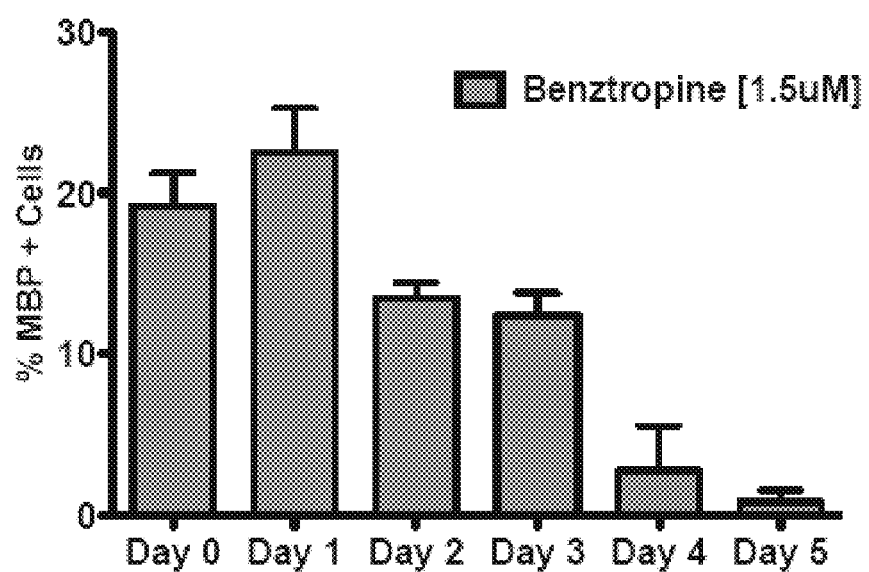
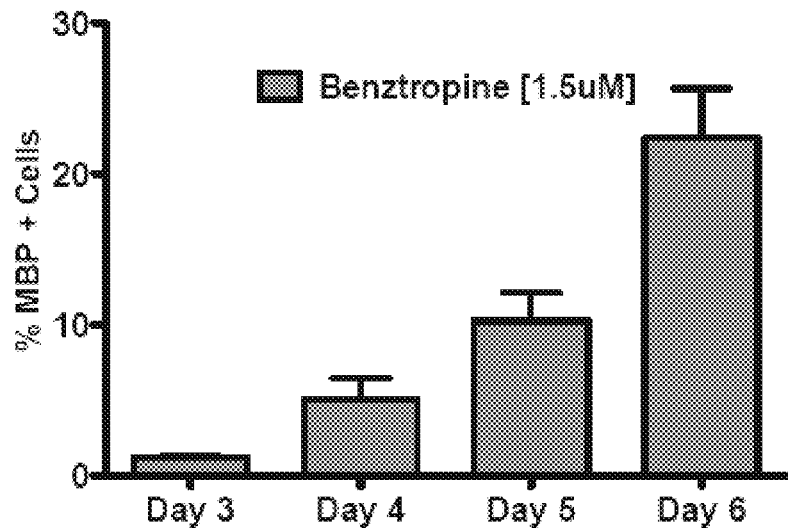

Fig. 19A-B
A.
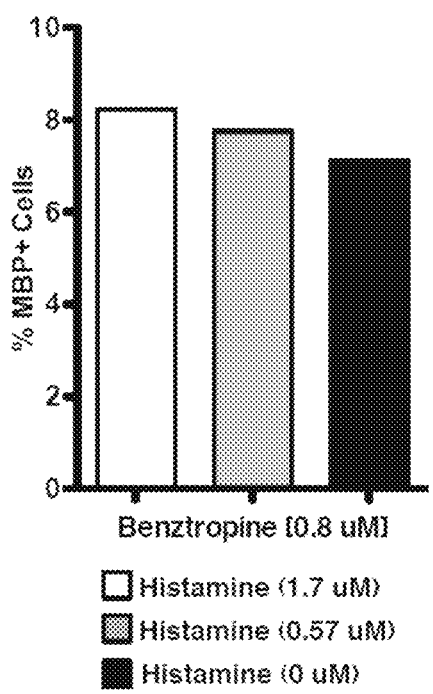
B.
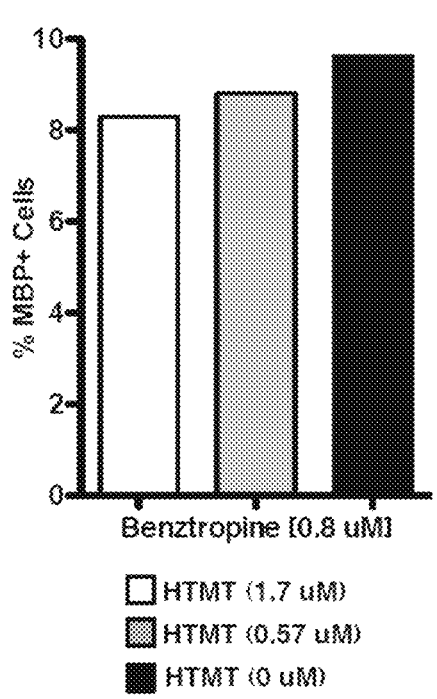

Fig. 20A-B
A.
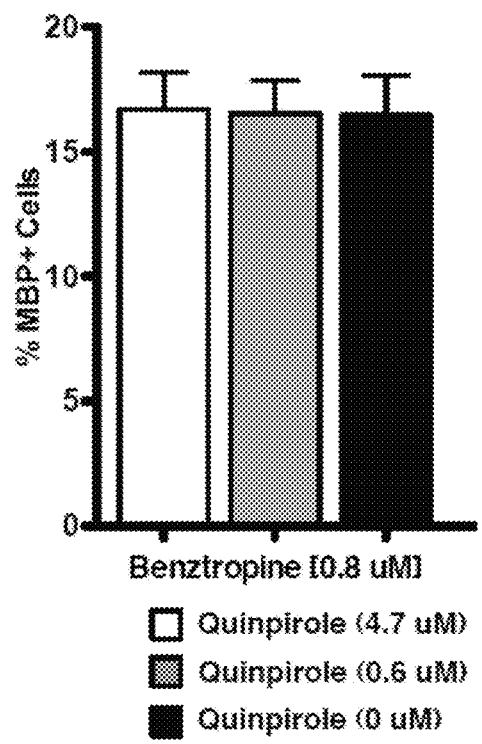
B.
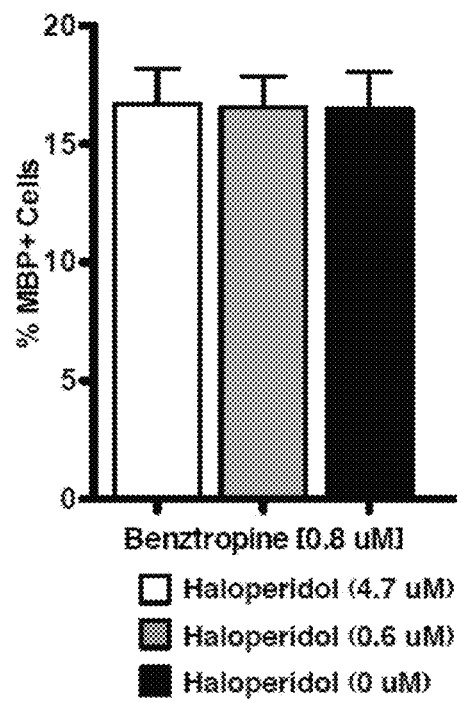

Fig. 24A-B
A.
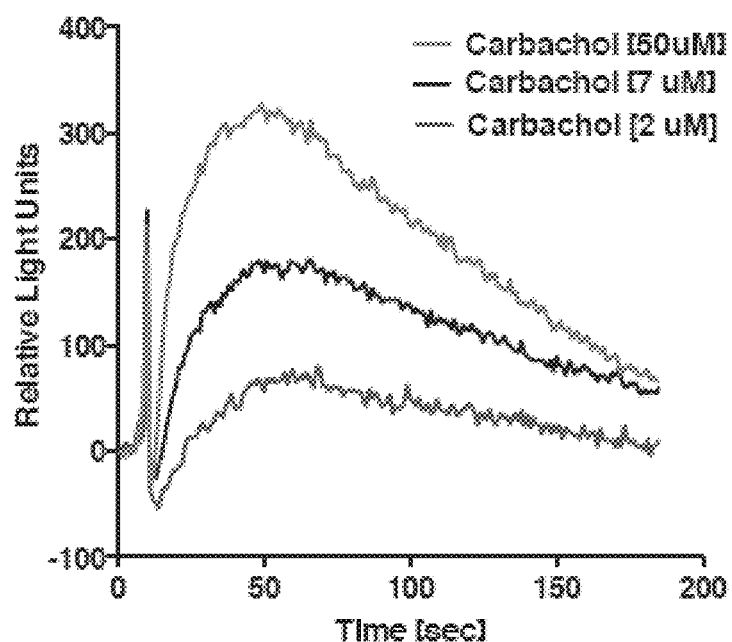
B.
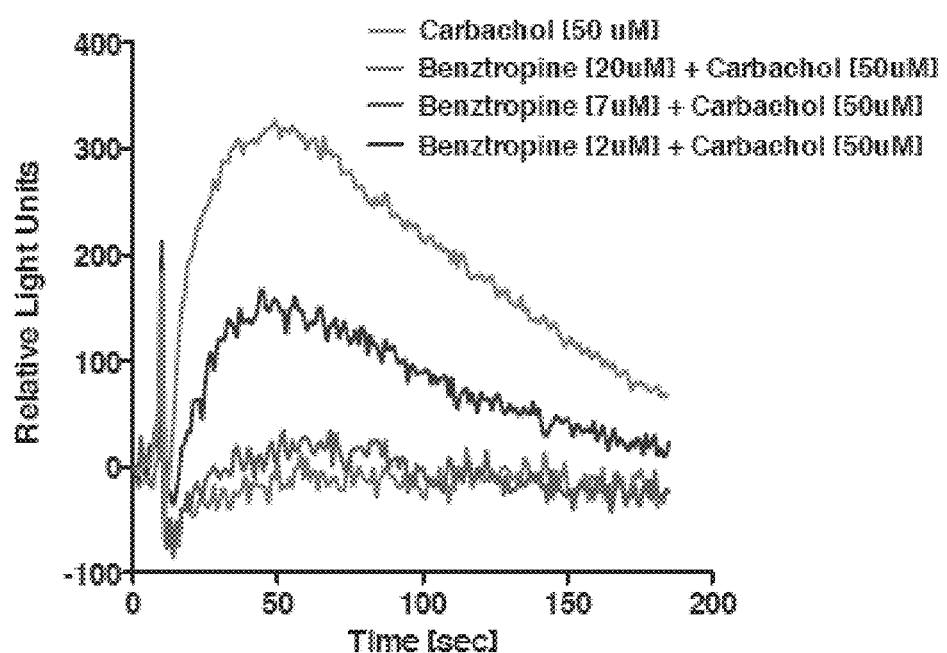

*Fig. 24C-D*
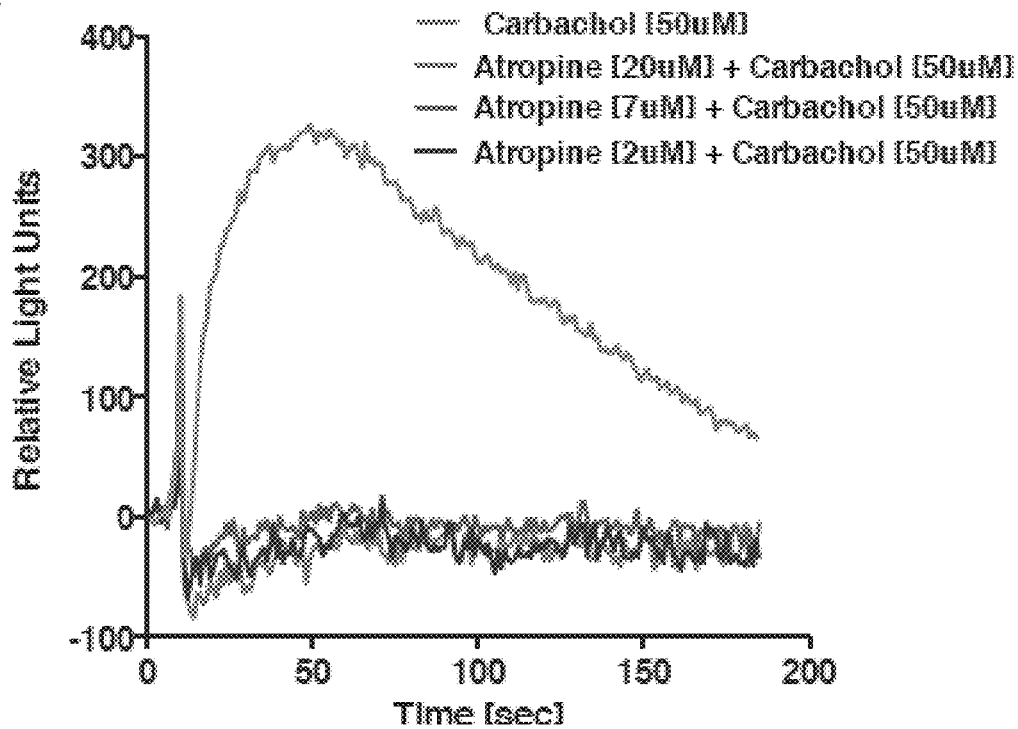
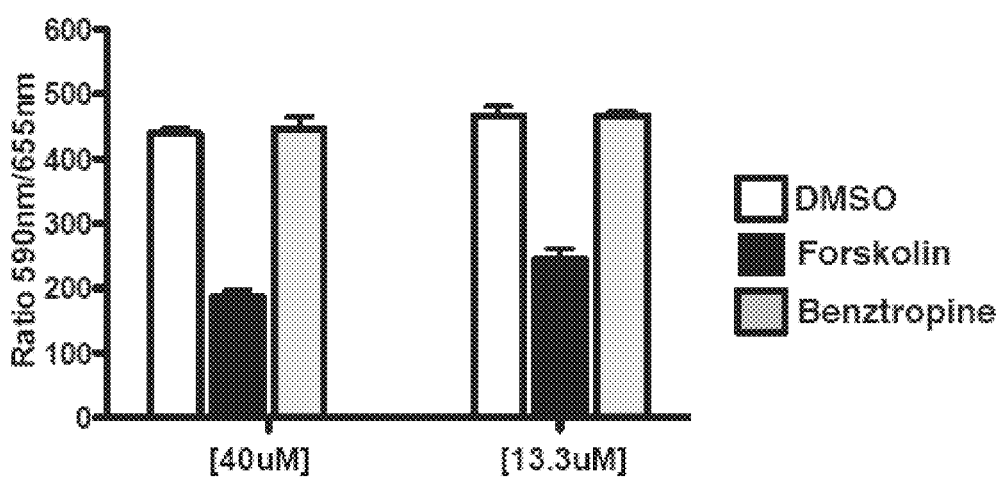

Fig. 27A-D
A.
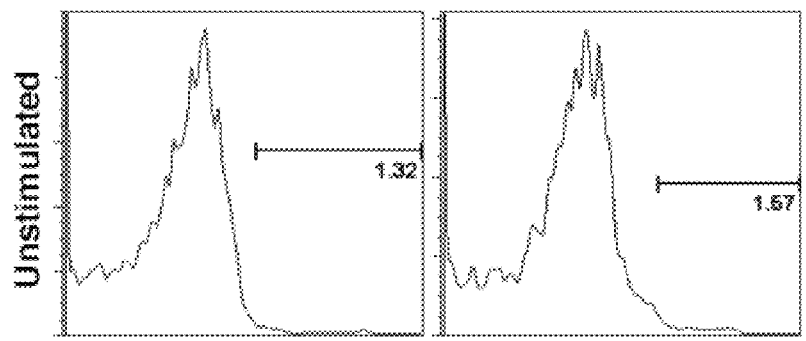
B.
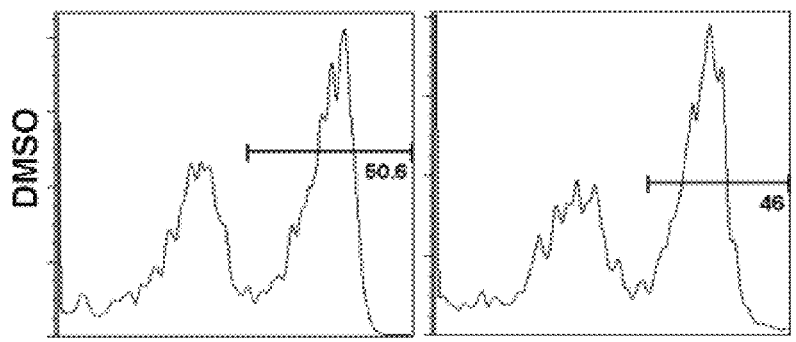
C.
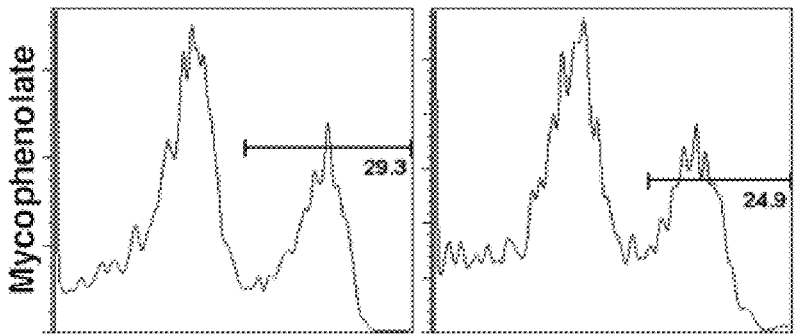
D.
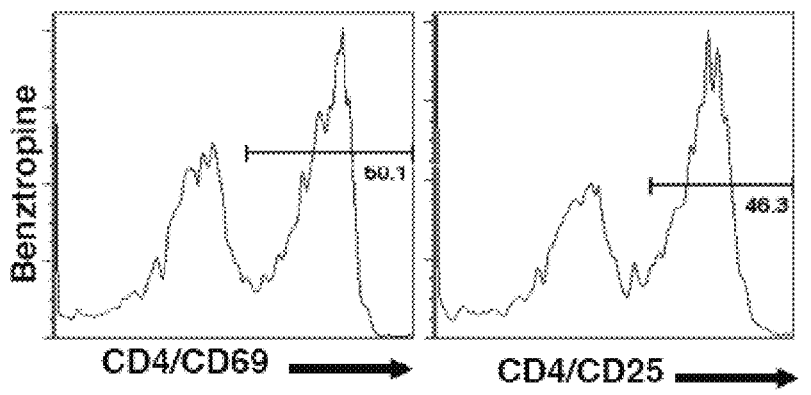

*Fig. 27E-F*
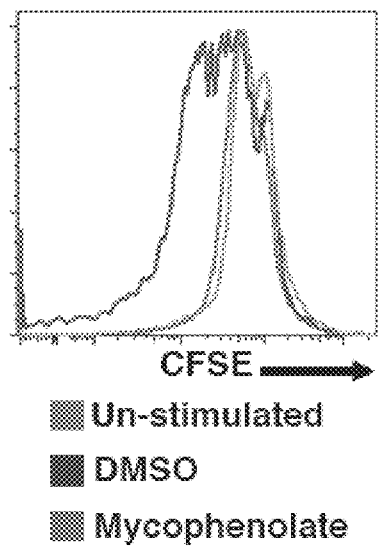
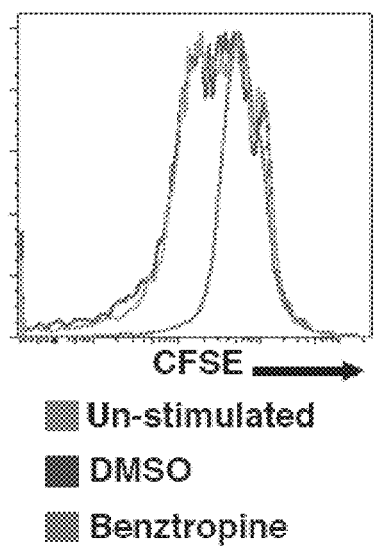

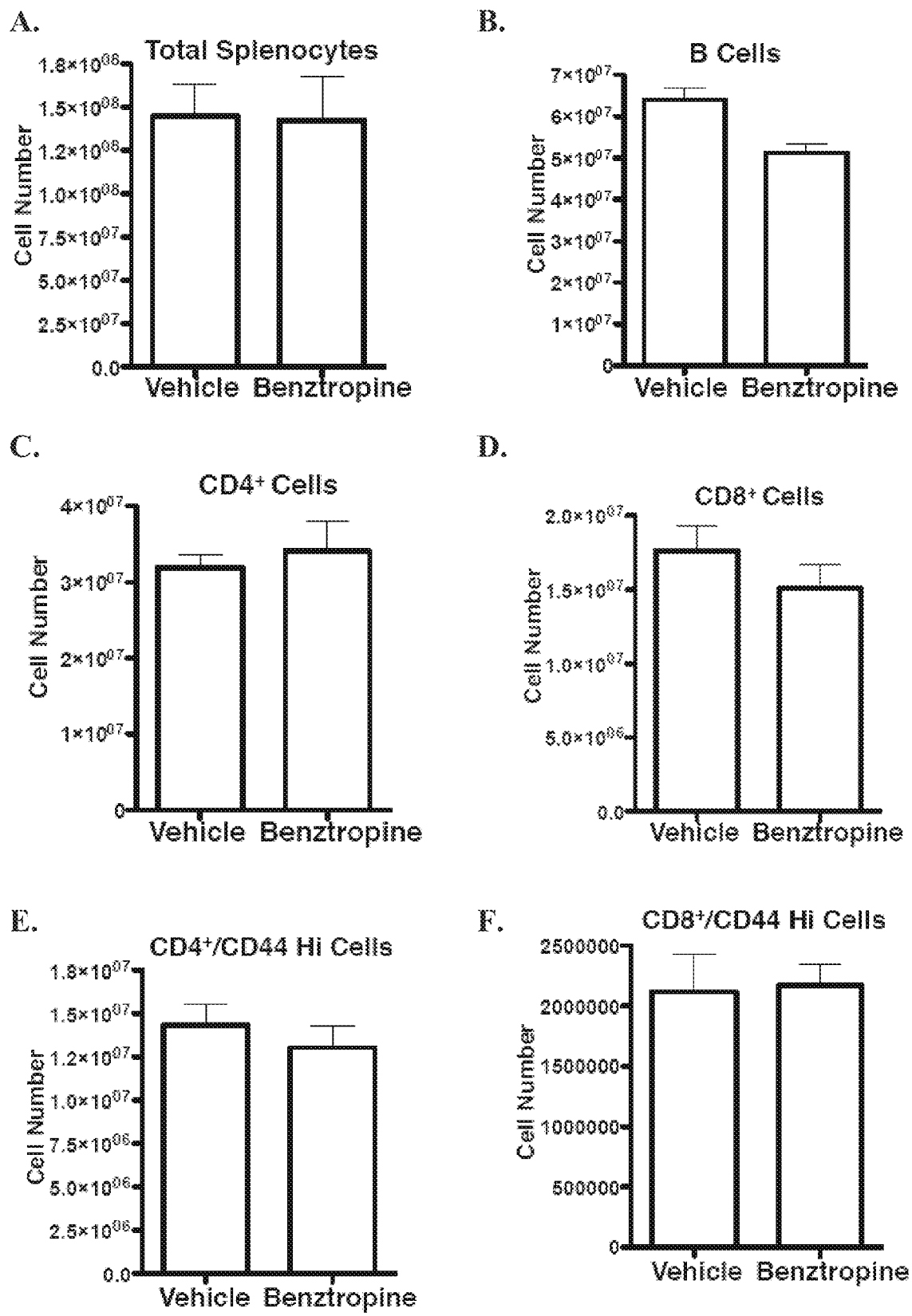
Fig. 28A-F

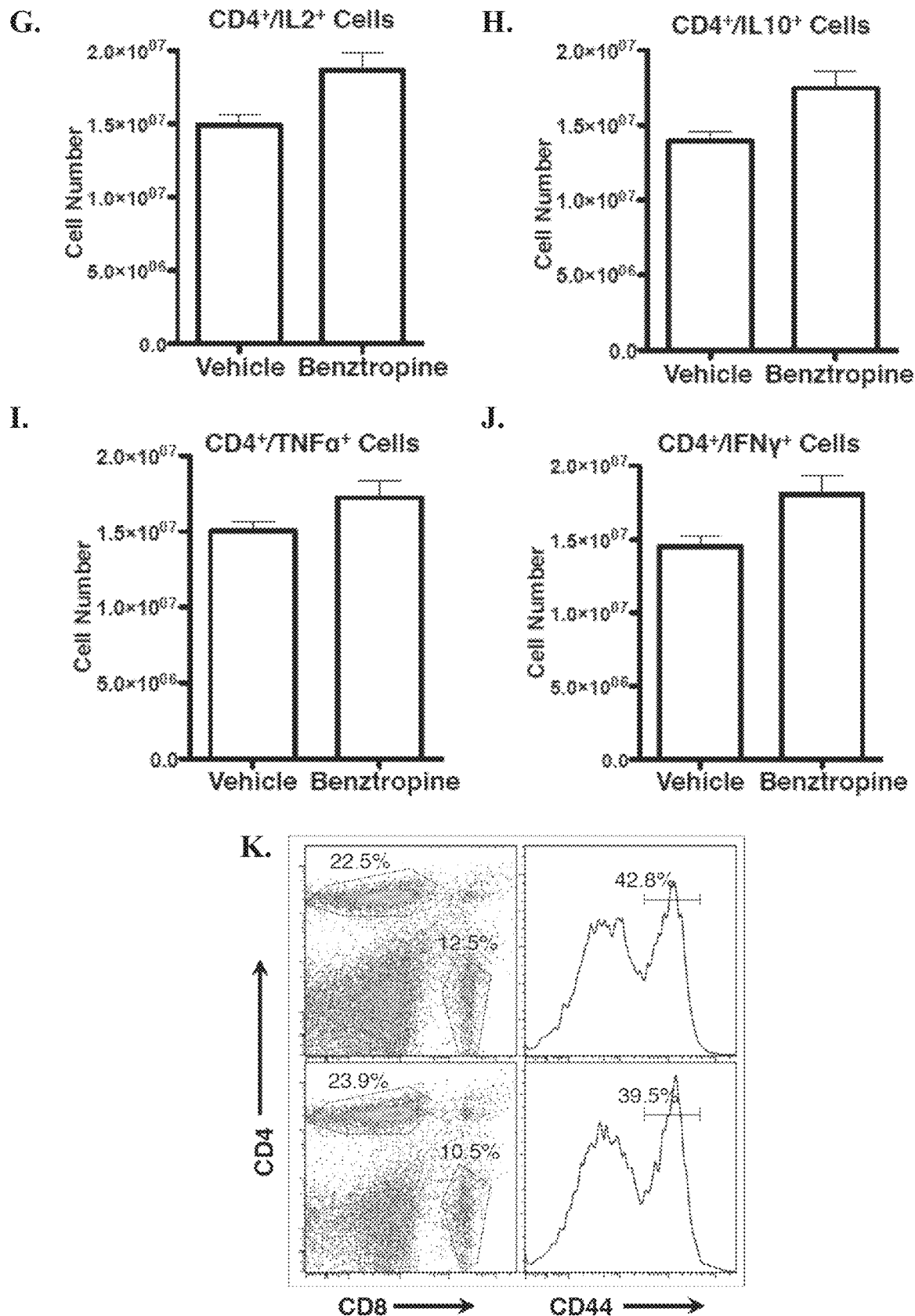
Fig. 28G-K

Fig. 29A-F
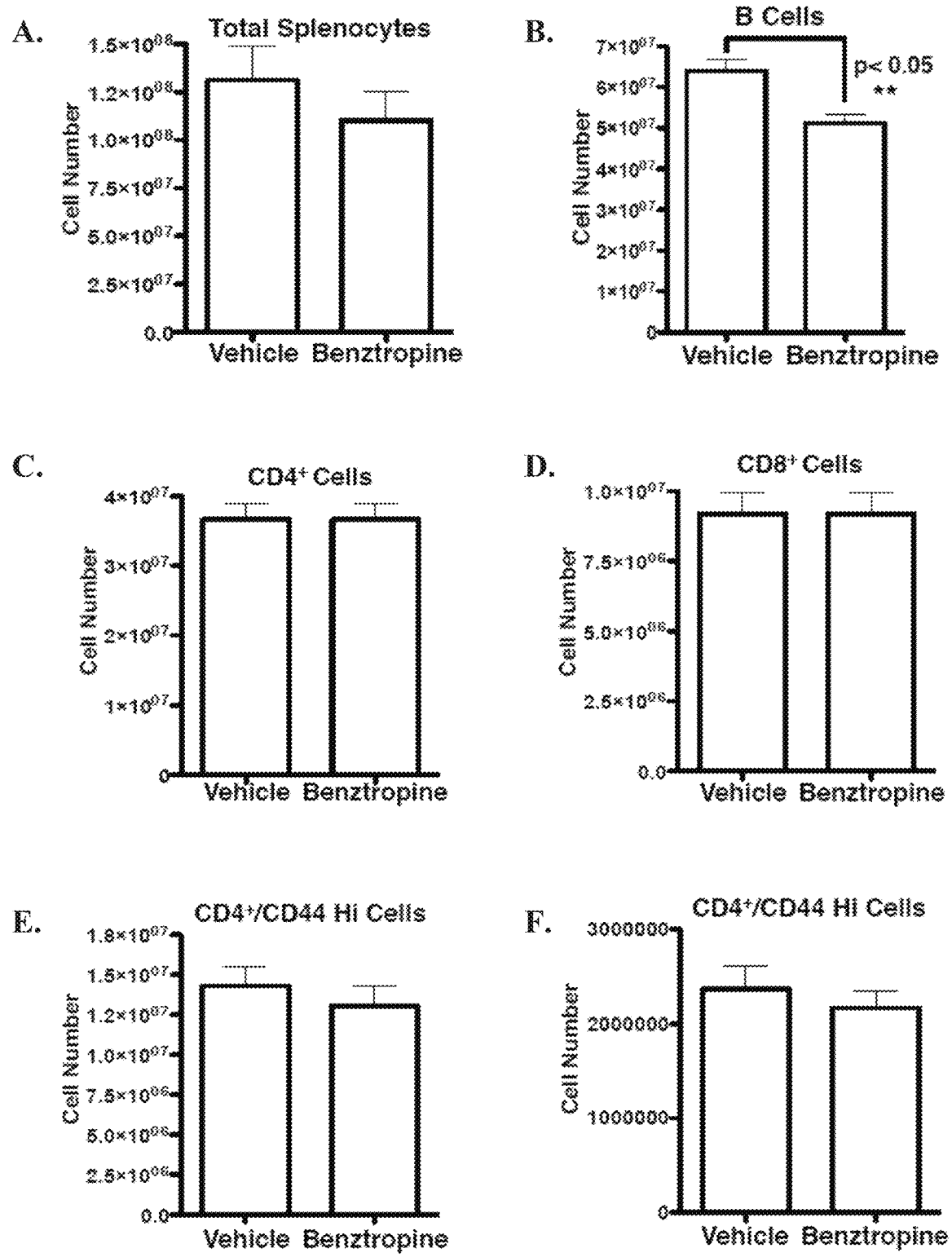

*Fig. 29G-J*
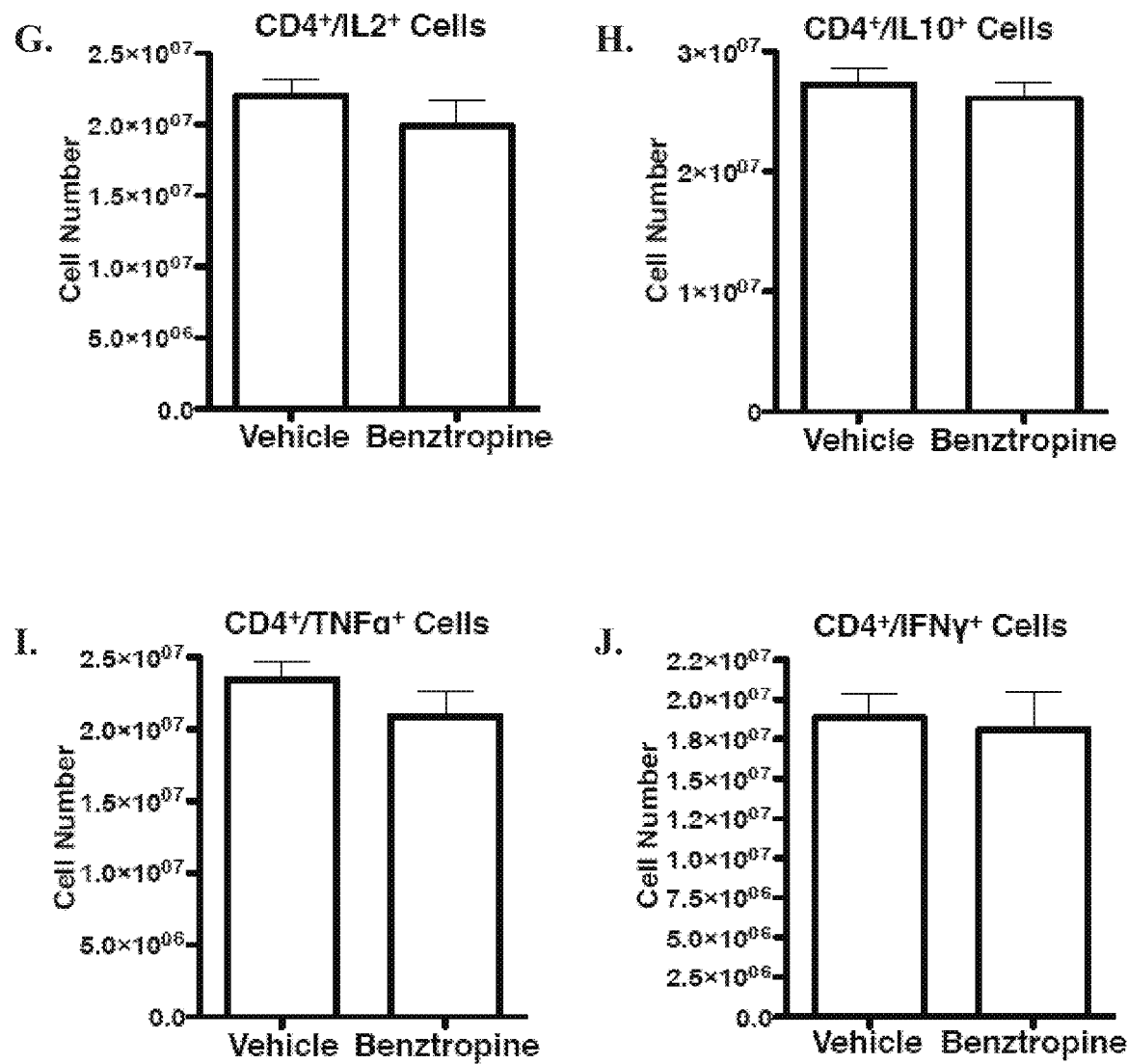

Fig. 30A-C
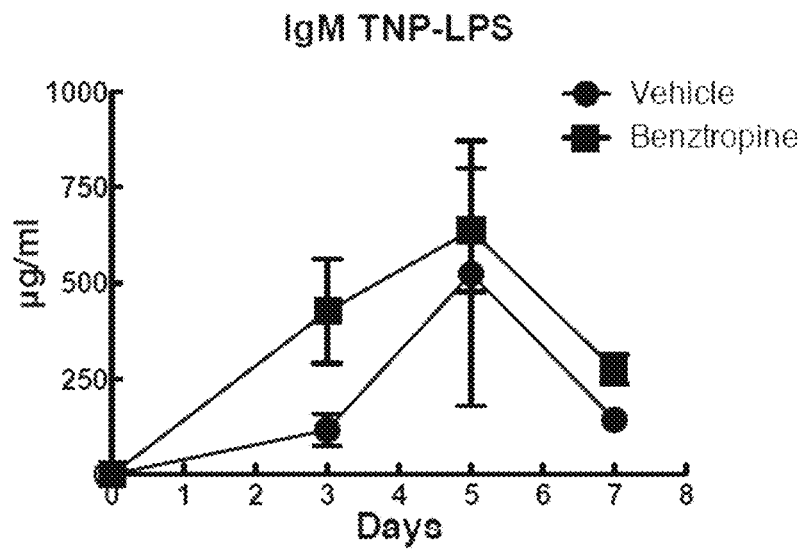
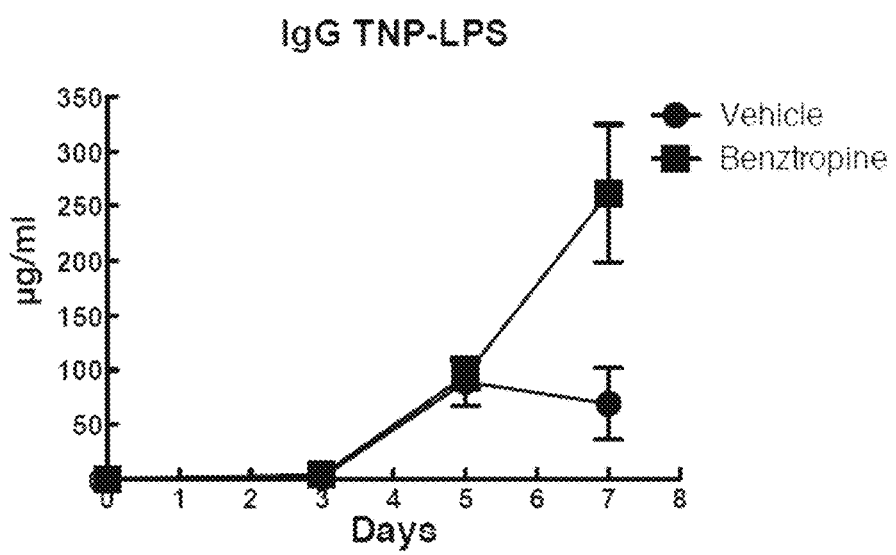
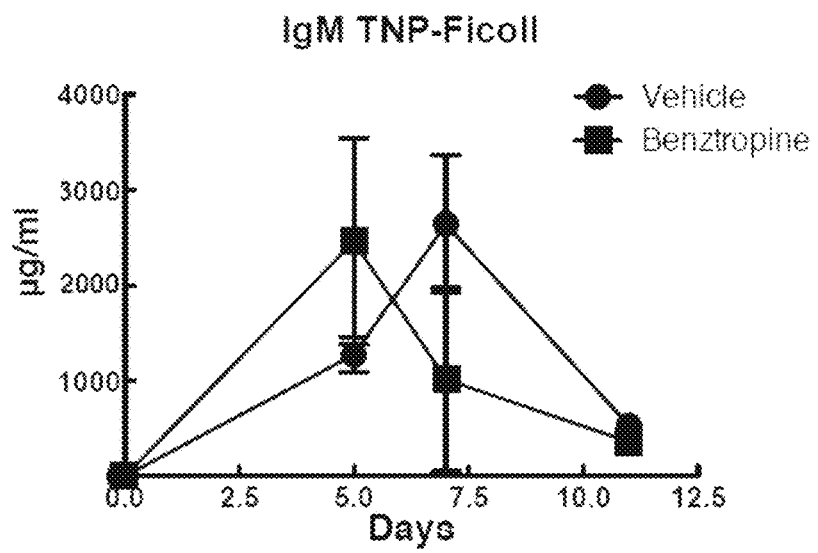

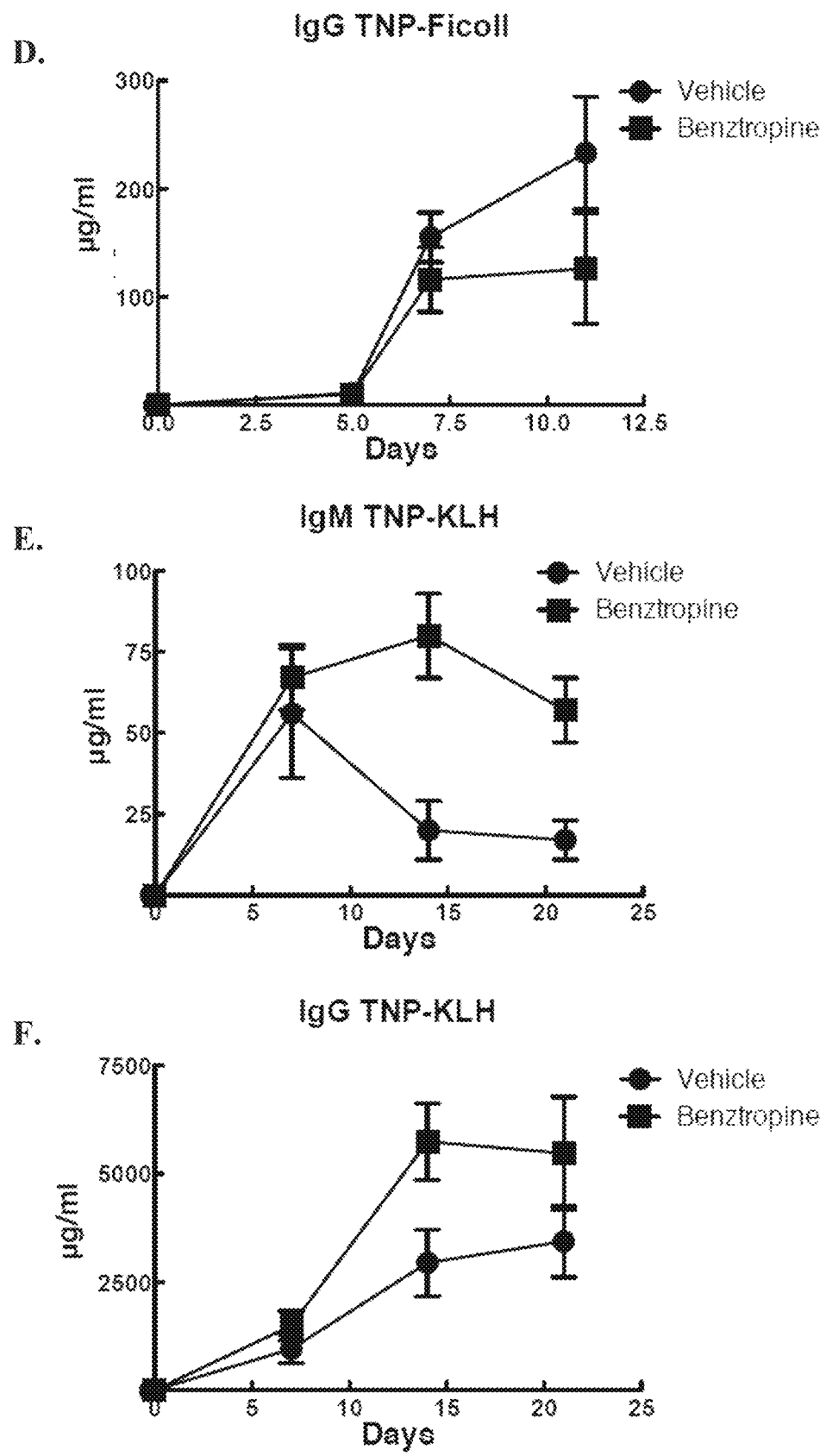
Fig. 30D-F

Fig. 31A-D
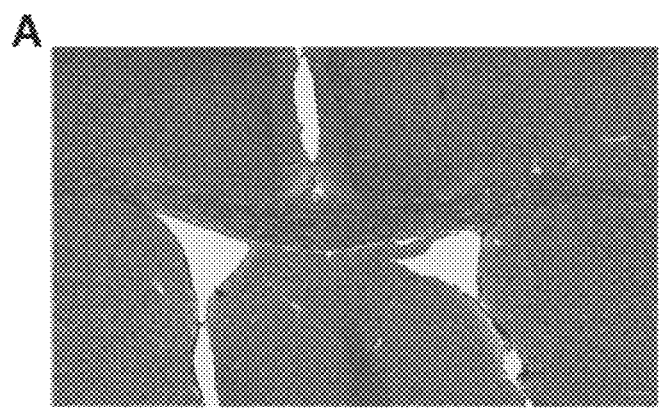
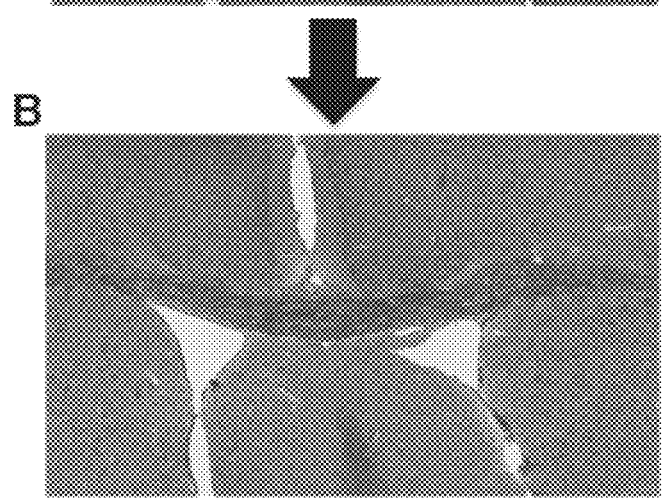
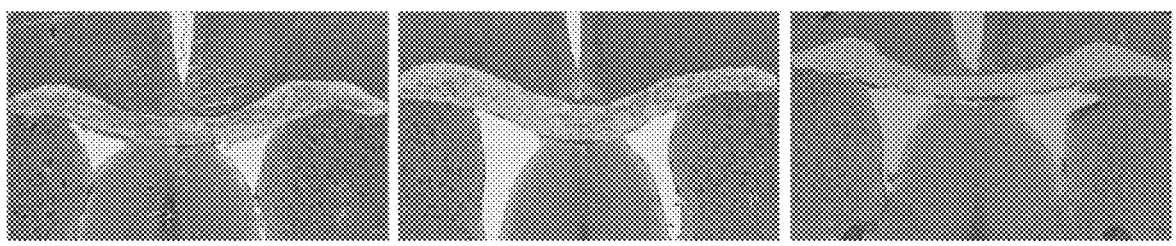

*Fig. 33A-B*
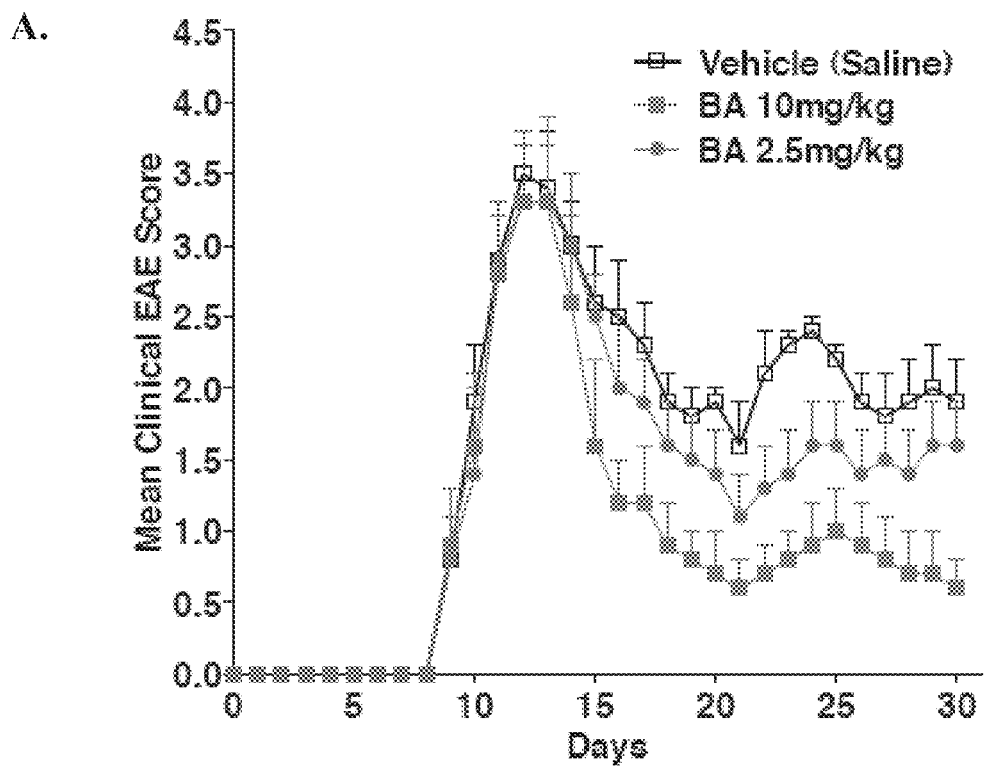
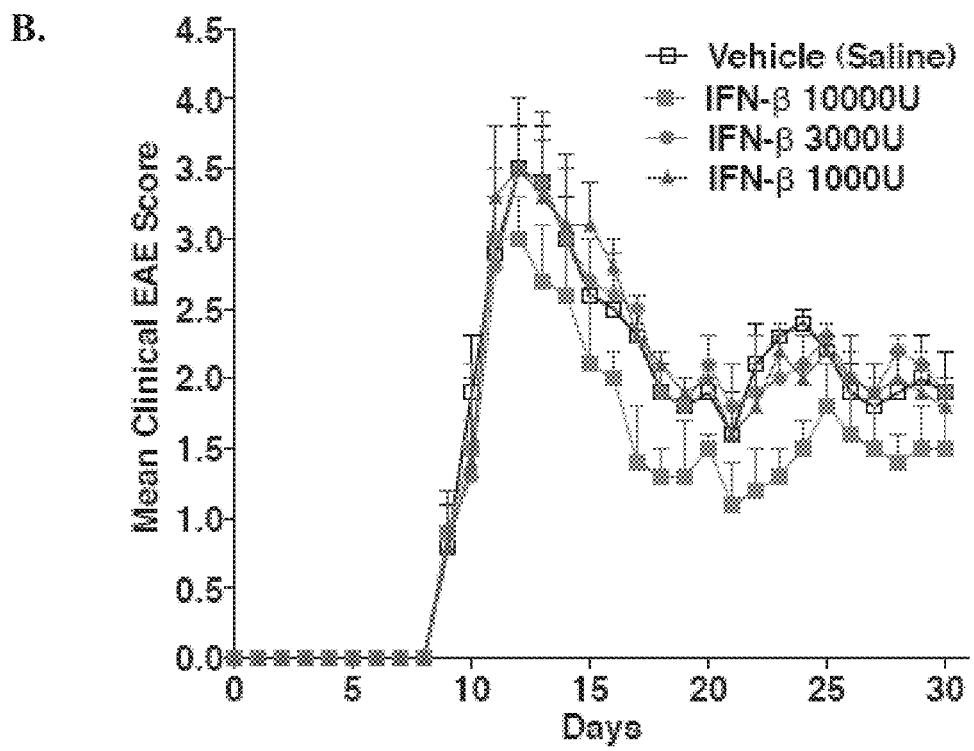

Fig. 33C-D
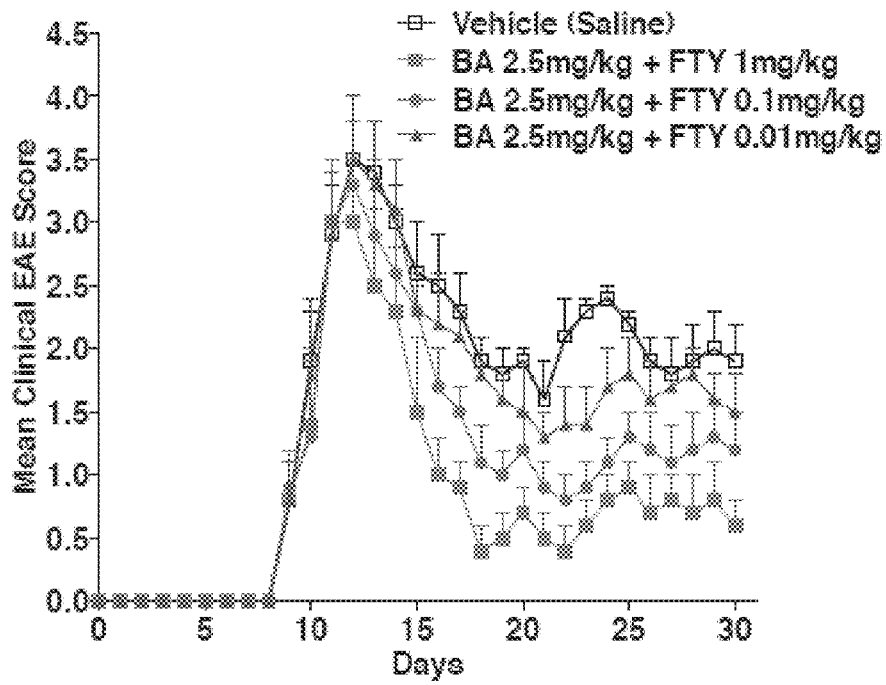
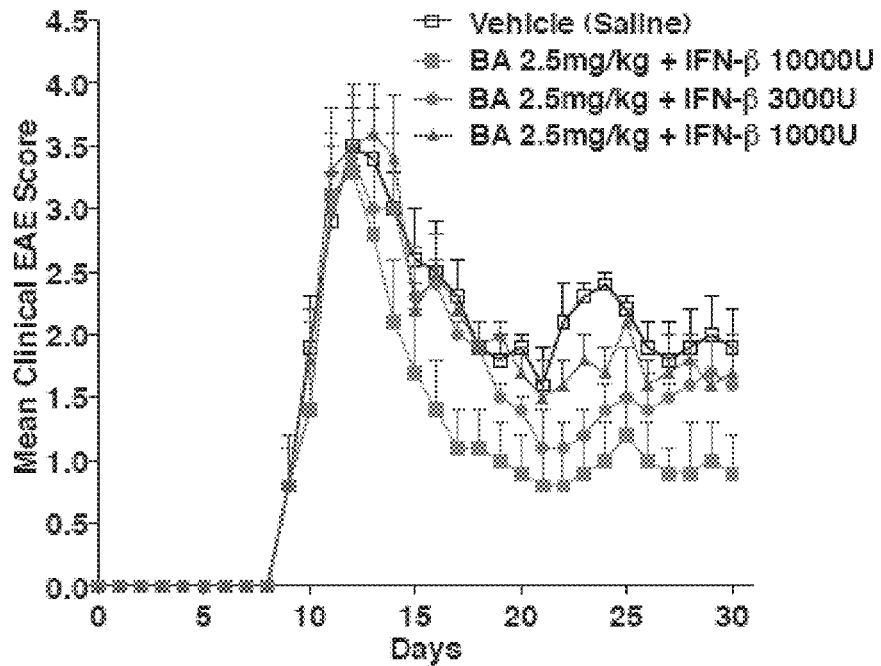

Fig. 33E-F
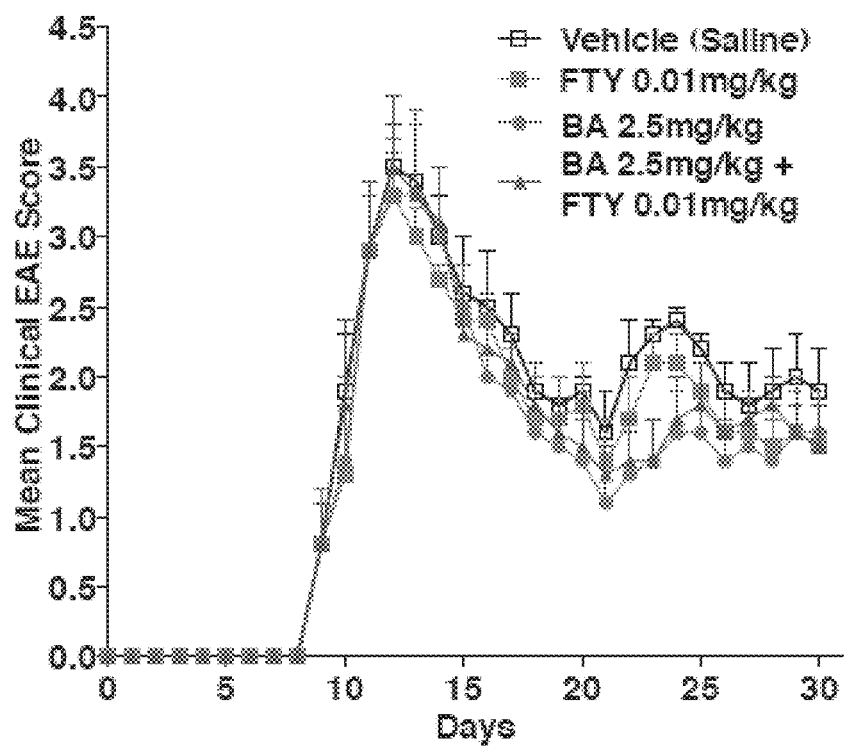
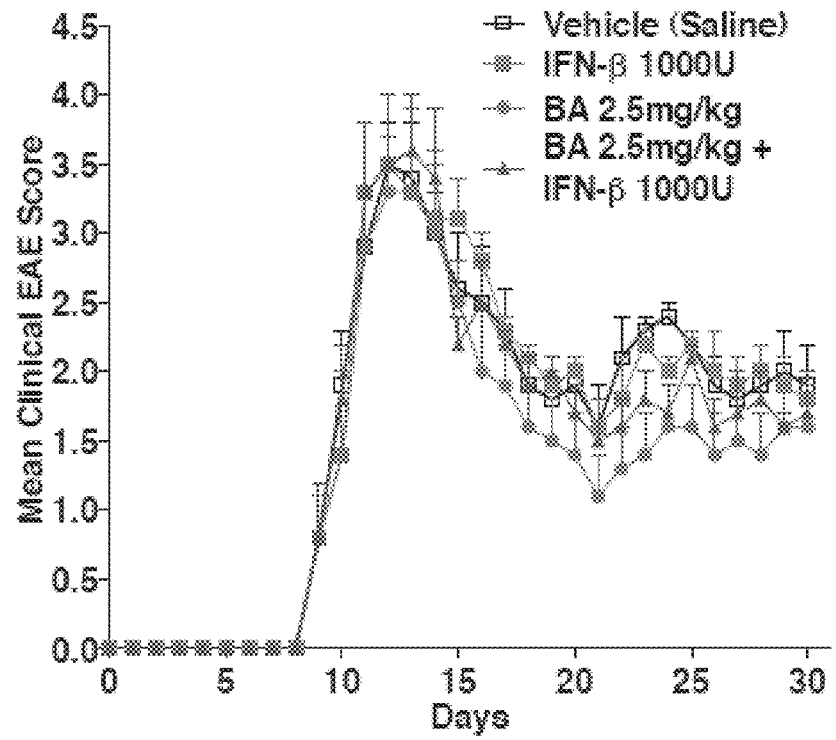

Fig. 34A-B
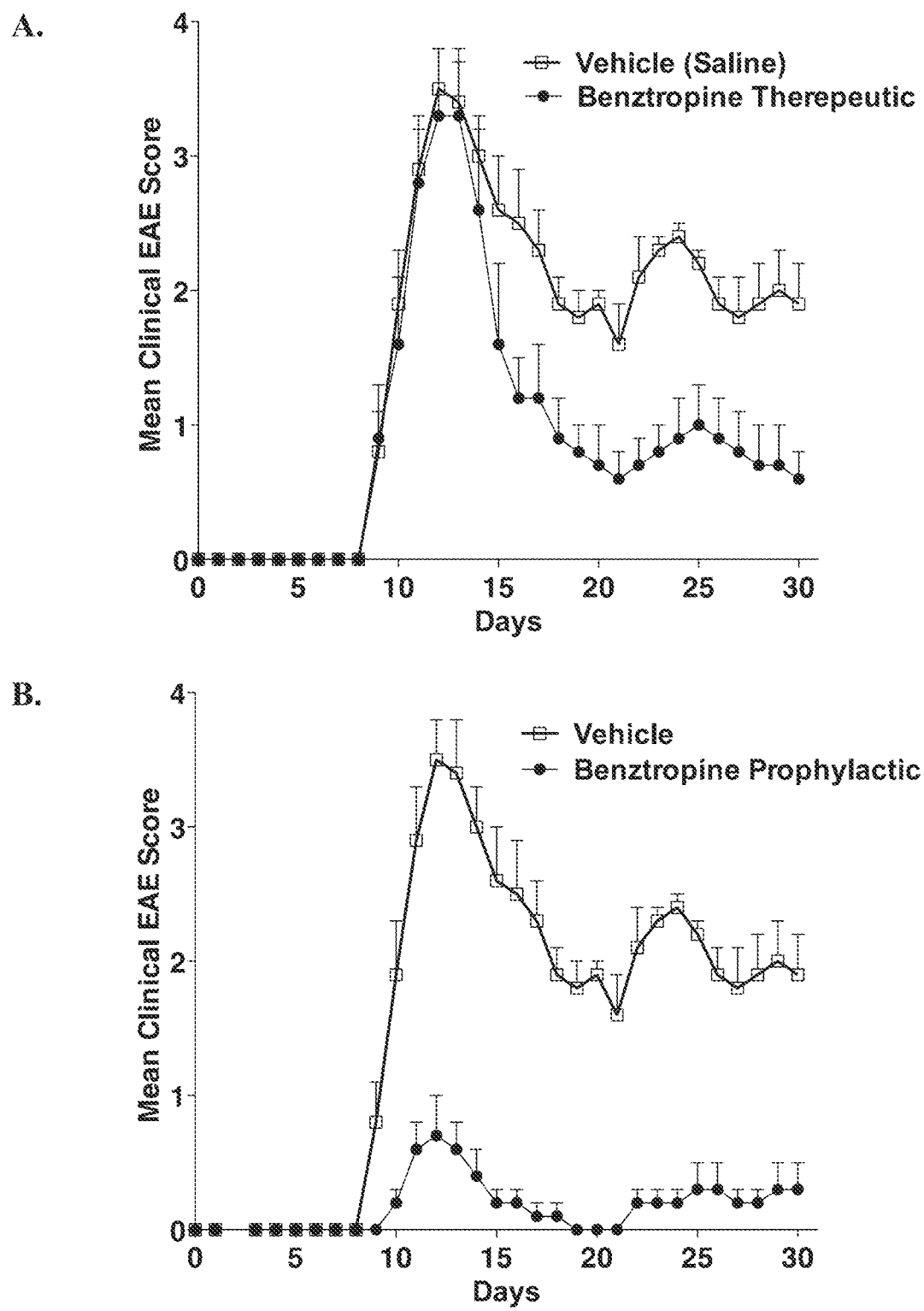

*Fig. 34C-D*
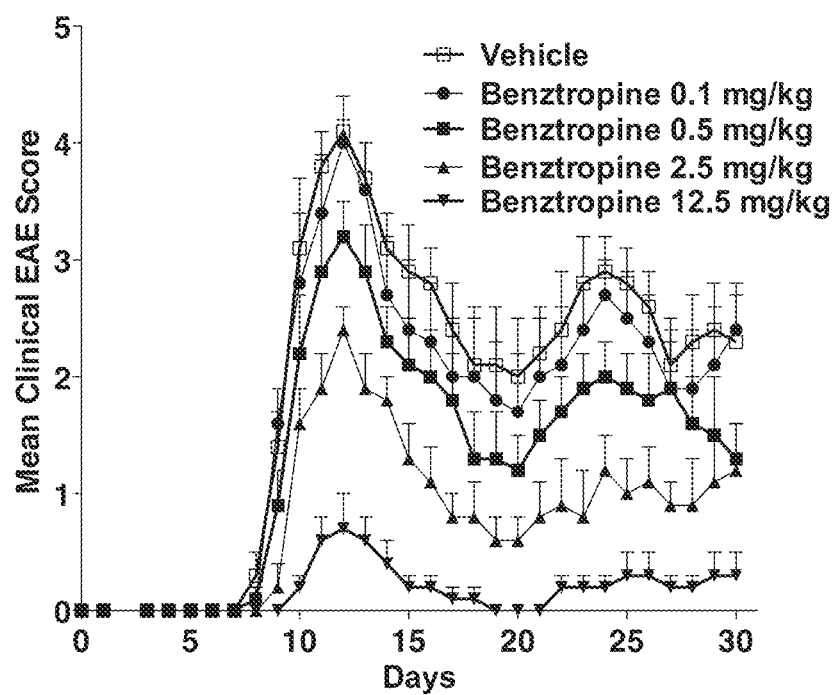
C.
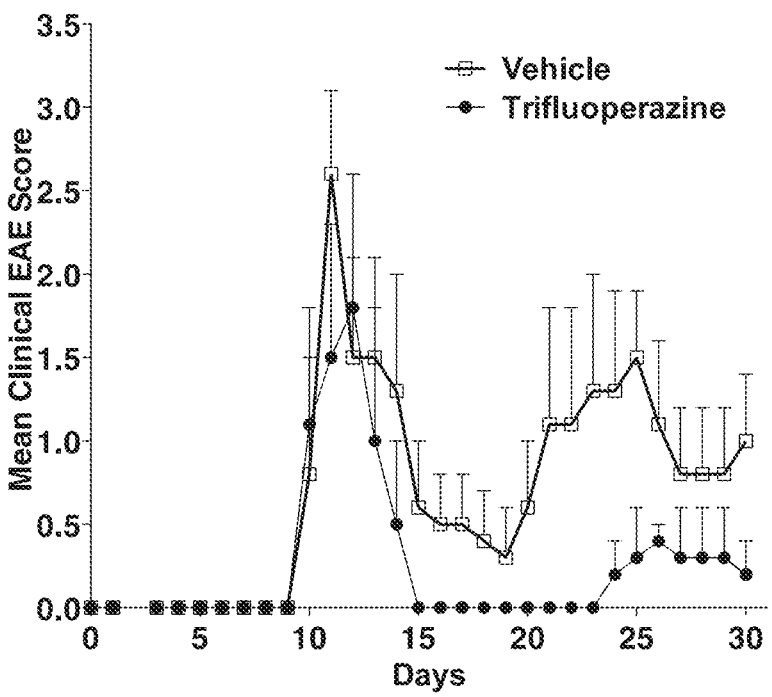
D.

*Fig. 34E-F*
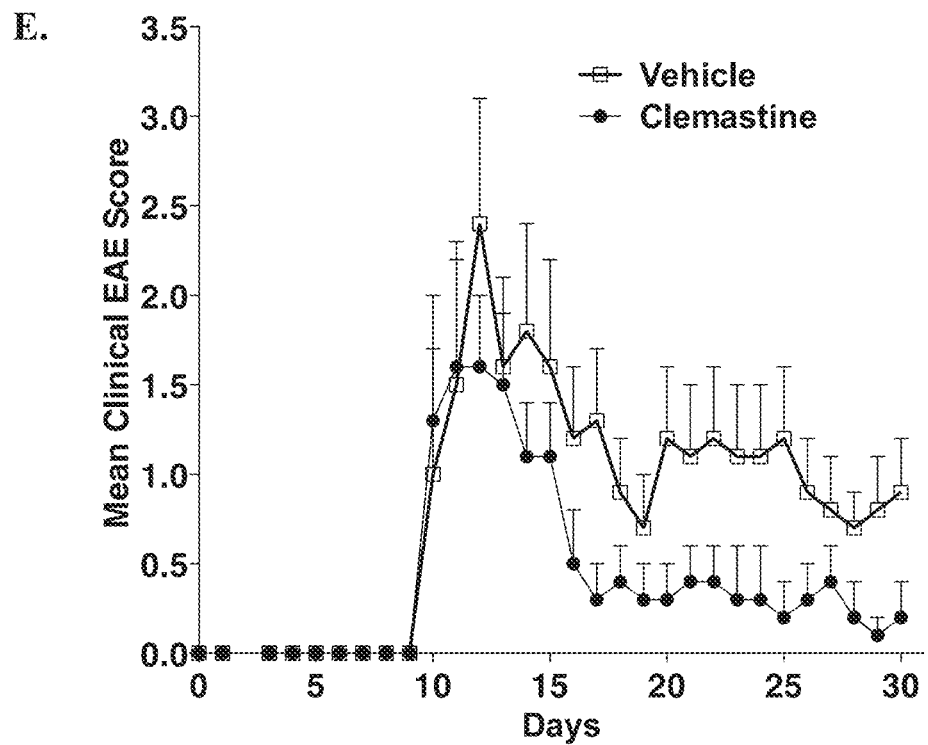
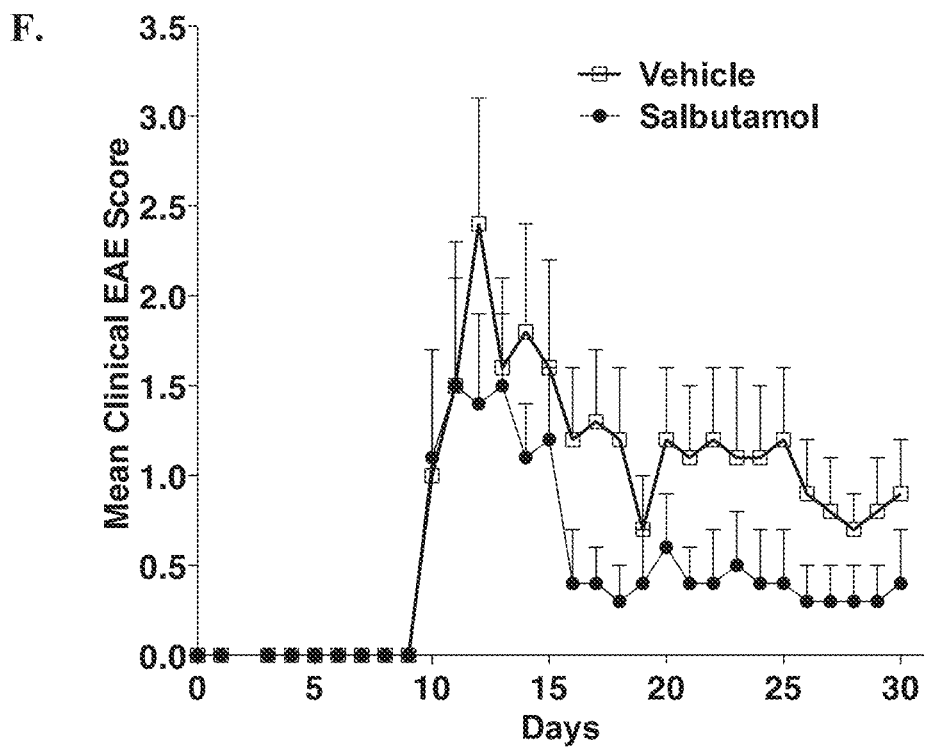

DIRECTED DIFFERENTIATION OF OLIGODENDROCYTE PRECURSOR CELLS TO A MYELINATING CELL FATE

CROSS-REFERENCES TO RELATED APPLICATIONS

The present application is a divisional of U.S. application Ser. No. 13/985,342, filed Oct. 18, 2013, which is a national stage application under 35 U.S.C. § 371 of International Application No. PCT/US2012/025712, filed Feb. 17, 2012, which claims priority to U.S. Provisional Application No. 61/444,666, filed Feb. 18, 2011, the entire content of which is incorporated by reference in its entirety.

BACKGROUND OF THE INVENTION

Multiple sclerosis (MS) afflicts approximately 400,000 people in the United States and 2.5 million worldwide. MS is an inflammatory disease in which myelin sheaths around the axons of the brain and spinal cord are damaged. In MS as well as other demyelinating diseases, autoimmune inflammatory attack against myelin and oligodendrocytes causes demyelination. The thinning or loss of myelin surrounding axons impairs the ability of the axons to effectively conduct signals and results in progressive neuronal damage.

Remyelination is the process by which new myelin sheaths are generated around axons. Remyelination persists throughout adulthood in the CNS and involves the generation of new myelinating oligodendrocytes (C. Ffrench-Constant, M. C. Raff, *Nature*, 319, 499 (1986)). Despite controversy regarding their intrinsic in vitro and in vivo lineage potential (M. C. Nunes et al., *Nat Med*, 9, 439 (2003); S. Belachew et al., *J Cell Biol*, 161, 169 (2003); T. Kondo, M. Raff, *Science*, 289, 1754 (2000); Jackson, 2006; Zhu, 2011; Richardson, 2011; R. J. Franklin, C. Ffrench-Constant, *Nat Rev Neurosci*, 9, 839 (2008)), compelling evidence indicates that a widespread proliferating population of nerve/glial antigen-2 (NG2), platelet-derived growth factor receptor (alpha subunit, PDGFRa) positive cells, termed NG2-glia or oligodendrocyte precursor cells (OPCs), are the major source of newly formed mature oligodendrocytes required for remyelination (P. J. Homer et al., *J Neurosci*, 20, 2218 (2000); M. C. Nunes et al., *Nat Med*, 9, 439 (2003); J. M. Gensert, J. E. Goldman, *Neuron*, 19, 197 (1997); M. S. Windrem et al., *Nat Med*, 10, 93 (2004); R. J. Franklin, C. Ffrench-Constant, *Nat Rev Neurosci*, 9, 839 (2008); Richarson, 2011).

Remyelination can occur following the loss of myelin in diseases such as MS, thus restoring neurological function to axons. However, although remyelination can occur in the early stages of MS, oligodendrocytes are unable to completely rebuild the myelin sheath, and repeated inflammatory attacks ultimately lead to fewer effective remyelinations until plaques build up around the damaged axons. A primary cause of remyelination failure is the progressive inability of somatic oligodendrocyte precursor cells to differentiate at the sites of injury. Thus, remission in MS is largely dependent upon OPCs migrating to sites of injury, and subsequently differentiating to a mature cell fate capable of repair (J. R. Patel, R. S. Klein, *FEBS Lett*, 585, 3730 (2011); D. Kremer et al., *Ann Neurol*, 69, 602 (2011); A. Chang et al., *N Engl J Med*, 346, 165 (2002)). Studies aimed at evaluating the presence and relative densities of OPCs at sites of chronically demyelinated MS lesions indicate that it is not a failure of repopulation or migration of OPCs, but rather inhibition of OPC differentiation at sites of injury that contributes to disease progression (D. M. Chari, W. F. Blakemore, *Glia*, 37, 307 (2002); D. M. Chari et al., *J Neurosci Res*, 73, 787 (2003); G. Wolswijk, *J Neurosci*, 18, 601 (1998); A. Chang et al., *N Engl J Med*, 346, 165 (2002); T. Kuhlmann et al., *Brain*, 131, 1749 (2008)).

There is no known cure for MS. For treating acute inflammatory attacks, intravenous corticosteroids are typically administered. Other treatments for MS involve the administration of an immunomodulator. Although immunomodulators are able to reduce the frequency and severity of attacks or accumulation of lesions, they do not promote remyelination of damaged axons.

BRIEF SUMMARY OF THE INVENTION

In one aspect, the present invention provides for methods of stimulating increased myelination of nerves in a subject in need thereof. In some embodiments, the method comprises administering to the subject a therapeutically effective dose of a neurotransmitter receptor modulating agent selected from a muscarinic receptor antagonist, a dopamine receptor antagonist, a histamine receptor antagonist, a beta adrenergic receptor modulator, and an opioid receptor modulator; thereby stimulating increased myelination of nerves in the subject.

In another aspect, the present invention provides for methods of treating a subject having a demyelinating disease. In some embodiments, the method comprises administering to the subject a therapeutically effective dose of a neurotransmitter receptor modulating agent selected from a muscarinic receptor antagonist, a dopamine receptor antagonist, a histamine receptor antagonist, a beta adrenergic receptor modulator, and an opioid receptor modulator; thereby treating the demyelinating disease.

In yet another aspect, the present invention provides for methods of enhancing the therapeutic effect of an immunomodulatory agent in a subject in need thereof. In some embodiments, the method comprises administering to the subject the immunomodulatory agent and a neurotransmitter receptor modulating agent; thereby enhancing the therapeutic effect of the immunomodulatory agent.

In some embodiments, the neurotransmitter receptor modulating agent is a muscarinic receptor antagonist. In some embodiments, the muscarinic receptor antagonist is a muscarinic receptor modulator compound listed in Table 1. In some embodiments, the muscarinic receptor is selected from benztropine, carbetapentane, clemastine, ipratropium, atropine, and salts thereof.

In some embodiments, the neurotransmitter receptor modulating agent is a dopamine receptor antagonist. In some embodiments, the dopamine receptor antagonist is a dopamine receptor modulator compound listed in Table 1. In some embodiments, the dopamine receptor antagonist is selected from benztropine, GBR12935, trifluoperazine, and salts thereof.

In some embodiments, the neurotransmitter receptor modulating agent is a histamine receptor antagonist. In some embodiments, the histamine receptor antagonist is a histamine receptor modulator compound listed in Table 1. In some embodiments, the histamine receptor antagonist is clemastine or a salt thereof.

In some embodiments, the neurotransmitter receptor modulating agent is a beta adrenergic receptor modulator. In some embodiments, the beta adrenergic receptor modulator is a beta adrenergic receptor modulator compound listed in Table 1. In some embodiments, the beta adrenergic receptor modulator is selected from pindolol, salmeterol, salbutamol, albuterol, and salts thereof.

In some embodiments, the neurotransmitter receptor modulating agent is an opioid receptor modulator. In some embodiments, the opioid receptor modulator is an opioid receptor modulator compound listed in Table 1. In some embodiments, the opioid receptor modulator is carbetapentane, Snc-80, BD-1047, or salts thereof.

In some embodiments, the neurotransmitter receptor modulating agent is benztropine, carbetapentane, clemastine, pindolol, ipratropium, atropine, GBR12935, Snc-80, BD-1047, salmeterol, albuterol, trifluoperazine, or a salt thereof. In some embodiments, the neurotransmitter receptor modulating agent is benztropine, clemastine, salmeterol, salbutamol, trifluoperazine, or a salt thereof. In some embodiments, the neurotransmitter receptor modulating agent is benztropine or a salt thereof (e.g., benztropine mesylate).

In some embodiments, the subject has a demyelinating disease. In some embodiments, the demyelinating disease is multiple sclerosis, idiopathic inflammatory demyelinating disease, transverse myelitis, Devic's disease, progressive multifocal leukoencephalopathy, optic neuritis, leukoystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or human T-cell lymphotropic virus (HTLV)-associated myelopathy. In some embodiments, the demyelinating disease is multiple sclerosis. In some embodiments, the demyelinating disease is relapsing-remitting multiple sclerosis (RRMS). In some embodiments, the demyelinating disease is secondary progressive multiple sclerosis (SPMS). In some embodiments, the demyelinating disease is primary progressive multiple sclerosis (PPMS). In some embodiments, the demyelinating disease is progressive relapsing multiple sclerosis (PRMS).

In some embodiments, the subject is a human. In some embodiments, the subject is a non-human mammal.

In some embodiments, the method further comprises administering to the subject an immunomodulatory agent. In some embodiments, the immunomodulatory agent is fingolimod (FTY720), interferon beta-1a, interferon beta-1b, glatiramer acetate, mitoxantrone, or natalizumab. In some embodiments, the immunomodulatory agent is fingolimod (FTY720), interferon beta-1a, or interferon beta-1b.

In some embodiments, the method comprises administering to the subject a therapeutically effective or optimal dose of one or both of the neurotransmitter receptor modulating agent and the immunomodulatory agent. In some embodiments, the method comprises administering to the subject a subtherapeutic dose of one or both of the neurotransmitter receptor modulating agent and the immunomodulatory agent. In some embodiments, the method comprises administering to the subject a therapeutically effective dose or optimal dose of the neurotransmitter receptor modulating agent and a subtherapeutic dose of the immunomodulatory agent. In some embodiments, the method comprises administering to the subject a therapeutically effective dose or optimal dose of the immunomodulatory agent and a subtherapeutic dose of the neurotransmitter receptor modulating agent.

In some embodiments, the method comprises administering one or both of the neurotransmitter receptor modulating agent and the immunomodulatory agent systemically. In some embodiments, the method comprises administering the neurotransmitter receptor modulating agent and the immunomodulatory agent sequentially. In some embodiments, the method comprises administering the neurotransmitter receptor modulating agent concurrently.

In another aspect, the present invention provides for compositions for use in treating a subject having a demyelinating disease. In some embodiments, the composition comprises:
 a neurotransmitter receptor modulating agent; and
 an immunomodulatory agent.

In yet another aspect, the present invention provides for kits for use in treating a subject having a demyelinating disease. In some embodiments, the composition comprises:
 a neurotransmitter receptor modulating agent; and
 an immunomodulatory agent.

In some embodiments, the composition or kit comprises a neurotransmitter receptor modulating agent as described herein and an immunomodulatory agent as described herein. In some embodiments, the neurotransmitter receptor modulating agent is selected from a muscarinic receptor antagonist, a dopamine receptor antagonist, a histamine receptor antagonist, a beta adrenergic receptor modulator, and an opioid receptor modulator. In some embodiments, the neurotransmitter receptor modulating agent is benztropine, clemastine, salmeterol, salbutamol, trifluoperazine, or a salt thereof. In some embodiments, the neurotransmitter receptor modulating agent is benztropine or a salt thereof. In some embodiments, the immunomodulatory agent is fingolimod (FTY720), interferon beta-1a, interferon beta-1b, glatiramer acetate, mitoxantrone, or natalizumab. In some embodiments, the neurotransmitter receptor modulating agent is benztropine, clemastine, salmeterol, salbutamol, trifluoperazine, or a salt thereof and the immunomodulatory agent is fingolimod (FTY720), interferon beta-1a, or interferon beta-1b.

In some embodiments, the neurotransmitter receptor modulating agent is formulated as a therapeutically effective or optimal dose and the immunomodulatory agent is formulated as a therapeutically effective or optimal dose. In some embodiments, the neurotransmitter receptor modulating agent is formulated as a therapeutically effective or optimal dose and the immunomodulatory agent is formulated as a subtherapeutic dose. In some embodiments, the immunomodulatory agent is formulated as a therapeutically effective or optimal dose and the neurotransmitter receptor modulating agent is formulated as a subtherapeutic dose. In some embodiments, the neurotransmitter receptor modulating agent is formulated as a subtherapeutic dose and the immunomodulatory agent is formulated as a subtherapeutic dose.

In yet another aspect, the present invention also provides for use of a composition as described herein for the manufacture of a medicament for the treatment of a demyelinating disease.

DEFINITIONS

As used herein, the term "neurotransmitter receptor modulating agent" refers to an agent that inhibits or activates the activity of a neurotransmitter receptor. In some embodiments, the term refers to a compound that modulates the activity of a muscarinic receptor (e.g., a muscarinic receptor antagonist), a dopamine receptor (e.g., a dopamine receptor antagonist), a histamine receptor (e.g., a histamine receptor antagonist), a beta adrenergic receptor (e.g., a beta adrenergic receptor antagonist), or an opioid receptor (e.g., an opioid receptor modulator). For any compound that is identified as a neurotransmitter receptor modulating agent (e.g., a compound described in Table 1 herein), it is also contemplated that any pharmaceutically acceptable salts, prodrugs, racemic mixtures, conformational and/or optical isomers, crystalline polymorphs and isotopic variants of the compound may also be used. In some embodiments, the neurotransmitter receptor modulating agent is a small molecule, e.g., a molecule having a molecular weight of less than 800 kDa. In some embodiments, the neurotransmitter receptor modulating agent is a small molecule that is able to cross the blood-brain barrier.

As used herein, the term "oligodendrocyte precursor cell" or "OPC" refers to an undifferentiated progenitor cell with the capacity to self-renew and differentiate into a myelinating oligodendrocyte. A "mature myelinating cell fate" refers to cell that is capable of forming myelin, e.g., a myelinating oligodendrocyte. "Differentiation" refers to the process by which a specialized cell type is formed from a less specialized cell type, for example, a myelinating oligodendrocyte from an OPC. In some embodiments, an OPC is identified by morphology and/or by the presence of a biomarker, e.g., PDGFR-α or NG2. In some embodiments, a myelinating oligodendrocyte is identified by morphology and/or by the presence of a marker, e.g., myelin basic protein (MBP), myelin oligodendrocyte glycoprotein (MOG), 2'3'-cyclic-nucleotide 3' phosphodiesterase (CNP), galactocebroside (GalC), O1 antigen (O1), or O4 antigen (O4).

As used herein, the terms "stimulating increased myelination" or "stimulate increased myelination" refer to inducing an increased amount of myelin surrounding an axon, e.g., by administering an agent that induces the differentiation of oligodendrocyte precursor cells to a mature myelinating cell fate, as compared to the amount of myelin surrounding the axon in the absence of the agent being administered. In some embodiments, an agent stimulates "increased" myelination when the amount of myelin surrounding the axon in a sample (e.g., a brain tissue sample from a subject having a demyelinating disease) subsequent to administration of an agent that induces the differentiation of OPCs to a mature myelinating cell fate is at least about 5%, 10%, 15%, 20%, 30%, 40%, 50%, 60%, 70%, 80%, 90%, or more as compared to the amount of myelin surrounding the axon in the sample prior to administration of the agent. The amount of myelin surrounding an axon can be measured by any method known in the art, e.g., using magnetic resonance imaging (MRI). In some embodiments, an agent stimulates increased myelination when one or more characteristics of a demyelinating disease (e.g., multiple sclerosis) improves subsequent to administration of an agent that induces differentiation of OPCs to a mature myelinating cell fate as compared to the characteristic of the diseases prior to administration of the agent. As a non-limiting example, an agent is said to stimulate increased myelination in a subject having multiple sclerosis when the frequency and/or severity of inflammatory attacks decreases subsequent to administration of an agent as compared to the frequency and/or severity of inflammatory attacks prior to administration of the agent.

As used herein, the term "demyelinating disease" refers to a disease or condition of the nervous system characterized by damage to or loss of the myelin sheath of neurons. A demyelinating disease can be a disease affecting the central nervous system or a disease affecting the peripheral nervous system. Examples of demyelinating diseases include, but are not limited to, multiple sclerosis, idiopathic inflammatory demyelinating disease, transverse myelitis, Devic's disease, progressive multifocal leukoencephalopathy, optic neuritis, leukoystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or HTLV-associated myelopathy. In some embodiments, the demyelinating disease is multiple sclerosis.

As used herein, the term "subject" refers to animals such as mammals, including, but not limited to, primates (e.g., humans), cows, sheep, goats, horses, dogs, cats, rabbits, rats, mice and the like. In some embodiments, the subject is a human.

As used herein, the term "compound" refers to any molecule, either naturally occurring or synthetic, e.g., peptide, protein, oligopeptide (e.g., from about 5 to about 50 amino acids in length), small organic molecule, polysaccharide, peptide, circular peptide, peptidomimetic, lipid, fatty acid, siRNA, polynucleotide, oligonucleotide, etc., to be tested for the capacity to induce OPC differentiation. The compound to be tested can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, compounds are screened by identifying a test compound (called a "screening hit") with some desirable property or activity, e.g., inducing activity, and screening hits are confirmed and validated using in vitro and in vivo assays. Often, high throughput screening (HTS) methods are employed for such an analysis.

An "agonist" refers to an agent that stimulates, increases, activates, or enhances activation of a neurotransmitter receptor (e.g., muscarinic receptor, dopamine receptor, histamine receptor, beta adrenergic receptor, and/or opioid receptor) of the invention.

An "antagonist" refers to an agent that partially or totally blocks stimulation, decreases, prevents, inactivates, or delays activation of a neurotransmitter receptor (e.g., muscarinic receptor, dopamine receptor, histamine receptor, beta adrenergic receptor, and/or opioid receptor) of the invention.

As used herein, the terms "therapeutically effective amount or dose" or "therapeutically sufficient amount or dose" or "effective or sufficient amount or dose" refer to a dose that produces therapeutic effects for which it is administered when it is administered on its own. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the terms "administer" or "administering" refer to any type of administration, including but not limited to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the terms "treat" or "treating" or "treatment" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subtherapeutic dose" refers to a dose of a pharmacologically active agent(s), either as an administered dose of pharmacologically active agent, or actual level of pharmacologically active agent in a subject, that functionally is insufficient to elicit the intended pharmacological effect in itself, or that quantitatively is less than the established therapeutic dose for that particular pharmacological agent (e.g., as published in a reference consulted by a person of skill, for example, doses for a pharmacological agent published in the Physicians' Desk Reference, 66th Ed., 2012, PDR Network, LLC; or Brunton, et al., Goodman & Gilman's The Pharmacological Basis of Therapeutics, 12th edition, 2011, McGraw-Hill Professional) when administered on its own. A "subtherapeutic dose" can be defined in relative terms (i.e., as a percentage amount (less than 100%) of the amount of pharmacologically active agent conventionally administered). For example, a subtherapeutic dose can be about 1% to about 75% of the amount of pharmacologically active agent conventionally administered. In some embodiments, a subtherapeutic dose can be about 75%, 50%, 30%, 25%, 20%, 10% or less, of the amount of pharmacologically active agent conventionally administered.

BRIEF DESCRIPTION OF THE DRAWINGS

FIG. 1A-C. Neurotransmitter receptor modulating agents dose dependently induce OPC differentiation. (A) Chemical structures of representative identified OPC differentiating molecules. The calculated $EC_{50}$ values were determined using appropriate Graphpad Prism 5.0 curve fitting software. (B) Dose dependent compound induced OPC differentiation. OPCs were plated in 384 well plates at 1000 cells per well in OPC media containing basal PDGF-αα (2 ng/mL) and treated with serial dilutions of compounds. Following six days of compound treatment, cells were fixed and subjected to immunofluorescence analysis using anti-myelin basic protein (MBP) antibody. Image acquisition and quantification of MBP staining was performed using the OPERA imaging system. (C) Maximal OPC differentiation inducing activity of identified compounds compared to DMSO control.

FIG. 2A-C. Neurotransmitter receptor modulating agents induce the differentiation of OPCs to a myelinating oligodendrocyte cell fate. (A) Western blot analysis of OPCs treated with compounds at $EC_{90}$ concentrations for 6 days. Total protein was isolated from cell pellets and probed for myelin basic protein (MBP) and myelin oligodendrocyte glycoprotein (MOG) using specific antibodies. (B-C) Quantitative RT-PCR (qRT-PCR) analysis of OPCs treated with compounds at $EC_{90}$ concentrations for 6 days. Total RNA was isolated from cell pellets and reverse transcribed. MBP and MOG expression was quantified using specific probes and Taqman-based qRT-PCR. Expression was normalized to the internal controls (β-actin and GAPDH. Fold change in gene expression over DMSO treated control cells is plotted for MBP (B) and MOG (C). Results are displayed as mean+/−standard deviation, n=3.

FIG. 5A-E. Representative neurotransmitter receptor modulating agents benzatropine and trifluoperazine ameliorate symptoms in a PLP induced relapsing EAE mouse model. (A-E) SJL mice were immunized with proteolipid peptide (PLP) and pertussis toxin and monitored daily with scoring on the standard clinical EAE scale (0-5). Compounds were administered daily for the duration of the study in saline at 10 mg/kg via intra-peritoneal injection (0.1 ml), starting on the day of the appearance of clinical EAE symptoms (day 10). Sub-optimal dosing of mycophenolate mofetil at 20 mg/kg in sterile saline (pH 5) was administered in combination with benzatropine and trifluoperazine respectively, starting on the day of peak clinical EAE symptoms (day 14) post PLP injection. Mean clinical EAE score and standard error of mean (SEM) are shown for each study group. Mice in the vehicle control group, n=6 (open boxes) show appearance of acute phase (mean maximal clinical EAE score of 2±0.8 on day 11) followed by remission (mean maximal clinical EAE score of 0.3±0.3 on day 19) and relapse of EAE symptoms (mean maximal clinical EAE score of 1.5±0.4 on day 25). (A) Mycophenolate mofetil, n=6 (closed boxes) shows partial reduction in the severity of relapse (mean maximal EAE score 0.7±0.3 on day 25, p value<0.05). (B, D) Benzatropine, n=5 ((B), closed boxes) and trifluoperazine, n=6 ((D), closed boxes) show a significant reduction in the severity of relapse (mean maximal clinical EAE score 0.2±0.2 (day 25) and 0.4±0.4 (day 26) respectively, p values<0.001). (C, E) Benzatropine in combination with mycophenolate mofetil (C) and trifluoperazine in combination with mycophenolate mofetil (E) n=6 for both (closed boxes) show complete suppression of relapse (mean maximal clinical EAE score 0±0 for both on day 25, p values<0.001).

FIG. 6A-B. Muscarinic receptor antagonism induces OPC differentiation but is not the sole pharmacological mechanism of all identified differentiation inducing agents. (A) The muscarinic receptor agonist carbachol antagonizes compound induced OPC differentiation in some cases. OPCs were plated in 384-well plates at 1000 cells per well in media containing compounds at $EC_{90}$ concentrations and treated with 1:3 serial dilutions of carbachol. Following 6 days of treatment, cells were fixed and stained for MBP. Plates were imaged using the OPERA high content screening system and MBP staining was quantified as described. Carbachol treatment results in dose dependent inhibition of the differentiation activity of benzatropine, carbapentane and clemastine, while no effect is observed on the differentiation activity of salmeterol, GBR12935 and trifluoperazine. (B) Carbachol-induced calcium ($Ca^{2+}$) influx is blocked by the muscarinic receptor antagonist activity of some compounds. OPCs were plated in 384-well plates at 5000 cells per well in media containing basal PDGF-αα. Cells were equilibrated with $Ca^{2+}$ sensitive Fluo-3AM® dye in HBSS for 30 min. Multiple concentrations of OPC differentiation-inducing compounds (3 times the $EC_{90}$, $EC_{90}$ and $EC_{50}$) were added followed by addition of 1:3 serial dilutions of the muscarinic receptor agonist Carbachol. $Ca^{2+}$ influx was immediately measured using the FLIPR TETRA® system. Shown are representative data for carbachol treatment at 100 uM and compound treatment at $EC_{90}$. Relative light units (RLU) indicating $Ca^{2+}$ influx are plotted on the y-axis and time (in sec) after addition of carbachol plotted on the x-axis. GBR12935, trifluoperazine, and salmeterol (top) show no effect on carbachol induced $Ca^{2+}$ influx while clemastine, benzatropine, and carbapentane (bottom) inhibit $Ca^{2+}$ influx induced by carbachol.

FIG. 7A-C. A high throughput screen identified muscarinic receptor antagonist benztropine as an inducer of OPC differentiation. (A) Benztropine [1.5 uM] and positive control thyroid hormone [1 uM] treated rat OPCs were cultured under basal differentiation conditions (2 ng/ml PDGF) for 6 days and stained for MBP (green). The structure of benztropine is also shown. (B) Benztropine [1.5 uM] treated OPCs were analyzed for MBP and MOG expression after 6 days in culture using qRT-PCR. (C) OPCs were co-treated with benztropine [2.3 uM] and carbachol [0 uM, 0.6 uM and 4.7 uM] for 6 days under basal differentiation conditions and stained for MBP.

FIG. 8A-C. Benztropine decreases the clinical severity of disease in the PLP induced EAE model for MS. (A) Benztropine decreased the clinical severity of disease in the PLP induced EAE model when dosed prophylactically (starting on the day of PLP injection) as well as therapeutically (at the start of EAE symptoms) and showed efficacy comparable to FTY720 (1 mg/kg) and interferon-β (10,000 U/mouse). (B) Quantification of confocal images of spinal cord sections from EAE mice treated with benztropine and stained with specific antibodies for GST-π (a marker of mature oligodendrocytes) and NG2 (a marker of OPCs) showed increased GST-π positive cells as compared to vehicle treated mice, with no change in the number of NG2 positive cells. (C) Representative confocal images of spinal cord sections from EAE mice treated with benztropine and stained with specific antibodies for GST-π (mature oligodendrocytes) and NG2 (OPCs).

FIG. 9A-B. Benztropine treatment induces remyelination in vivo in the cuprizone model. (A) Representative images from the corpus callosum region of the brain at various time points show increased remyelination observed in benzatropine treated mice as compared to vehicle treated mice 2 weeks after cuprizone withdrawal and commencement of drug administration. (B) Quantification of the myelinated areas in the corpus callosum region shows a significant (~2-fold) increase in myelin staining in benztropine treated mice as compared vehicle controls 2 weeks after drug treatment. Data is represented in terms of threshold bins on the grey scale (0-50) as described. Error bars represent standard deviations of at least 6 corpus callosum regions.

FIG. 10A-F. Combination with benztropine improves efficacy and allows for a reduction in the dose of FTY720 and interferon-β. (A) Clinical EAE scores for mice treated with FTY720 (1 mg/kg) in combination with benztropine (BA; 2.5 mg/kg) show a significantly decreased clinical severity as compared to mice treated with FTY720 (1 mg/kg) or benztropine (2.5 mg/kg) alone. (B) Clinical EAE scores for mice treated with Interferon-β (IFN; 10,000 U/mouse) in combination with benztropine (BA, 2.5 mg/kg) show a significantly decreased clinical severity as compared to mice treated with Interferon-γ (IFN; 10,000 U/mouse) or Benztropine (2.5 mg/kg) alone. (C) Clinical EAE scores for mice treated with FTY720 (0.1 mg/kg) or FTY720 (0.1 mg/kg) or benztropine (BA; 2.5 mg/kg). (D) Clinical EAE scores for mice treated with interferon-β (IFN; 3000 U/mouse) or interferon-β (IFN; 10,000 U/mouse) or benztropine (BA; 2.5 mg/kg). (E) Clinical EAE scores for mice treated with FTY720 (0.1 mg/kg) in combination with benztropine (BA; 2.5 mg/kg) show a comparable decrease in clinical severity scores as compared to FTY720 (1 mg/kg), facilitating the reduction in the dose of FTY720. (F) Clinical EAE scores for mice treated with interferon-β (IFN; 3000 U/mouse) in combination with benztropine (BA; 2.5 mg/kg) do not show a comparable decrease in clinical severity scores as interferon-β (IFN; 10,000 U/mouse). Error bars indicate standard deviation of the mean within each group of 8 mice.

FIG. 11A-B. Screen to identify inducers of OPC differentiation. (A) OPCs were maintained as proliferating A2B5-positive cells under basal growth conditions (Neurobasal medium, B27 supplement without Vitamin A, non-essential amino acids, L-Glutamine, 30 ng/ml PDGF). OPCs were plated in basal differentiation media (Neurobasal medium, B27 supplement without Vitamin A, non-essential amino acids, L-Glutamine, 2 ng/ml PDGF), treated with DMSO (<0.1%) or thyroid hormone (1 uM), fixed after 6 days in culture, and stained using antibodies for CNP, O4, or MBP. A2B5-positive OPCs differentiate into immature oligodendrocytes that express CNP and O4, but not MBP, upon withdrawal of PDGF. Addition of thyroid hormone induces the differentiation of OPCs into mature oligodendrocytes that express MBP. (B) Screen strategy using A2B5 positive OPCs cultured under basal differentiation conditions and treated with compounds for 6 days to identify small molecules that induce the differentiation of OPCs to mature, MBP expressing oligodendrocytes.

FIG. 12A-B. Primary hit confirmation. (A) Dose response assay used to confirm primary screening hits and determine potency ($EC_{50}$). ($EC_{50}$) is defined as the concentration that results in a half maximal increase in the percentage of total cells that express MBP as detected by immunostaining. OPCs were cultured in differentiation medium and treated with benztropine or control (DMSO<0.01%) for 6 days. Cells were fixed and immunostained using antibodies for MBP. Error bars represent standard deviations from 3 replicate experiments. (B) Representative images show dose dependent activity of benztropine.

FIG. 16A-B. Gene expression profiles of benztropine treated cells show a downregulation of OPC genes and an upregulation of mature oligodendrocyte genes. (A) Increased expression (fold change) of mature oligodendrocyte genes in compound treated cells as compared to DMSO treated cells. (B) Decreased expression (fold change) of OPC genes in compound treated cells as compared to DMSO treated cells.

FIG. 17A-D. Timing of compound treatment determines the efficiency of differentiation. (A) OPCs were plated in differentiation medium on day 0 and treated with compounds on various days. Cells were fixed and immunostained for MBP on day 6 after plating. (B) OPCs were plated in differentiation medium on day 0 and treated with compounds 12 hours later. Cells were fixed on various days following compound treatment and immunostained for MBP. (C) Treatment with benztropine within 48 hours of plating in differentiation medium induced efficient differentiation of OPCs to mature oligodendrocytes. Compound treatment 72 hours or more after plating in differentiation medium reduced the efficiency of differentiation of OPCs. (D) Benztropine treatment for a minimum of 5 days was necessary to induce efficient differentiation of OPCs to mature oligodendrocytes.

FIG. 19A-B. Benztropine has no effect on histamine receptor signaling. OPCs were plated in basal differentiation medium (Neurobasal medium, B27 supplement without Vitamin A, non-essential amino acids, L-Glutamine, 2 ng/ml PDGF) and co-treated with various concentrations of benztropine and (A) histamine or (B) the histamine receptor agonist histamine trifluoromethyltoluidide (HTMT).

FIG. 20A-B. Benztropine has no effect on dopamine D2 and D3 receptor signaling. OPCs plated in basal differentiation medium (Neurobasal medium, B27 supplement without Vitamin A, non-essential amino acids, L-Glutamine, 2 ng/ml PDGF) and co-treated with various concentrations of benztropine and the dopamine receptor (A) agonist quinpirole or (B) antagonist haloperidol. Error bars indicate standard deviations of 3 replicate measurements.

FIG. 24A-D. Benztropine antagonizes the $M_1/M_3$ muscarinic receptors but not the $M_2/M_4$ muscarinic receptors. (A-C) OPCs were plated in differentiation media for 12 hours. Media was changed to Hank's Balanced Salt Solution (HBSS) with 4-(2-hydroxyethyl)-1-piperazineethanesulfonic acid (HEPES) and cells were treated with benztropine at various concentrations for 1 hour. Carbachol was added and calcium flux was measured for 186 seconds using the FLIPR TETRA® system. (A) Carbachol induced a dose dependent increase in intracellular $Ca^{2+}$ levels. (B) Benztropine dose dependently blocked carbachol induced calcium influx through antagonism of $M_1/M_3$ muscarinic receptors. (C) Atropine, a muscarinic antagonist, serves as a positive control. (D) OPCs were plated in differentiation medium for 12 hours. A cAMP-HTRF assay was performed using the cAMP dynamic 2 kit. Benztropine had no effect on the levels of cAMP. IBMX was added as a cAMP stabilizer, and forskolin was a positive control.

FIG. 27A-F. Benztropine has no effect on T-cell activation and proliferation in vitro. (A-F) Total splenocytes were isolated from mice and stimulated with CD3 and analyzed by flow cytometry for expression of T-cell activation markers CD69 and CD25 and T-cell proliferation using CFSE. (A) Unstimulated cells. (B) DMSO treated cells. (C) Mycophenolate suppresses the activation and proliferation of T-cells as compared to DMSO. (D) Benztropine has no effect on T-cell activation. (E) Mycophenolate suppresses T-cell proliferation. (F) Benztropine has no effect on T-cell proliferation. The numbers represent percentage gated populations positive for the given marker.

FIG. 28A-K. Benztropine shows no immunosuppressive effects in vivo after induction of EAE in mice. (A-K) EAE was induced in mice by injecting PLP and pertussis toxin. Benztropine (10 mg/kg) and saline (vehicle control) were injected intraperitoneally in the therapeutic mode for 14 days. Total splenocytes were isolated from the mice, stimulated with PMA and ionomycin, and analyzed for various populations of immune cells and cytokine secretion after 48 hours. Protein transport was blocked in cells used for cytokine analysis using Monoeiosin. Benztropine treatment had no effect on the number of total splenocytes (A), number of B cells (B), number of CD4$^+$ T-cells (C), number of CD8$^+$ T-cells (D), number of CD4$^+$/CD44Hi T-cells (E), and number of CD8+/CD44Hi T-cells (F). Benztropine also had no effect on cytokine production measured as the number of IL2 producing CD4$^+$ T-cells (G), number of IL10 producing CD4$^+$ T-cells (H), number of TNF-α producing CD4$^+$ T-cells and number of IFN-γ producing CD4$^+$ T-cells. Error bars indicate standard deviation of the mean within each group of 5 mice. Representative flow cytometry scatter plots (K) show similar numbers of CD4$^+$, CD8$^+$, and CD44$^+$ cells in spleens isolated from vehicle treated mice and benztropine treated mice.

FIG. 29A-J. Benztropine shows no immunosuppressive effects in vivo in normal mice. (A-J) Benztropine (10 mg/kg) and saline (vehicle control) were injected intraperitoneally in normal mice for 14 days. Total splenocytes were isolated from the mice, stimulated with PMA and ionomycin and analyzed for various populations of immune cells and cytokine secretion after 48 hrs. Protein transport was blocked in cells used for cytokine analysis using monoeiosin. Benztropine treatment had no effect on the number of total splenocytes (A), number of B cells (B), number of CD4$^+$ T-cells (C), number of CD8$^+$ T-cells (D), number of CD4$^+$/CD44Hi T-cells (E) and number of CD8+/CD44Hi T-cells (F). Benztropine also had no effect on cytokine production measured as the number of IL2 producing CD4$^+$ T-cells (G), number of IL10 producing CD4$^+$ T-cells (H), number of TNF-γ producing CD4$^+$ T-cells (I) and number of IFN-γ producing CD4$^+$ T-cells (J). Error bars indicate standard deviation of the mean within each group of 5 mice.

FIG. 30A-F. Benztropine does not suppress T-cell dependent and independent immune responses. (A-F) Mice were injected with Keyhole Limpet Hemocyanin protein conjugated to 2,4,6, trinitrophenylhapten (TNP-KLH), lipopolysaccharide conjugated to 2,4,6, trinitrophenylhapten (TNP-LPS), or TNP (2,4,6-Trinitrophenyl)-FICOLL conjugate (TNP-Ficoll) in appropriate adjuvants and treated with vehicle or benztropine (10 mg/kg). Serum was isolated at various time points and IgG and IgM levels were measured by ELISA. (A, B) Benztropine showed no effect on TNP-LPS induced T-cell independent B-cell responses measured as serum IgM and IgG levels. (C, D) Benztropine showed no effect on TNP-Ficoll induced T-cell independent B-cell responses measured as serum IgM and IgG levels. (E, F) Benztropine showed no effect on TNP-KLH induced T-cell dependent B-cell responses measured as serum IgM and IgG levels. Error bars represent standard deviations from 3 replicate ELISAs performed on samples from 5 mice in each treatment group.

FIG. 31A-D. Quantification of myelination staining in the cuprizone model. (A) Luxol Fast Blue staining was performed on sections from the corpus callosum region of the brains isolated from mice treated either with benztropine (10 mg/kg) or vehicle control after 7 weeks of exposure to cuprizone. (B) Images were converted to a 256 shade grey scale. (C) The 256 shades of grey were divided into 5 bins of 50 shades each. Number of objects in the corpus callosum region in each bin were counted using Image-Pro plus. (D) Representative images of Image-Pro rendering of the quantification of objects in each bin.

FIG. 33A-F. Combination with benztropine improves efficacy and allows for a reduction in the dose of FTY720 and interferon-β. (A-F) EAE was induced in mice using PLP and pertussis toxin. Benztropine (2.5 mg/kg) and FTY720 (various doses) and interferon (various does) were injected via intraperitoneal injections in the therapeutic mode at the start of EAE symptoms. (A) Clinical EAE scores for mice treated with FTY720 at doses of 1 mg/kg, 0.1 mg/kg and 0.01 mg/kg show a dose dependent activity for FTY720. (B) Clinical EAE scores for mice treated with interferon-β at doses of 10,000 U, 3000 U and 1000 U per mouse shows a dose dependent activity for interferon-β. (C) Combinations of benztropine (2.5 mg/kg) with FTY720 (1 mg/kg, 0.1 mg/kg and 0.01 mg/kg). (D) Combinations of benztropine (2.5 mg/kg) with interferon-β (10,000 U, 3000 U and 1000 U per mouse). (E) Clinical EAE scores for mice treated with FTY720 (0.01 mg/kg) in combination with benztropine (BA; 2.5 mg/kg) does not show a significantly decreased clinical severity as compared to mice treated with FTY720 (0.01 mg/kg) or benztropine (2.5 mg/kg) alone. (F) Clinical EAE scores for mice treated with interferon-β (IFN; 1000 U/mouse) in combination with benztropine (BA, 2.5 mg/kg) does not show a significantly decreased clinical severity as compared to mice treated with interferon-β (IFN; 1000 U/mouse) or benztropine (2.5 mg/kg) alone. Error bars indicate standard deviation of the mean within each group of 8 mice.

FIG. 34A-F. Identified compounds decrease clinical severity in the EAE model. (A-F) EAE was induced in mice by injecting PLP in complete Freund's adjuvant (CFA) and pertussis toxin, and the animals were scored daily for clinical severity of disease on a scale of 0-5. (A) Clinical EAE scores for mice treated with benztropine (10 mg/kg) in the therapeutic mode (injections starting at the first appearance of EAE symptoms on day 8-10) showed a significantly decreased clinical severity in the relapse phase of the disease as compared to vehicle treated mice. (B) Clinical EAE scores for mice treated with benztropine (10 mg/kg) in the prophylactic mode (injections starting on day 0) showed a significantly decreased clinical severity in both acute and relapse phase of the disease as compared to vehicle treated mice. (C) Benztropine showed a dose dependent efficacy in decreasing clinical severity scores in the EAE model, with 12.5 mg/kg being the most effective dose and 0.1 mg/kg showing no effect. Clinical EAE scores for mice treated with (D) trifluoperazine (10 mg/kg), (E) clemastine (10 mg/kg), or (F) salbutamol (10 mg/kg) in the therapeutic mode showed a significantly decreased clinical severity in the relapse phase of the disease as compared to vehicle treated mice. Error bars indicate standard deviation of the mean within each group of 8-10 mice.

DETAILED DESCRIPTION OF THE INVENTION

I. Introduction

Figure 2A:
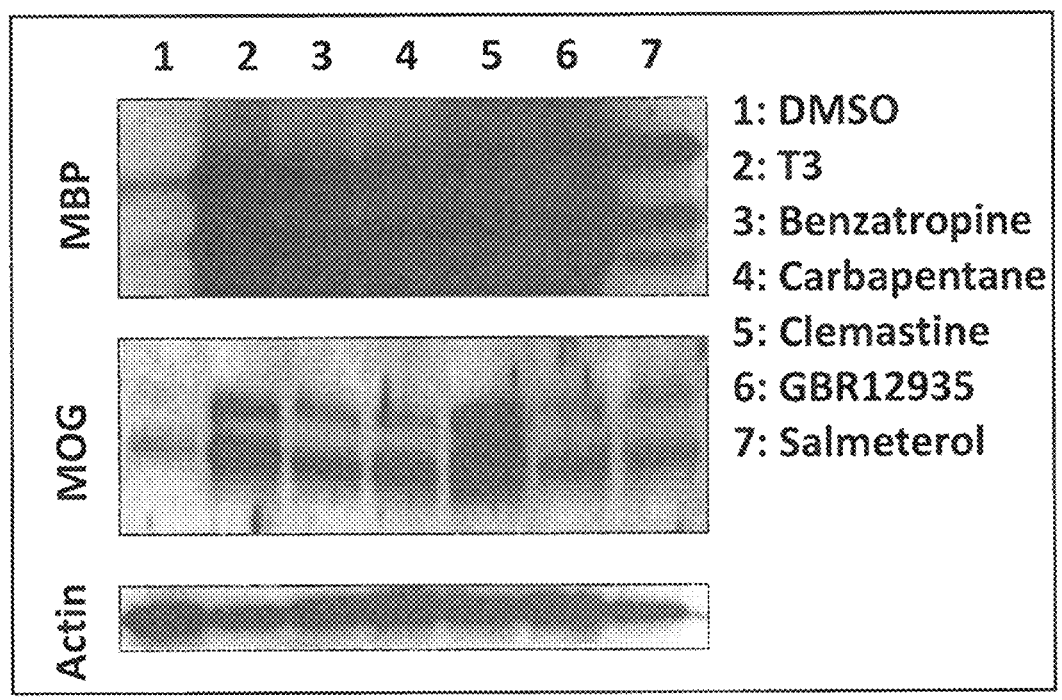

The present invention is based, in part, on the discovery that compounds that modulate various classes of neurotransmitter receptors, such as muscarinic receptor antagonists, dopamine receptor antagonists, histamine receptor antagonists, beta adrenergic receptor antagonists, and opioid receptor modulators, promote the differentiation of oligodendrocyte precursor cells (OPCs) into a mature myelinating cell fate (e.g., myelinating oligodendrocytes). Accordingly, in one aspect, the present invention provides for methods of inducing OPC differentiation to myelinating oligodendrocytes.

Without being bound by a particular theory, it is believed that in demyelinating diseases such as multiple sclerosis, OPCs are present and able to migrate to demyelinated regions, suggesting that the progressive decrease in remyelination in these diseases is not due to defects in OPC population or recruitment, but rather is due to impaired differentiation of OPCs (reviewed in Chong and Chan, *J Cell Biol.* 188:305-312 (2010)). Accordingly, the present invention further provides for methods of stimulating increased myelination of nerves in a subject in need thereof by administering to a subject a neurotransmitter receptor modulating agent, such as a muscarinic receptor antagonist, a dopamine receptor antagonist, a histamine receptor antagonist, a beta adrenergic receptor antagonist, or an opioid receptor modulator. The present invention also provides methods of treating a subject having a demyelinating disease by administering to a subject a neurotransmitter receptor modulating agent.

II. Agents that Stimulate Increased Myelination of Nerves

A. Neurotransmitter Receptor Modulating Agents

A neurotransmitter receptor modulating agent is an agent that induces oligodendrocyte precursor cell (OPC) differentiation to a mature myelinating cell fate (e.g., myelinating oligodendrocytes) and/or stimulates increased myelination. In some embodiments, a neurotransmitter receptor modulating agent is selected from a muscarinic receptor antagonist, a dopamine receptor antagonist, a histamine receptor antagonist, a beta adrenergic receptor modulator, and an opioid receptor modulator. As shown in the Examples section below, exemplary members of each of these classes of compounds has been shown to induce OPC differentiation to a myelinating oligodendrocyte cell fate, and thus stimulate increased myelination. Based on the data showing this activity of exemplary muscarinic receptor antagonists, dopamine receptor antagonists, histamine receptor antagonists, beta adrenergic receptor antagonists, and opioid receptor modulators, other compounds in each of these classes and having similar pharmacological mechanisms to the exemplified compounds, such as the compounds listed in Table 1, are also predicted to be useful for inducing OPC differentiation to a mature myelinating cell fate (e.g., myelinating oligodendrocytes) and/or stimulating increased myelination.

In some embodiments, a compound that is identified as an agent that stimulates increased myelination has "selective" activity for one of these classes of neurotransmitter receptors (i.e., has an agonistic or antagonistic effect against one of a muscarinic receptor, a dopamine receptor, a histamine receptor, a beta adrenergic receptor, or an opioid receptor, or a subtype of any of these receptors, and has a weaker effect or substantially no effect against the other receptors). In some embodiments, a compound that is identified as an agent that stimulates increased myelination has activity against two or more of these classes of neurotransmitter receptors or subtypes of neurotransmitter receptors.

TABLE 1

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| (−)-Norephedrine | | | | • | | | |
| (−)-Quinpirole hydrochloride | | • | | | | | |
| (−)-Terbuclomine | | | | • | | | |
| (+)-Butaclamol | | • | | | | | |
| (+)-BUTACLAMOL HYDROCHLORIDE | | • | | | | | |
| (+−)-Ethylketazocine | | | | | • | | |
| (+)-Lappaconitine | | | | | • | | |
| (+)-Scopolamine | • | | | | | | |
| (+−)-Trimethoquinol | | | | • | | | |
| (+/−)-Epibatidine | | | | | • | | |
| (1r,2r)-cyclohexane-1,2-dicarboxylic acid | | | | | • | | |
| (3,4-dihydroxyphenylamino)-2-imidazoline | | | | • | | | |
| .DELTA.9-Tetrahydrocannabinol | | | | | • | | |
| [11C]MNPA | | • | | | | | |
| 1-((6,7-Dimethoxy-3-methyl-2-benzofuranyl)carbonyl)-4-methylpiperazine monohydrochloride | | • | | | | | |
| 1-(3-bromo-5-isoxazolyl)-2-(tert-butylamino)ethanol hydrochloride | | | | • | | | |
| 1-(3-Chlorophenyl)piperazine | | | | | | | • |
| 1-(3-Chlorophenyl)piperazine dihydrochloride | | | | | | | • |
| 1-(3-Chlorophenyl)piperazine hydrochloride | | | | | | | • |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| 1-(4-Hydroxyphenyl)-2-aminoethanol | | | | • | | | |
| 1,2,9,10-tetramethoxyaporphine | • | | | | | • | |
| 1,4-bis{2-[(4-methoxynaphthalen-1-yl)methylidene]hydrazinyl}phthalazine | • | | | | | | |
| 1,5-Trimethylenetetrazole | | | | | | • | |
| 1-[3-(Trifluoromethyl)phenyl]piperazine | | | | | | | • |
| 121524-08-1 | | | | • | | | |
| 125-71-3 (Parent) | | | | | | • | |
| 127-35-5 | | | | | • | | |
| 17-Hydroxy-2,3-cyclopropanoandrostane | | | | • | | | |
| 19-Propylorvinol | | | | | • | | |
| 1-Benzylimidazole | | | | • | | | |
| 1-M-Thiq | | • | | | | | |
| 1-PHENYLPIPERAZINE | | | | • | | | |
| 1-Propanamine, 3-dibenzo[b,e]thiepin-11(6H)-ylidene-N,N-dimethyl- | | | | • | | | |
| 2-((2-Ethoxyphenoxy)phenylmethyl)morpholine methanesulfonate | | | | • | | | |
| 2-(1-Piperazinyl)pyrimidine | | | | • | | | |
| 2-(2-Aminoethyl)pyridine | | | • | | | | |
| 2-(2-Aminoethyl)pyridine dihydrochloride | | | • | | | | |
| 2-Detpq | | | | | | | • |
| 2-Methoxyidazoxan | | | | • | | | |
| 2-METHYL-1,3-DIOXOLANE | • | | | | | | |
| 2-Thiazoleethanamine | | | • | | | | |
| 3-iodopindolol | | | | • | | | |
| 3-Quinuclidinyl benzilate | • | | | | | | |
| 4-DAMP | • | | | | | | |
| 4-Damp methiodide | • | | | | | | |
| 4-DOI | | | | | | | • |
| 4-NMPB | • | | | | | | |
| 5,6-Dihydroxytryptamine | | | | | | | • |
| 5,7-DIHYDROXYTRYPTAMINE | | | | | | | • |
| 5-Carboxamidotryptamine | | | | | | | • |
| 5-Fhdpat | | | | | | | • |
| 5-Hmdptme | | • | | | | | |
| 5-Hydroxypropafenone | | | | • | | | |
| 5-Methylfurmethide | • | | | | | | |
| 5-Methylurapidil | | | | • | | | |
| 6-Dtaf | | | | | | | • |
| 6-Hydroxydopamine hydrobromide | | | | • | | | |
| 6-Hydroxydopamine hydrochloride | | | | • | | | |
| 6-nitroquipazine | | | | | | | • |
| 76-57-3 | | | | | • | • | |
| 7-Ohdpat | | • | | | | | |
| 87-00-3 | | • | | | | | |
| 8-Artp | | • | | | | | |
| 8-OH-Dpat | | | | | | | • |
| A-38503 | | • | | | | | |
| A-77636 hydrochloride | | • | • | | | | |
| acebutolol | | | | • | | | |
| Acebutolol hydrochloride | | | | • | | | |
| aceclidine | • | | | | | | |
| Aceclidine hydrochloride | • | | | | | | |
| Acepromazine maleate | | • | | | | | |
| Aceroxatidine | | | • | | | | |
| acetaminophen | | | | | | • | |
| Acetylpromazine | | • | | | | | |
| Acide tolfenamique [INN-French] | | | | | | | • |
| ACRIVASTINE | | | • | | | | |
| Actifed | | | • | | | | |
| ACTINOQUINOL SODIUM | | | | • | | | |
| Adobiol | | | | • | | | |
| ADRAFINIL | | | | • | | | |
| Adrenaline bitartrate | | | | • | | | |
| ADTN | | • | | | | | |
| Aerolone | | | | • | | | |
| Aerovent | • | | | | | | |
| Afdx 384 | • | | | | | | |
| AJ 76 | | • | | | | | |
| Aktamin hydrochloride | | | | • | | | |
| Alaproclate | | | | | | | • |
| Alaproclate hydrochloride | | | | | | | • |
| Alesion | | | • | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Aleudrin | | | | • | | | |
| Alfenta | | | | | • | | |
| ALFENTANIL | | | | | • | | |
| Alfentanil hydrochloride | | | | | • | | |
| alfuzosin | | | | • | | | |
| Alginor | • | | | | | | |
| Algolysin | | | | | • | • | |
| Alimezine (TN) | | | • | | | | |
| Allegra | | | • | | | | |
| Allergival | | | • | | | | |
| Allococaine | | • | | | | | |
| Almotriptan | | | | | | | • |
| Alnespiron | | • | | | | | • |
| Alnespirone [INN] | | • | | | | | • |
| Alomide (TN) | | | • | | | | |
| ALOSETRON HYDROCHLORIDE | | | | | | | • |
| Aloxi | | | | | | | • |
| Aloxi (TN) | | | | | | | • |
| alpha-Ergocryptine | | • | | | | | |
| alpha-Methyldopa | | | | • | | | |
| alpha-Methylhistamine | | | • | | | | |
| alpha-Methyl-L-dopa | | | | • | | | |
| alpha-Methylserotonin | | | | | | | • |
| Alphaprodin | | | | | • | | |
| alprenolol | | | | • | | | |
| Alprenolol hydrochloride | | | | • | | | |
| alrestatin | • | | | | | | |
| Altat | | | | • | | | |
| amantadine | | • | • | | • | | |
| Amantadine hydrochloride | | • | • | | • | | |
| Ambenonium chloride | • | | | | | | |
| Amerge | | | | | | | • |
| Amfebutamone | | • | | | | | |
| amfebutamonum | | • | | | | | |
| Amibegron hydrochloride | | | | • | | | |
| amidephrine | | | | • | | | |
| amisulpride | | • | | | | | |
| amitriptyline | | | | | • | • | |
| Amitriptyline hydrochloride | | | | | • | • | |
| Amosulalol | | | | • | | | |
| amosulalol hydrochloride | | | | • | | | |
| amoxapine | | • | | • | | | • |
| Amperozide | | | | | | | • |
| Amperozide hydrochloride | | | | | | | • |
| AMPHETAMINE | | • | | • | | | |
| AMPHETAMINE SULFATE | | • | | • | | | |
| Amsulosin | | | | • | | | |
| Anatran | | • | | | | | |
| Andantol | | | • | | | | |
| Anemet | | | | | | | • |
| anisodamine | • | | | • | | | |
| anisodine | • | | | | | | |
| Anplag | | | | | | | • |
| antazoline | | | • | | | | |
| Antazoline hydrochloride | | | • | | | | |
| Antazoline phosphate | | | • | | | | |
| Antergan | | | • | | | | |
| Antussan | | | | | | • | |
| Anzemet | | | | | | | • |
| apomorphine | • | • | | | | | |
| Apomorphine HCl | • | • | | | | | |
| apraclonidine | | | | • | | | |
| APRACLONIDINE HYDROCHLORIDE | | | | • | | | |
| a-prodine | | | | | • | | |
| Aprofen hydrochloride | • | | | | | | |
| Aprofene | • | | | | | | |
| Ara-putp | • | | | | | | |
| Arbutamina | | | | • | | | |
| ARBUTAMINE | | | | • | | | |
| Arbutamine hydrochloride | | | | • | | | |
| Arc 239 | | | | • | | | |
| arecoline | • | | | | | | |
| Arformoterol | | | | • | | | |
| Arotinolol | | | | • | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| arotinolol hydrochloride | | | | • | | | |
| Artane | • | | | | | | |
| Arterenol bitartrate | | | | • | | | |
| Artex | | | | • | | | |
| Astelin | | | • | | | | |
| astemizole | | | • | | | | |
| Astomin | | | | | | • | |
| Astramorph | | | | | • | | |
| Atarax | | | • | | | | |
| atenolol | | | | • | | | |
| Atipamezole | | | | • | | | |
| Atomoxetine | | | | • | | | |
| ATROPINE | • | | | | | | |
| Atropine iodomethylate | • | | | | | | |
| Atropine methyl nitrate | • | | | | | | |
| Atropine sulfate | • | | | | | | |
| Atrovent | • | | | | | | |
| Auteral | | | • | | | | |
| Avacan | • | | | | | | |
| Avapyrazone | • | | | | | | |
| Avinza | | | | | • | | |
| Axert | | | | | | | • |
| Azaperone | | • | | | | | |
| AZATADINE | | | • | | | | |
| azelastine | | | • | | | | |
| Azepexole | | | | • | | | |
| Azepexole hydrochloride | | | | • | | | |
| Bamipine | | | • | | | | |
| Banistyl | | | • | | | | |
| Banthine | • | | | | | | |
| Batebulast | | | • | | | | |
| Batebulast hydrochloride | | | • | | | | |
| BD1047 | | | | | • | | |
| BE 2254 | | | | • | | | |
| Beforal | | | | | • | • | |
| Befunolol | | | | • | | | |
| Beldavrin | • | | | | | | |
| Bemesetron | • | | | • | | | • |
| BENACTYZINE | • | | | | | | |
| Benactyzine hydrochloride | • | | | | | | |
| benalfocin | | | | • | | | |
| Benextramine | | | | • | | | |
| Benfuran | | | | • | | | |
| Benoxathian | | | | • | | | |
| Benoxathian hydrochloride | | | | • | | | |
| BENPERIDOL | | • | | | | | |
| benserazide | | • | • | | | | |
| Bentanidol | | | | • | | | |
| Benzetimide | • | | | | | | |
| BENZETIMIDE HYDROCHLORIDE | • | | | | | | |
| Benzfetamine | | • | | • | | | |
| Benzhexol | • | | | | | | |
| Benzonatate | | | | | | • | |
| benzphetamine | | • | | • | | | |
| benztropine | • | • | | | | | |
| Benztropinum | • | • | | | | | |
| Berachin | | | | • | | | |
| beta-Cft | | • | | | | | |
| beta-ENDORPHIN | | | | | • | | |
| beta-Endorphin (1-31) | | | | | • | | |
| beta-Flupenthixol | | • | | | | | |
| betahistine | | | • | | | | |
| Betahistine dihydrochloride | | | • | | | | |
| Betahistine mesilate | | | • | | | | |
| betaxolol | | | | • | | | |
| Betaxolol hydrochloride | | | | • | | | |
| BETAZOLE | | | • | | | | |
| Betazole hydrochloride | | | • | | | | |
| bethanechol | • | | | | | | |
| Bethanechol chloride | • | | | | | | |
| Bethanidine | | | | • | | | |
| BINOSPIRONE MESYLATE | | | | | | | • |
| biperiden | • | | | | | | |
| Biperiden hydrochloride | • | | | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Bisguanidinium phosphate | • | | | | | | |
| BISOPROLOL | | | | • | | | |
| Bisoprolol fumarate | | | | • | | | |
| Bitolterol | | | | • | | | |
| Bladderon | • | | | | | | |
| Bmy-7378 | | | | • | | | |
| Bonamine | | | • | | | | |
| BOPINDOLOL | | | | • | | | |
| Bornaprine | • | | | | | | |
| BrAAM | | | | • | | | |
| Bretylium tosylate | | | | • | | | |
| brimonidine | | | | • | | | |
| Brl 15572 | | | | | | | • |
| Brl 26830 | | | | • | | | |
| Brl 37344A | | | | • | | | |
| Brl 48553 | | | | • | | | |
| Brl-15572 | | | | | | | • |
| Brl35135A | | | | • | | | |
| Brocadisipal | | • | | | | | |
| Brolamfetamine | | | | | | | • |
| bromocriptine | | • | | | | | |
| bromopride | | • | | | | | |
| Bromopride hydrochloride | | • | | | | | |
| BROMPHENIRAMINE | | | • | | | | |
| Brompheniramine maleate | | | • | | | | |
| Broncaspin | | | | | | • | |
| Bronitin Mist | | | | • | | | |
| Bronkometer | | | | • | | | |
| Broxaterol | | | | • | | | |
| BTCP | | • | | | | | |
| Buccastem | | • | • | | | | |
| Bucindolol | | | | • | | | |
| Bucindolol hydrochloride | | | | • | | | |
| Buclizine | | | • | | | | |
| Buclodin | | | • | | | | |
| Budipine | • | | | | | | |
| Budipine hydrochloride | • | | | | | | |
| Bufetolol | | | | • | | | |
| Bufotenine | | | | | | | • |
| Bufuralol | | | | • | | | |
| Bunazosin | | | | • | | | |
| Bunolol | | | | • | | | |
| Bunolol hydrochloride | | | | • | | | |
| BUPRANOLOL | | | | • | | | |
| bupranolol hydrochloride | | | | • | | | |
| Buprenorfina [INN-Spanish] | | | | | • | | |
| buprenorphine | | | | | • | | |
| BUPRENORPHINE HYDROCHLORIDE | | | | | • | | |
| Buprenorphine hydrochloride solution | | | | | • | | |
| bupropion | | • | | | | | |
| Bupropion hydrochloride | | • | | | | | |
| BURIMAMIDE | | | • | | | | |
| Buscapine | • | | | | | | |
| buspirone | | | | | | | • |
| Buspirone hydrochloride | | | | | | | • |
| BUTACLAMOL HYDROCHLORIDE | | • | | | | | |
| butanoic acid | | | | • | | | |
| Butaxamina | | | | • | | | |
| Butofilolol | | | | • | | | |
| butorphanol | | | | | • | • | |
| Butorphanol tartrate | | | | | • | • | |
| Butoxamine [INN] | | | | • | | | |
| BUTOXAMINE HYDROCHLORIDE | | | | • | | | |
| Butylhyoscine | • | | | | | | |
| Butylscopolamine | • | | | | | | |
| C11796 | | | | | | • | |
| C12H19NO2•HCl | | | | | | | • |
| C16H22ClNO | | | | • | | | |
| C19H25NO•HCl | | • | | | | | |
| C19H27ClN2O4•HCl | | | | | | | • |
| C20H27NO3•HCl | | • | • | | | | |
| C50H81N15O9 | | | | | • | | |
| C5976_SIGMA | | | | • | | | |
| cabergoline | | • | | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Caffeine benzoate | | | | | • | | |
| Calcium fusarate | | • | | | | | |
| Camylofin | • | | | | | | |
| Carazolol | | | | • | | | |
| carbachol | • | | | | • | | |
| carbamazepine | | | | | • | | |
| Carbamazepine dihydrate | | | | | • | | |
| Carbamylcholine | • | | | | • | | |
| carbetapentane | • | | | | | • | |
| Carbetapentane citrate | • | | | | | • | |
| carbidopa | • | • | | | | | |
| Carbidopa hydrate | • | • | | | | | |
| Carbidopa Monohydrate | • | • | | | | | |
| Carbidopa, (S)-Isomer | • | • | | | | | |
| Carbidopa-levodopa | • | • | | | | | |
| carbinoxamine | | | • | | | | |
| CARBINOXAMINE MALEATE | | | • | | | | |
| Carebastine | | | • | | | | |
| CARFENTANIL | | | | | • | | |
| CARTEOLOL | | | | • | | | |
| carteolol hydrochloride | | | | • | | | |
| carvedilol | | | | • | | | |
| CCRIS 3490 | | | | • | | | |
| CEC dihydrochloride | | | | • | | | |
| celiprolol | | | | • | | | |
| Centralvet | • | • | | | | | |
| Cerocral | | | | • | | | |
| cetirizine | | | • | | | | |
| Cevimeline | • | | | | | | |
| CGP 20712A | | | | • | | | |
| CGP 20712A methanesulfonate | | | | • | | | |
| CGS 12066B | | | | | | | • |
| CGS 12066B dimaleate | | | | | | | • |
| CH 38083 | | | | • | | | |
| CHEBI: 104181 | | | | | | | • |
| CHEBI: 117275 | | • | | | | | |
| CHEBI: 124645 | | | | | | • | |
| CHEBI: 126213 | • | | | | | | |
| CHEBI: 136626 | | | | | | | • |
| CHEBI: 142179 | | | | | | | • |
| CHEBI: 148898 | | | | • | | | |
| CHEBI: 159721 | • | | • | | | | |
| CHEBI: 161127 | | | | | | | • |
| CHEBI: 178303 | | | • | | | | |
| CHEBI: 201827 | | | • | | | | |
| CHEBI: 238638 | | | • | | | | |
| CHEBI: 268876 | | | • | | | | |
| CHEBI: 334862 | | | | | • | | |
| CHEBI: 350546 | | | | | | | • |
| CHEBI: 36796 | | | • | | • | | • |
| CHEBI: 399928 | | | | | • | | |
| CHEBI: 40751 | | | | • | | | |
| CHEBI: 431080 | | • | | | | | |
| CHEBI: 471632 | | | | | • | | |
| CHEBI: 48295 | | | | | | | • |
| CHEBI: 517861 | | | | | • | | |
| CHEBI: 583615 | | • | | | | | |
| CHEBI: 584626 | | | | | • | | |
| CHEBI: 623294 | | | | | • | | |
| CHEBI: 648957 | | | | | | | • |
| CHEBI: 702837 | | | | • | | | |
| CHEMBL446167 | | | | • | | | |
| CHEMBL93361 | | • | | | | | |
| CHLORAZINE | | • | | | | | |
| Chlorethylclonidine | | | | • | | | |
| Chloropyramine | | | • | | | | |
| Chloropyramine hydrochloride | | | • | | | | |
| chlorpheniramine | | | • | | | | |
| Chlorpheniramine maleate | | | • | | | | |
| chlorpromazine | | • | | | | | |
| Chlorpromazine hydrochloride | | • | | | | | |
| chlorprothixene | | • | | | | | • |
| CIANOPRAMINE | | | | | | | • |
| Cid 105105 | | • | | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| CID5122 | | | | | | | • |
| CID517557 | | • | | • | | | |
| cimaterol | | | | • | | | |
| cimetidine | | | • | | | | |
| Cimetidine hydrochloride | | | • | | | | |
| CINANSERIN | | | | | | | • |
| Cinanserin hydrochloride | | | | | | | • |
| cinnarizine | | | • | | | | |
| ciproxifan | | | • | | | | |
| cirazoline | | | | • | | | |
| cisapride | | | | | | | • |
| Cisapride monohydrate | | | | | | | • |
| citalopram | | | | | | | • |
| citalopram hydrobromide | | | | | | | • |
| CL 316,243 | | | | • | | | |
| CL 316243 | | | | • | | | |
| Cl-Apb | | • | | | | | |
| Clearnal | | | • | | | | |
| clemastine | • | | • | | | | |
| Clemastine (USAN) | • | | • | | | | |
| CLEMASTINE FUMARATE | • | | • | | | | |
| clenbuterol | | | | • | | | |
| Clenbuterol hydrochloride | | | | • | | | |
| clidinium | • | | | | | | |
| CLIDINIUM BROMIDE | • | | | | | | |
| clobenpropit | | | • | | | | |
| Clobutinol | | | | | | • | |
| clomipramine | | | | | | | • |
| Clomipramine hydrochloride | | | | | | | • |
| clonidine | | | | • | | | |
| CLONIDINE HYDROCHLORIDE | | | | • | | | |
| CLOPENTHIXOL | | • | | | | | |
| Clopixol | | • | | | | | |
| Cloranolol | | | | • | | | |
| Clovoxamine | | | | | | | • |
| Clovoxamine fumarate | | | | | | | • |
| clozapine | | | | | | | • |
| cocaethylene | | • | | | | | |
| Cocaethyline | | • | | | | | |
| Cocain-chlorhydrat [German] | | • | | | | | |
| cocaine | | • | | | | | |
| COCAINE HYDROCHLORIDE | | • | | | | | |
| Cocaine muriate | | • | | | | | |
| codeine | | | | | • | • | |
| Cogentin | • | | • | | | | |
| Cogentin mesylate | • | | • | | | | |
| Cognex | • | | | | | | |
| Compazine | | • | | | | | |
| Concerta | | • | | | | | |
| Concordin | | | | • | | | |
| Congesteze | | | • | | | | |
| Contristamine | • | | • | | | | |
| Corindolan | | | | • | | | |
| Corlopam | | • | | | | | |
| Corynanthin | | | | • | | | |
| corynanthine | | | | • | | | |
| Corynanthine hydrochloride | | | | • | | | |
| CP 93129 | | | | | | | • |
| Crispin | | | | | | • | |
| Cromakalim | • | | | | | | |
| CV 705 | | | | • | | | |
| Cyanopindolol | | | | • | | | • |
| CYCLAZOCINE | | | | | • | | |
| CYCLIZINE | | | • | | | | |
| Cyclizine hydrochloride | | | • | | | | |
| Cyclogyl | • | | | | | | |
| cyclopentolate | • | | | | | | |
| CYPROHEPTADINE | | | • | | | | • |
| cyproheptadine hydrochloride | | | • | | | | • |
| Cystospaz | • | | | | | | |
| d1-hyoscyamine | • | | | | | | |
| DAGO | | | | | • | | |
| Daipin | • | | | | | | |
| Dalcipran | | | | | | | • |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Dalgan | | | | | • | | |
| Dalmee | | | | | • | | |
| DAMGO | | | | | • | | |
| Dapiprazole | | | | • | | | |
| Dapiprazole hydrochloride | | | | • | | | |
| Darifenacin | • | | | | | | |
| Darifenacin hydrobromide | • | | | | | | |
| Darvon | | | | | • | | |
| D-Chlorpheniramine | | | • | | | | |
| D-Dopa | • | • | | | | | |
| Debridat | • | | | | | | |
| DEBRISOQUIN SULFATE | | | | | • | | |
| Debrisoquine | | | | | • | | |
| deisopropyldisopyramide | • | | | | | | |
| Deltorphin C | | | | | • | | |
| Deltorphin I | | | | | • | | |
| Denopamine | | | | • | | | |
| Deprenalin | | • | | | | | |
| Deprenil | | • | | | | | |
| Deptropine | | | • | | | | |
| Deptropine citrate | | | • | | | | |
| Deramciclane [INN] | | | | | | | • |
| Deramciclane fumarate | | | | | | | • |
| Dermorphin | | | | | • | | |
| desipramine | • | | | • | | | |
| Desipramine hydrochloride | • | | | • | | | |
| Desloratadine | | | • | | | | |
| Desoxedrine | | • | | • | | | |
| Detrol | • | | | | | | |
| Dexbrompheniramine | | | • | | | | |
| DEXBROMPHENIRAMINE MALEATE | | | • | | | | |
| Dexchlorpheniramine maleate | | | • | | | | |
| DEXETIMIDE | • | | | | | | |
| Dexfenfluramine | | | | | | | • |
| DEXMEDETOMIDINE | | | | | • | | |
| Dexmedetomidinum [INN-Latin] | | | | • | • | | |
| Dexmethylphenidate | | • | | | | | |
| DEXPROPRANOLOL | | | | | • | | |
| Dexpropranolol hydrochloride | | | | | • | | |
| dextroamphetamine | | • | | | | | |
| dextromethorphan | | | | | | • | |
| Dextromethorphan hydrobromide monohydrate | | | | | | • | |
| DEXTROMORAMIDE | | | | | • | | |
| Dextropropoxyphene | | | | | • | | |
| Dextrostat | | • | | | | | |
| DEZOCINE | | | | | • | | |
| Diacetylmonoxime | • | | | | | | |
| Diacetylmorphine | | | | | • | | |
| Diamaprit-2HCl | | | • | | | | |
| Dicetel | • | | | | | | |
| Dicodethal | | | | | • | • | |
| dicyclomine | • | | | | | | |
| Dicyclomine hydrochloride | • | | | | | | |
| Difril | | | | • | | | |
| DIHYDREXIDINE | | • | | | | | |
| Dihydro-alpha-ergocryptine mesylate | | • | | | | | |
| DIHYDROALPRENOLOL | | | | • | | | |
| DIHYDROCODEINE | | | | | • | | |
| Dihydrocodeine bitartrate | | | | | • | | |
| Dihydroergocornine | | • | | | | | |
| Dihydroergocristine | | | | • | | | |
| DIHYDROERGOCRISTINE MESYLATE | | | | • | | | |
| Dihydroergocryptine | | • | | | | | |
| dihydroergotamine | | • | | | • | | • |
| Dihydroergotamine mesilate | | • | | | • | | • |
| Dihydroetorphine | | | | | • | | |
| Dihydromorphine | | | | | • | | |
| Dihydroquinidine | • | | | | | | |
| Dihydroquinine | • | | | | | | |
| dihydroxyphenylalanine | | • | | | | | |
| Dilaudid | | | | | • | | |
| Dilevalol | | | | • | | | |
| Dilevalol hydrochloride | | | | • | | | |
| Dimaprit | | | • | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Dimemorfan | | | | | | • | |
| Dimemorfan (INN) | | | | | | • | |
| Dimepheptanol | | | | | • | | |
| Dimethindene maleate | | | • | | | | |
| DIMETHYLTRYPTAMINE | | | | | | | • |
| Dimetindene | | | • | | | | |
| Diphemanil | • | | | | | | |
| diphenhydramine | | | • | | | | |
| Diphenhydramine citrate | | | • | | | | |
| DIPHENHYDRAMINE HYDROCHLORIDE | | | • | | | | |
| DIPHENOXYLATE | | | | | • | | |
| Diphenoxylate HCl | | | | | • | | |
| dipivefrin | | | | • | | | |
| Dipivefrin hydrochloride | | | | • | | | |
| Dironyl | | • | | | | | |
| Ditropan | • | | | | | | |
| Dixyrazine | | | | | | • | |
| DL-Adrenaline | | | | • | | | |
| dl-Desoxyephedrine | | • | | • | | | |
| DL-DOPA | | • | | | | | |
| dl-Narcotine | | | | | | • | |
| DL-Oxyfedrine | | | | • | | | |
| DL-threo-3,4-Dihydroxyphenylserine | | • | | | | | |
| DL-threo-DOPS | | • | | | | | |
| dobutamine | | | | • | | | |
| Dobutamine hydrochloride | | | | • | | | |
| docarpamine | | • | | | | | |
| dolasetron | | | | | | | • |
| DOLASETRON MESYLATE | | | | | | | • |
| Dolasetronum [INN-Latin] | | | | | | | • |
| Domin | | • | | • | | | |
| domperidone | | • | | | | | |
| Domperidone Maleate | | • | | | | | |
| Dopabain | • | • | | | | | |
| dopamine | | • | | | | | |
| Dopamine hydrochloride | | • | | | | | |
| dopazinol | | • | | | | | |
| Dopexamine | | • | | • | | | |
| DOPEXAMINE HYDROCHLORIDE | | • | | • | | | |
| dosulepin hydrochloride | | | | • | | | |
| Dotarizine [INN] | | | | | | | • |
| Dothiepin | | | | • | | | |
| doxazosin | | | | • | | | |
| Doxazosin mesylate | | | | • | | | |
| doxepin | | | • | | | | |
| Doxepin Hydrochloride | | | • | | | | |
| Doxepine | | | • | | | | |
| DOXOFYLLINE | | | | | | • | |
| doxylamine | | | • | | | | |
| Doxylamine succinate | | | • | | | | |
| DPDPE | | | | | • | | |
| Dramamine | | | • | | | | |
| Drixoral | | | • | | | | |
| Dronabinol | | | | | • | | |
| droperidol | | • | | | | | |
| dropropizine | | | | | | • | |
| drotaverine | | • | | | | | |
| droxidopa | | • | | | | | |
| DSP 4 | | | | • | | | |
| DSP-4 hydrochloride | | | | • | | | |
| DU-29373 | | | | | | | • |
| duloxetine | | • | | • | | | • |
| DULOXETINE HYDROCHLORIDE | | • | | • | | | • |
| DuP 734 | | | | | | | • |
| Duremesin | | • | | | | | |
| Dynorphin 1-13 | | | | | • | | |
| ebastine | | | • | | | | |
| Ebrotidine | | | • | | | | |
| Ecopipam | | • | | | | | |
| Edronax | | | | • | | | |
| EEDQ | | • | | • | | | • |
| Efaroxan | | | | • | | | |
| Efaroxan hydrochloride | | | | • | | | |
| Effexor | | | | | | | • |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Effortilvet | | | | • | | | |
| Eldoral | | | | • | | | |
| Eletriptan | | | | | | | • |
| Eletriptan hydrobromide | | | | | | | • |
| Eltoprazine | | | | | | | • |
| Eltoprazine hydrochloride | | | | | | | • |
| Emadine | | | • | | | | |
| emedastine | | | • | | | | |
| Emepronum | • | | | | | | |
| Emergil | | • | | | | | |
| Enantio-PAF C-16 | | | | • | | | |
| Endomorphin 1 | | | | | • | | |
| Endomorphin 2 | | | | | • | | |
| Endovalpin | • | | | | | | |
| ENTACAPONE | | • | | | | | |
| Epanolol | | | | • | | | |
| eperisone | • | | | | | | |
| Ephedrine | | | | • | | | |
| Ephedrine hydrochloride | | | | • | | | |
| EPHEDRINE SULFATE | | | | • | | | |
| Ephetonine | | | | • | | | |
| Epibatidine | | | | | • | | |
| epinastine | | | • | | | | |
| epinephrine | | | | • | | | |
| Epinephrine hydrochloride | | | | • | | | |
| Eplivanserin fumarate | | | | | | | • |
| Ergocryptine | | • | | | | | |
| Ergocryptine mesylate | | • | | | | | |
| Ergocryptine-alpha | | • | | | | | |
| Ergoloid mesylate | | | | • | | | |
| Ergomar | | | | | • | | • |
| Ergotamin | | | | | • | | • |
| ERGOTAMINE | | | | • | • | | • |
| ergotamine tartrate | | | | • | • | | • |
| Esbuphon | | | | • | | | • |
| Escitalopram | | | | | | | • |
| Escitalopram oxalate | | | | | | | • |
| Eseroline | | | | | • | | |
| ESMOLOL | | | | • | | | |
| Esmolol hydrochloride | | | | • | | | |
| ethaverine | • | | | | | | |
| Ethaverine hydrochloride | • | | | | | | |
| ethopropazine | • | | | • | • | | |
| Ethopropazine hydrochloride | • | | | • | • | | |
| ETHYLKETOCYCLAZOCINE | | | | | • | | |
| Ethylmorphine | | | | | • | • | |
| Eticlopride | | • | | | | | |
| Eticlopride hydrochloride | | • | | | | | |
| Etilefrine | | | | • | | | |
| etilefrine hydrochloride | | | | • | | | |
| Etintidine | | | • | | | | |
| Etintidine hydrochloride | | | • | | | | |
| Etorphine | | | | | • | | |
| EU-0100372 | | | | • | | | |
| Eupaverina | • | | | | | | |
| Euspirol | | | | • | | | |
| Evoxac | • | | | | | | |
| exaprolol | | | | • | | | |
| Exaprolol hydrochloride | | | | • | | | |
| Falipamil | • | | | | | | |
| Famotidina | | | • | | | | |
| famotidine | | | • | | | | |
| Famotidine HCl | | | • | | | | |
| Fananserin | | • | | | | | • |
| Fastin | | | | • | | | |
| Femoxetine | | | | | | | • |
| Femoxetinum [INN-Latin] | | | | | | | • |
| Fencarbamide hydrochloride | • | | | | | | |
| Fencarol | | | • | | | | |
| Fenclonine | | | | | | | • |
| fenfluramine | | | | | | | • |
| Fenistil | | | • | | | | |
| fenoldopam | | • | | | | | |
| Fenoldopam bromide | | • | | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| fenoterol | | | | • | | | |
| Fenoterol hydrobromide | | | | • | | | |
| Fenoverine | • | | | | | | |
| fentanyl | | | | | • | | |
| Fentora | | | | | • | | |
| fexofenadine | | | • | | | | |
| FG 4963 | | | | | | | • |
| Finaten | | | | | | • | |
| Finibron | | | | | | • | |
| flavoxate | • | | | | | | |
| Flavoxate hydrochloride | • | | | | | | |
| Flb 457 | | • | | | | | |
| Flesinoxan | | | | | | | • |
| Flesinoxan hydrochloride | | | | | | | • |
| FLESTOLOL | | | | • | | | |
| FLESTOLOL SULFATE | | | | • | | | |
| Fluanxol depot (TN) | | • | | | | | |
| flunarizine | | | • | | | | |
| flunarizine hydrochloride | | | • | | | | |
| Fluorofen | | | • | | | | |
| fluoxetine | | | | | | | • |
| FLUPENTHIXOL DECANOATE | | • | | | | | |
| Flupentixol | | • | | | | | |
| FLUPHENAZINE | | • | | | | | |
| Fluphenazine hydrochloride | | • | | | | | |
| Fluspirilene | | • | | | | | |
| fluvoxamine | | | | | | | • |
| FLUVOXAMINE MALEATE | | | | | | | • |
| Focalin | | • | | | | | |
| FOMINOBEN | | | | | | • | |
| FONAZINE | | | • | | | | |
| formoterol | | | | • | | | |
| Frovatriptan | | | | | | | • |
| Frovatriptan succinate | | | | | | | • |
| fusaric acid | | • | | | | | |
| gabapentin | • | | | | | | |
| Galantamin | • | | | | | | |
| Galantamine | • | | | | | | |
| Galantamine hydrobromide | • | | | | | | |
| Ganglefene | • | | | | | | |
| Ganglerone | • | | | | | | |
| Gastrozepin | • | | | | | | |
| Gbr 12783 | | • | | | | | |
| GBR12935 | | • | | | | | |
| Geodon | | • | | | | | • |
| Gepirone | | | | | | | • |
| GEPIRONE HYDROCHLORIDE | | | | | | | • |
| Gevatran | | | | | | | • |
| glafenine | | | | | • | | |
| Glaucine | • | | | | | • | |
| Glauconex | | | | • | | | |
| Glaxo Wellcome brand of acrivastine | | | • | | | | |
| GLYCOPYRROLATE | • | | | | | | |
| Gnoscopine | | | | | | • | |
| Gotensin | | | | • | | | |
| GR 113808 | | | | | | | • |
| GR-127935 | | | | | | | • |
| granisetron | | | | | | | • |
| Granisetron hydrochloride | | | | | | | • |
| guanabenz | | | | • | | | |
| Guanabenz acetate | | | | • | | | |
| GUANETHIDINE | | | | • | | | |
| guanethidine sulfate | | | | • | | | |
| GUANFACINE | | | | • | | | |
| guanfacine hydrochloride | | | | • | | | |
| guanidine | • | | | | | | |
| Guanidine bromide | • | | | | | | |
| Guanidine hydrochloride | • | | | | | | |
| Guanidine nitrate | • | | | | | | |
| GUANIDINIUM | | | | | | | |
| Gynergen | | | | | | • | • |
| Hag-PC | | | | • | | | |
| haloperidol | | • | | | | | |
| Haymine | | | • | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| HEAT | | | | • | | | |
| Hemicholinium | • | | | | | | |
| Hemicholinium-3 | • | | | | | | |
| Heroin hydrochloride | | | | | • | | |
| Hhsi-difenidol | • | | | | | | |
| Higenamine | | | | • | | | |
| Himbacine | • | | | | | | |
| histamine | | | • | | | | |
| Histamine dihydrochloride | | | • | | | | |
| Histamine diphosphate | | | • | | | | |
| Histamine hydrochloride | | | • | | | | |
| Histantin | | | • | | | | |
| Hoe-893d | | | | • | | | |
| HOMATROPINE | • | | | | | | |
| Homatropine hydrobromide (R,S) | • | | | | | | |
| Homocodeine | | | | | | • | |
| Hycodan | | | | | • | • | |
| Hydergine | | • | | • | | | |
| Hydriatine | | | | • | | | |
| Hydroaminacrine | • | | | | | | |
| HYDROCODONE | | | | | • | • | |
| hydromorphone | | | | | • | | |
| Hydromorphone hydrochloride | | | | | • | | |
| hydroquinidine | • | | | | | | |
| Hydroquinidine hydrochloride | • | | | | | | |
| HYDROQUININE | • | | | | | | |
| hydroxyzine | | | • | | | | |
| Hydroxyzine pamoate | | | • | | | | |
| Hyoscine hydrobromide | • | | | | | | |
| Hyoscine Methobromide | • | | | | | | |
| hyoscyamine | • | | | | | | |
| Hyoscyamine (D)- | • | | | | | | |
| Hyoscyamine sulfate | • | | | | | | |
| Hyoscyamine sulfate (USP) | • | | | | | | |
| Hypostamine | | | • | | | | |
| Hysco | • | | | | | | |
| Ibopamine | | • | | | | | |
| ibuprofen | | | | | • | | |
| IBZM | | • | | | | | |
| Icatibant | | | | • | | | |
| Icatibant acetate | | | | • | | | |
| Ici 118551 | | | | • | | | |
| ICI-89406 | | | | • | | | |
| IDAZOXAN | | | | • | | | |
| IDAZOXAN HYDROCHLORIDE | | | | • | | | |
| Ifenprodil | | | | • | | | |
| ifenprodil tartrate | | | | • | | | |
| IHEAT | | | | • | | | |
| Ildamen | | | | • | | | |
| imetit | | | • | | | | |
| Imetit dihydrobromide | | | • | | | | |
| Imidacloprid | • | | | | | | |
| imipramine | | | | • | | | |
| Imipramine hydrochloride | | | | • | | | |
| IMPROMIDINE | | | • | | | | |
| Impromidine hydrochloride | | | • | | | | |
| Inapetyl | | • | | • | | | |
| INDALPINE | | | | | | | • |
| indanidine | | | | • | | | |
| Indenolol | | | | • | | | |
| Inderal | | | | • | | | |
| Indolophenanthridine | • | • | | | | | |
| INDORAMIN | | | | • | | | |
| Indorenate Hydrochloride | | | | | | | • |
| Inopamil | | • | | | | | |
| Insidon | | | | • | | | |
| intropin | | • | | | | | |
| Iodocyanopindolol | | | | • | | | |
| ipratropium | • | | | | | | |
| ipratropium bromide | • | | | | | | |
| Ipratropium bromide monohydrate | • | | | | | | |
| Iprazochrome | | | | | | | • |
| Ips-339 | | | | • | | | |
| IPSAPIRONE | | | | | | | • |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Ipsapirone hydrochloride | | | | | | | • |
| Ismelin | | | | • | | | |
| Isoaminile | | | | | | • | |
| Isocodeine | | | | | • | • | |
| isoetharine | | | | • | | | |
| isoproterenol | | | | • | | | |
| ISOPROTERENOL HYDROCHLORIDE | | | | • | | | |
| Isoproterenol sulfate | | | | • | | | |
| Isospaglumic acid | | | • | | | | |
| Isothipendyl | | | • | | | | |
| isoxsuprine | | | | • | | | |
| Isoxsuprine hydrochloride | | | | • | | | |
| Itrop | • | | | | | | |
| Janimine | | | | • | | | |
| Jetrium tartrate | | | | | • | | |
| Kadian | | | | | • | | |
| Kerlone | | | | • | | | |
| Ketanserin | | | | | | | • |
| Ketanserin tartrate | | | | | | | • |
| Ketobemidone | | | | | • | | |
| Ketogan | | | | | • | | |
| ketotifen | | | • | | | | |
| KETOTIFEN FUMARATE | | | • | | | | |
| Kinichron | • | | | • | | | |
| Kytril | | | | | | | • |
| L 657743 | | | | • | | | |
| L-741,626 | | • | | | | | |
| labetalol | | | | • | | | |
| Labetalol hydrochloride | | | | • | | | |
| lafutidine | | | • | | | | |
| L-alpha-Acetyl-N-normethadol | | | | | • | | |
| Landiolol | | | | • | | | |
| lappaconitine | | | | | • | | |
| Lazabemide | | • | | | | | |
| Legatrin | | | | | • | | |
| Leoplexamin | | | | | • | | |
| l-Ephedrine | | | | • | | | |
| Lethidrone | | | | | • | | |
| Levacetylmethadol | | | | | • | | |
| Levallorphan | | | | | • | | |
| Levamfetamine | | • | | • | | | |
| Levcromakalim | • | | | | | | |
| Levetimide | • | | | | | | |
| LEVOBUNOLOL | | | | • | | | |
| Levobunolol•HCl | | | | • | | | |
| levocabastine | | | • | | | | |
| LEVOCABASTINE HYDROCHLORIDE | | | • | | | | |
| Levocetirizine | | | • | | | | |
| levodopa | | • | • | | | | |
| Levodropropizine | | | | | | • | |
| Levomeprazine | | • | | | | • | |
| Levomepromazine | | • | | | | • | |
| Levomethorphan | | | | | | • | |
| Levomethorphan hydrobromide | | | | | | • | |
| levorphanol | | | | | • | | |
| Levosalbutamol | | | | • | | | |
| Levospasme | | • | | | | | |
| Levsinex | | • | | | | | |
| LIDAMIDINE | | | | • | | | |
| LIDAMIDINE HYDROCHLORIDE | | | | • | | | |
| Lilly 53857 | | | | | | | • |
| l-Isoprenaline chloride | | | | • | | | |
| LISURIDE | | • | | | | | • |
| lisuride maleate | | • | • | | | | • |
| L-Noradrenaline bitartrate | | | | • | | | |
| LODOXAMIDE TROMETHAMINE | | | • | | | | |
| Lofentanil | | | | | • | | |
| Lofentanil oxalate | | | | | • | | |
| Longifene | | | • | | | | |
| Lopac0__000714 | | | | • | | | |
| Lopac-A-164 | | | | | | | • |
| Lopac-C-130 | | • | | | | | |
| Lopressor | | | | • | | | |
| loratadine | | | • | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Lorcet | | | | | • | | |
| Lotronex | | | | | | | • |
| loxapine | | • | | | | | |
| Loxapine hydrochloride | | • | | | | | |
| Loxapine succinate | | • | | | | | |
| Loxtidine | | | • | | | | |
| L-pentazocine | | | | | • | | |
| LSD tartrate | | | | | | | • |
| LUPITIDINE HYDROCHLORIDE | | | • | | | | |
| LY 235959 | • | | | | | | |
| LY 277359 maleate | | | | | | | • |
| Ly-165163 | | | | | | | • |
| Lysergide | | | | | | | • |
| Lysivane | • | | • | • | | | |
| Mabuterol | | | | • | | | |
| madopar | | • | | | | | |
| Malexil | | | | | | | • |
| maprotiline | | | | • | | | |
| Maprotiline hydrochloride | | | | • | | | |
| Marzine | | | • | | | | |
| Maxolon | | • | | | | | |
| mazindol | | • | | • | | | |
| Mci 9042 | | | | | | | • |
| Mcn 5652 | | | | | | | • |
| McN-A-343 | • | | | | | | |
| mCPBG | | | | | | | • |
| m-CPBG hydrochloride | | | | | | | • |
| MDL-100907 | | | | | | | • |
| MDMA | | | | | • | | • |
| mebeverine | | • | | | | | |
| MEBEVERINE HYDROCHLORIDE | | • | | | | | |
| Meclastine | | | • | | | | |
| meclizine | | | • | | | | |
| Meclizine hydrochloride | | | • | | | | |
| Meclizine Mixture With Niacin | | | • | | | | |
| Mecloprodine | | | • | | | | |
| Medetomidine | | | | • | • | | |
| Medetomidine hydrochloride | | | | • | • | | |
| MEDROXALOL | | | | • | | | |
| Medroxalol hydrochloride | | | | • | | | |
| Melevodopa | | • | | | | | |
| memantine | | • | • | | | | |
| MEMANTINE HYDROCHLORIDE | | • | • | | | | |
| meperidine | | | | | • | | |
| Mepindolol | | | | • | | | |
| Meptazinol | | | | | • | | |
| MEPTAZINOL HYDROCHLORIDE | | | | | • | | |
| mequitazine | | | • | | | | |
| Merital | | • | | | | | |
| mescaline | | | | | | | • |
| Mescomine | • | | | | | | |
| mesoridazine | | • | | | | | |
| Mesulergine | • | • | | | | | • |
| Mesulergine hydrochloride | • | • | | | | | • |
| Metabolites (street) | | | | | • | | • |
| metaproterenol | | | | • | | | |
| Metaproterenol hemisulfate | | | | • | | | |
| Metaraminol bitartrate | | | | • | | | |
| Metatsin | • | | | | | | |
| metergoline | | • | | | | | • |
| methacholine | • | | | | | | |
| Methacholine chloride | • | | | | | | |
| methadone | | | | | • | • | |
| Methadyl acetate | | | | | • | | |
| METHAMPHETAMINE | | • | | • | | | |
| Methamphetamine hydrochloride | | • | | • | | | |
| methantheline | • | | | | | | |
| methapyrilene | | | • | | | | |
| METHAPYRILENE HYDROCHLORIDE | | | • | | | | |
| Metharsinat | | | • | | | | |
| methiothepin | | | | | | | • |
| Methiothepin maleate | | | | | | | • |
| Methoctramine | • | | | | | | |
| Metholes | | | | • | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Methorphan | | | | | | • | |
| methoxamine | | | | • | | | |
| METHOXAMINE HYDROCHLORIDE | | | | • | | | |
| Methylatropine | • | | | | | | |
| methyldopa | | | | • | | | |
| METHYLDOPA SESQUIHYDRATE | | | | • | | | |
| Methylfurmetide | • | | | | | | |
| methyloctatropine bromide | • | | | | | | |
| methylphenidate | | • | | | | | |
| Methylscopolamine | • | | | | | | |
| methysergide | | | | | | | • |
| Methysergide maleate | | | | | | | • |
| METIAMIDE | | | • | | | | |
| Metipranolol | | | | • | | | |
| metoclopramide | | • | | | | | |
| Metoclopramide dihydrochloride | | • | | | | | |
| metoprolol | | | | • | | | |
| Metoprolol fumarate | | | | • | | | |
| mianserin | | | • | • | | | • |
| Mianserin hydrochloride | | | • | • | | | • |
| Mictonorm | • | | | | | | |
| Midaglizole | | | | • | | | |
| Midaglizole hydrochloride | | | | • | | | |
| midodrine | | | | • | | | |
| MIDODRINE HYDROCHLORIDE | | | | • | | | |
| Mifentidine | | | • | | | | |
| Milnacipran | | | | • | | | • |
| Minipress | | | | • | | | |
| Mintussin | • | | | | | | |
| Minusine | | | | • | | | |
| Mirapex | • | • | | | | | |
| mirtazapine | | | • | • | | | |
| Mivazerol | | | | • | | | |
| Mizolastine | | | • | | | | |
| MK-212 | | | | | | | • |
| MK-912 | | | | • | | | |
| M-Mptp | | • | | | | | |
| Mofegiline | | • | | | | | |
| Mofegiline hydrochloride | | • | | | | | |
| MONATEPIL MALEATE | | | | • | | | |
| morphine | | | | | • | | |
| Morphine hydrochloride | | | | | • | | |
| MORPHINE SULFATE | | | | | • | | |
| morphinesulfate | | | | | • | | |
| Mosapride | | | | | | | • |
| Mosapride citrate | | | | | | | • |
| Moxaverine | • | | | | | | |
| Moxisylyte | | | | • | | | |
| moxisylyte hydrochloride | | | | • | | | |
| MPTP | | • | | | | | |
| Muscarin | • | | | | | | |
| Myonal | • | | | | | | |
| Myophedrine | | | | • | | | |
| N,3-Dimethylmorphinan | | | | | | • | |
| Naaxia | | | • | | | | |
| N-acetylaspartylglutamate | | | • | | | | |
| N-Acetyl-Asp-Glu | | | • | | | | |
| nadolol | | | | • | | | |
| Nafadotride | | • | | | | | |
| nafronyl | | | | | | | • |
| Nafronyl oxalate | | | | | | | • |
| naftopidil | | | | • | | | |
| nalbuphine | | | | | • | | |
| Nalorphine | | | | | • | | |
| Nalorphine hydrochloride | | | | | • | | |
| naloxone | | | | | • | | |
| Naloxone hydrochloride | | | | | • | | |
| NAN-190 hydrobromide | | | | | | | • |
| naphazoline | | | | • | | | |
| NAPHAZOLINE HYDROCHLORIDE | | | | • | | | |
| Naphazoline nitrate | | | | • | | | |
| Naphthisen | | | | • | | | |
| naratriptan | | | | | | | • |
| Nargoline | | | | • | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Narphen | | | | | • | | |
| Navaron | | • | | | | | |
| Nazasetron | | | | | | | • |
| NCGC00015261-01 | • | | | | | | |
| nchembio873-comp43 | | • | | | | | |
| nchembio873-comp53 | | | | | | | • |
| nchembio873-comp67 | | • | | | | | |
| Ncq 298 | | • | | | | | |
| Nebivolol | | | | • | | | |
| Nebracetam | • | | | | | | |
| Nebracetam fumarate | • | | | | | | |
| Nedeltran | | | • | | | | |
| nefopam | | | | | • | | |
| Nefopam hydrochloride | | | | | • | | |
| nemonapride | | • | | | | | |
| NEOSTIGMINE | • | | | | | | |
| neostigmine bromide | • | | | | | | |
| Neostigmine methyl sulfate | • | | | | | | |
| nicergoline | | | | • | | | |
| NIH-8805 | | | | | • | | |
| Nipradilol | | | | • | | | |
| Nisentil | | | | | • | | |
| nitrous oxide | | | | | • | | |
| nizatidine | | | • | | | | |
| N-Methylspiroperidol | | • | | | | | |
| Noleptan | | | | | | • | |
| Nomifensine | | • | | | | | |
| Norephedrine | | | | • | | | |
| norepinephrine | | | | • | | | |
| Norfenefrine | | | | • | | | |
| Norfenfluramine | | | | | | | • |
| Norflex | • | | | | | | |
| Norprolac | | • | | | | | |
| nortriptyline | | | | • | | | |
| Nortriptyline hydrochloride | | | | • | | | |
| Norzine Ampuls | | | • | | | | |
| Noscapalin | | | | | | • | |
| noscapine | | | | | | • | |
| Novopropoxyn | | | | | • | | |
| n-Propylapomorphine | • | • | | | | | |
| NSC10004 | • | | | | • | • | |
| NSC114335 | • | | | | | | |
| NSC289336 | | | | • | | | |
| NSC61391 | | • | | | | | |
| NSC61806 | • | | | • | | | |
| NSC69886 | | • | | | | | |
| NSC79303 | • | | | | | | |
| Nubain | | | | | • | | |
| nylidrin | | | | • | | | |
| Nylidrin hydrochloride | | | | • | | | |
| Octatropine | • | | | | | | |
| octopamine | | | | • | | | |
| Oils, peppermint | • | | | | | | |
| olanzapine | | | | | | | • |
| Olopatadine | | | • | | | | |
| ondansetron | | | | | | | • |
| ONDANSETRON HYDROCHLORIDE | | | | | | | • |
| Opana | | | | | • | | |
| Opcon | | | | • | | | |
| Opipramol | | | | • | | | |
| Opreal_021650 | | • | | | | | |
| Optimine | | | • | | | | |
| Orlaam | | | | | • | | |
| orphenadrine | • | | | | | | |
| Orphenadrine hydrochloride | • | | | | | | |
| Otenzepad | • | | | | | | |
| Otilonium Bromide | • | | | | | | |
| oxatomide | | | • | | | | |
| Oxeladin | | | | | | • | |
| oxidopamine | | | | • | | | |
| Oxifedrinum | | | | • | | | |
| oxitropium bromide | • | | | | | | |
| OXMETIDINE | | | • | | | | |
| Oxmetidine hydrochloride | | | • | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Oxolamine | | | | | | • | |
| Oxolamine citrate | | | | | | • | |
| Oxotremorine | • | | | | | | |
| oxotremorine methiodide | • | | | | | | |
| oxprenolol | | | | • | | | |
| Oxprenolol hydrochloride | | | | • | | | |
| oxybutynin | • | | | | | | |
| Oxybutynin chloride | • | | | | | | |
| oxycodone | | | | | • | | |
| Oxycodone hydrochloride | | | | | • | | |
| oxymetazoline | | | | • | | | |
| oxymorphone | | | | | • | | |
| oxyphenonium | • | | | | | | |
| OXYPHENONIUM BROMIDE | • | | | | | | |
| ozagrel | | | • | | | | |
| ozagrel hydrochloride | | | • | | | | |
| Palfadonna | | | | | • | | |
| Palladone | | | | | • | | |
| Palonosetron | | | | | | | • |
| Palonosetron hydrochloride | | | | | | | • |
| Papaveretum | | | | | • | • | |
| PAPP | | | | | | | • |
| Paracodin | | | | | • | | |
| Paracymethadol | | | | | • | | |
| Parasan | • | | | | | | |
| Parlodel | • | • | | | | | |
| paroxetine | | | | | | | • |
| Paroxetine hydrochloride | | | | | | | • |
| Paroxetine maleate | | | | | | | • |
| Pataday | | | • | | | | |
| Paxil | | | | | | | • |
| PBPO | | | • | | | | |
| p-Chloramphetamine | | | | | | | • |
| Pemilaston | | | • | | | | |
| Pemirolast | | | • | | | | |
| penbutolol | | | | • | | | |
| PENFLURIDOL | | • | | | | | |
| Pentalgine | | | | | • | | |
| pentazocine | | | | | • | | |
| Peracon | | | | | | • | |
| Perazine maleate | | • | | | | | |
| pergolide | | • | | | | | |
| PERGOLIDE MESYLATE | | • | | | | | |
| Perhydrohistrionicotoxin | • | | | | | | |
| Periactin | | | • | | | | • |
| Pernazine | | | • | | | | |
| Pernovine | | | • | | | | |
| perphenazine | | • | | | | | |
| Pethidine hydrochloride | | | | | • | | |
| pFHHSiD | • | | | | | | |
| phenacetin | | | | | | • | |
| PHENAZOCINE | | | | | | • | |
| Phencarbamide | • | | | | | | |
| Phenindamine | | | • | | | | |
| pheniramine | | | • | | | | |
| PHENIRAMINE MALEATE | | | • | | | | |
| PHENOPERIDINE | | | | | • | | |
| Phenoperidine hydrochloride | | | | | • | | |
| Phenopropamine | • | | | | | | |
| Phenoxene | • | | • | | | | |
| phenoxybenzamine | | | | • | | | |
| Phenoxybenzamine hydrochloride | | | | • | | | |
| phentermine | | | | • | | | |
| phentolamine | | | | • | | | |
| Phentolamine mesylate | | | | • | | | |
| phenylbiguanide | | | | | | | • |
| phenylephrine | | | | • | | | |
| PHENYLEPHRINE HYDROCHLORIDE | | | | • | | | |
| phenylpropanolamine | | | | • | | | |
| PHENYLPROPANOLAMINE HYDROCHLORIDE | | | | • | | | |
| PHOLCODINE | | | | | | • | |
| Phospholine iodide | • | | | | | | |
| Picumast | | | • | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Picumast dihydrochloride | | | • | | | | |
| pilocarpine | • | | | | | | |
| Pilocarpine- | • | | | | | | |
| Pilocarpine hydrochloride | • | | | | | | |
| Pilocarpine nitrate | • | | | | | | |
| Pilocarpine nitrate salt | • | | | | | | |
| pimozide | | • | | | | | |
| Pinaverium | • | | | | | | |
| pindolol | | | | • | | | • |
| Pipamperone | | | | | | | • |
| Pipazethate | | | | | | • | |
| Piperoxan | | | | • | | | |
| PIRBUTEROL | | | | • | | | |
| pirenzepine | • | | | | | | |
| Pirenzepine dihydrochloride | • | | | | | | |
| piribedil | • | • | | | | | |
| Piribedil hydrochloride | • | • | | | | | |
| Piribedil mesylate | • | • | | | | | |
| Piritramide | | | | | • | | |
| PIZOTYLINE | | | | | | • | • |
| Plegine | | | | • | | | |
| p-MPPI | | | | | | | • |
| Pnu 99194A | | • | | | | | |
| Pondimin | | | | | | | • |
| practolol | | | | • | | | |
| Pramipexol [Spanish] | | • | | | | | |
| pramipexole | • | • | | | | | |
| prazosin | | | | • | | | |
| Prazosin hydrochloride | | | | • | | | |
| PRBCM | • | | | | | | |
| Precedex | | | | | • | | |
| Preclamol | • | • | | | | | |
| Preclamolum [Latin] | • | • | | | | | |
| Prednisolone 21-pivalate | | | | • | | | |
| Prenalterol | | | | • | | | |
| PRENYLAMINE | | | | • | | | |
| Prestwick_144 | | | | • | | | |
| Prialt | | | | | • | | |
| Privine | | | | • | | | |
| Prizidilol | | | | • | | | |
| PROCATEROL | | | | • | | | |
| procaterol hydrochloride | | | | • | | | |
| prochlorperazine | | • | | | | | |
| Prochlorperazine dimaleate | | • | | | | | |
| Prochlorperazine edisylate | | • | | | | | |
| Prochlorperazine maleate | | • | | | | | |
| procyclidine | • | | | | | | |
| Procyclidine hydrochloride | • | | | | | | |
| Progabide | • | | | | | | |
| Prolixin | | • | | | | | |
| promazine | | • | | | | | |
| PROMAZINE HYDROCHLORIDE | | • | | | | | |
| Promedol | | | | | • | | |
| promethazine | | | • | | | | |
| PROMETHAZINE HYDROCHLORIDE | | | • | | | | |
| propantheline | • | | | | | | |
| PROPANTHELINE BROMIDE | • | | | | | | |
| Propitan | | | | | | | • |
| Propiverine | • | | | | | | |
| propiverine hydrochloride | • | | | | | | |
| propranolol | | | | • | | | |
| Propranolol hydrochloride | | | | • | | | |
| Proroxan [INN] | | | | • | | | |
| Proscomide | • | | | | | | |
| Prothiaden | | | | | | | |
| protopine | | | | • | | • | |
| PROTOPINE HYDROCHLORIDE | | | | • | | • | |
| protriptyline | | | | • | | | |
| Protriptyline hydrochloride | | | | • | | | |
| Proxicromil | | | • | | | | |
| Prozac | | | | | | | • |
| Psxeladine | | | | | | • | |
| Psychostyl | | | | • | | | |
| pyrilamine | | | • | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| PYRILAMINE MALEATE | | | • | | | | |
| Pyrroxane | | | | • | | | |
| Quadramet | | | | | | • | |
| Quifenadine | | | • | | | | |
| Quinagolide | | • | | | | | |
| Quinelorane | | • | | | | | |
| Quinidex | • | | | | • | | |
| quinidine | • | | | | • | • | |
| Quinidine sulfate | • | | | | • | | |
| Quinine | | | | | | • | |
| Quinine hydrochloride | | | | | | • | |
| quinine sulfate | | | | | | • | |
| QUININE SULFATE DIHYDRATE | | | | | | • | |
| QUINPIROLE | | • | | | | | |
| quipazine | | | | | | | • |
| QUIPAZINE MALEATE | | | | | | | • |
| R(−)-Denopamine | | | | • | | | |
| R-50547 | | • | | | | | |
| RACLOPRIDE | | • | | | | | |
| Raclopride C11 | | • | | | | | |
| Raclopridum [Latin] | | • | | | | | |
| RACTOPAMINE | | | | • | | | |
| Ractopamine hydrochloride | | | | • | | | |
| Ramosetron | | | | | | | • |
| Ramosetron hydrochloride | | | | | | | • |
| ranitidine | | | • | | | | |
| Ranitidine bismuth citrate | | | • | | | | |
| ranitidine hydrochloride | | | • | | | | |
| Rapimine | | | • | | | | |
| Rauwolscine | | | | • | | | |
| Reboxetine | | | | • | | | |
| Reboxetine mesylate | | | | • | | | |
| Reboxetine mesylate hydrate | | | | • | | | |
| Redux | | | | | | | • |
| Reglan | | • | | | | | |
| Relaspium | • | | | | | | |
| REMIFENTANIL | | | | | • | | |
| REMIFENTANIL HYDROCHLORIDE | | | | | • | | |
| Remoxipride | | • | | | | | |
| REMOXIPRIDE HYDROCHLORIDE | | • | | | | | |
| Renzapride | | | | | | | • |
| Renzapride hydrochloride | | | | | | | • |
| repirinast | | | • | | | | |
| Reproterol | | | | • | | | |
| REPROTEROL HYDROCHLORIDE | | | | • | | | |
| reserpine | | | | • | | | |
| Respilene | | | | | | • | |
| Restenacht | • | | | | | | |
| Rexigen | | | | • | | | |
| Rexolate | | | | | | • | |
| Rilmenidine | | | | • | | | |
| Rilmenidine phosphate | | | | • | | | |
| Rimiterol | | | | • | | | |
| Rimiterol Hydrobromide | | | | • | | | |
| risperidone | | • | | | | | • |
| ritanserin | | | | | | | • |
| ritodrine | | | | • | | | |
| Ritodrine hydrochloride | | | | • | | | |
| rizatriptan | | | | | | | • |
| Rizatriptan benzoate | | | | | | | • |
| Ro 363 | | | | • | | | |
| Robinal | • | | | | | | |
| Robinul | • | | | | | | |
| Rociverine | • | | | | | | |
| ropinirole | | • | | | | | |
| Ropinirole hydrochloride | | • | | | | | |
| Rotenolone | | | | • | | | |
| Rotigotine | | • | | | | | |
| RS 86, hydrobromide | • | | | | | | |
| RS 86HB | • | | | | | | |
| RS-25259-197 | | | | | | | • |
| RU 24969 | | | | | | | • |
| RU-24213 | | • | | | | | |
| S(−)Eticlopride hydrochloride | | • | | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| S-20500 | | • | | | | | |
| Salbutamol | | | | • | | | |
| Saligren | • | | | | | | |
| Salmeterol | | | | • | | | |
| salmeterol xinafoate | | | | • | | | |
| Samarium Sm 153 lexidronam | | | | | • | | |
| Sarpogrelate | | | | | | | • |
| Savella | | | | • | | | • |
| SB 206553 | | | | | | | • |
| Sch 23982 | | • | | | | | |
| Sch-23982 | | • | | | | | |
| scopolamine | • | | | | | | |
| scopolamine butylbromide | • | | | | | | |
| Scopolamine hydrobromide | • | | | | | | |
| Sdz 205,557 | | | | | | | • |
| Secoverine | • | | | | | | |
| SECOVERINE HYDROCHLORIDE | • | | | | | | |
| Selecal | | | | • | | | |
| selegiline | • | | | | | | |
| Selegiline hydrochloride | • | | | | | | |
| Selozok | | | | • | | | |
| Serc | | | • | | | | |
| Serotone | | | | | | | • |
| serotonin | | | | | | | • |
| sertraline | | | | | | | • |
| Sertraline hydrochloride | | | | | | | • |
| Setoperone | | | | | | | • |
| Sgd 101-75 | | | | • | | | |
| Silomat | | | | | | • | |
| Sinemet | • | • | | | | | |
| SKF 38393 | | • | | | | | |
| SKF 38393 hydrochloride | | • | | | | | |
| SKF 81297 | | • | | | | | |
| Skf 83566 | | • | | | | | |
| SKF 91488 | | | • | | | | |
| SKF 91488 dihydrochloride | | | • | | | | |
| Sm-Edtmp | | | | | • | | |
| SMR000449272 | | | | | | | • |
| Snc80 | | | | | • | | |
| Solifenacin | • | | | | | | |
| Solifenacin succinate | • | | | | | | |
| Sordinol | | • | | | | | |
| sotalol | | | | • | | | |
| Sotalol hydrochloride | | | | • | | | |
| Soventol | | | • | | | | |
| Soventol (TN) | | | • | | | | |
| Soventol hydrochloride | | | • | | | | |
| Spasril | • | | | | | | |
| Spectrum_001815 | | | | • | | | |
| spiperone | | • | | | | | |
| Spiriva | • | | | | | | |
| Spiriva Handihaler | • | | | | | | |
| Spiroxatrine | | • | | | | | |
| SQ 10643 | | | | | | | • |
| SR 59230A | | | | • | | | |
| ST 91 | • | | | • | | | |
| Stadol | | | | | • | • | |
| Stelazine | | • | | | | | |
| stepholidine | | • | | | | | |
| STP (hallucinogen) | | | | | | | • |
| Strattera | | | | • | | | |
| subecholine | • | | | | | | |
| Suberyldicholine | • | | | | | | |
| SUFENTANIL | | | | | • | | |
| Sufentanil citrate | | | | | • | | |
| sulpiride | | • | | | | | |
| Sultopride | | • | | | | | |
| sultopride hydrochloride | | • | | | | | |
| sumatriptan | | | | | | | • |
| SUMATRIPTAN SUCCINATE | | | | | | | • |
| Suplatast Tosilate | | | • | | | | |
| Sympatholytin | | | | • | | | |
| Synephrine | | | | • | | | |
| T123_SIGMA | | • | | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Tacrine | • | | | | | | |
| Tacrine hydrochloride | • | | | | | | |
| Tacrine hydrochloride hydrate | • | | | | | | |
| tageflar | | | | • | | | |
| Talacen | | | | | | • | |
| Talinolol | | | | • | | | |
| Talipexole | | • | | • | | | |
| Talwin | | | | | | • | |
| Talwin 50 | | | | | | • | |
| TAMSULOSIN | | | | • | | | |
| tandospirone citrate | | | | | | | • |
| Tbhpbo | | | | • | | | |
| TCMDC-125509 | • | | | | | | |
| Tegaserod maleate | | | | | | | • |
| Telenzepine | • | | | | | | |
| Teletux | | | | | | • | |
| TEMELASTINE | | | • | | | | |
| Tempium | • | | | | | | |
| Tenamfetamine | | | | • | | | • |
| terazosin | | | | • | | | |
| Terazosin hydrochloride | | | | • | | | |
| terbutaline | | | | • | | | |
| TERBUTALINE HEMISULFATE | | | | • | | | |
| Terbutaline sulfate | | | | • | | | |
| terfenadine | | | • | | | | |
| terguride | | • | | | | | |
| Terodiline | • | | | | | | |
| TERODILINE HYDROCHLORIDE | • | | | | | | |
| Tersigat | • | | | | | | |
| TERTATOLOL | | | | • | | | |
| Tesmilifene | | | • | | | | |
| TETRABENAZINE | | | | • | | | |
| TETRAHYDROCANNABINOL | | | | | • | | |
| tetrahydropalmatine | | • | | • | • | | |
| Tetraspasmin-Lefa | • | | | | | | |
| TFMPP | | | | | | | • |
| Thecodinum | | | | | | • | |
| Thephorin hydrochloride | | | • | | | | |
| Theratuss | | | | | | • | |
| thiethylperazine | | • | | | | | |
| Thiethylperazine maleate | | • | | | | | |
| Thioperamide | | | • | | | | |
| thioridazine | | • | | | | | |
| Thioridazine hydrochloride | | • | | | | | |
| thiothixene | | • | | | | | |
| thonzylamine | | | • | | | | |
| THONZYLAMINE HYDROCHLORIDE | | | • | | | | |
| tiapride | | • | | | | | |
| TILIDINE | | | | | • | | |
| Tilisolol | | | | • | | | |
| timolol | | | | • | | | |
| Timolol hemihydrate | | | | • | | | |
| Timolol maleate | | | | • | | | |
| TIOTIDINE | | | • | | | | |
| Tiotixene | | • | | | | | |
| Tiotropium | • | | | | | | |
| TIOTROPIUM BROMIDE | • | | | | | | |
| TIPP | | | | | • | | |
| Tiropramide | • | | | | | | |
| tizanidine | • | | | • | | | |
| Tizanidine hydrochloride | • | | | • | | | |
| Tobanum | | | | • | | | |
| Tocodilydrin | | | | • | | | |
| tolazoline | | | | • | | | |
| Tolazoline hydrochloride | | | | • | | | |
| Tolcapone | | • | | | | | |
| tolfenamic acid | | | | | | | • |
| tolterodine | • | | | | | | |
| Tolterodine tartrate | • | | | | | | |
| Torecan | | • | | | | | |
| Tramadol | | | | | • | | |
| tramadol hydrochloride | | | | | • | | |
| tranilast | | | • | | | | |
| Traxanox | | | • | | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Traxanox sodium | | | • | | | | |
| trazodone | | | | | | | • |
| Trazodone hydrochloride | | | | | | | • |
| Tremblex | • | | | | | | |
| Tretoquinol | | | | • | | | |
| Tricodein | | | | | • | • | |
| trifluoperazine | | • | | | | | |
| Trifluoperazine dihydrochloride | | • | | | | | |
| Trifluperidol | | • | | | | | |
| triflupromazine | | • | | | | | |
| Triflupromazine hydrochloride | | • | | | | | |
| TRIMAZOSIN | | | | • | | | |
| trimebutine | • | | | | | | |
| Trimebutine maleate | • | | | | | | |
| Trimeperidine | | | | | • | | |
| Trimethoquinol | | | | • | | | |
| trimipramine | | | | • | | | |
| Trimipramine maleate | | | | • | | | |
| tripelennamine | | | • | | | | |
| Tripelennamine citrate | | | • | | | | |
| Tripelennamine hydrochloride | | | • | | | | |
| triprolidine | | | • | | | | |
| Triprolidine hydrochloride | | | • | | | | |
| tropicamide | • | | | | | | |
| Tropine tropate | • | | | | | | |
| tropisetron | | | | | | | • |
| TROPISETRON HCl | | | | | | | • |
| Tropyl 3,5-dichlorobenzoate | | | | | | | • |
| trospium chloride | • | | | | | | |
| tulobuterol | | | | • | | | |
| Tulobuterol hydrochloride | | | | • | | | |
| Tuscodin | | | | | • | | |
| tyramine | | | | • | | | |
| Tyr-D-Ala-Gly-N-Methyl-Phe-Gly-ol | | | | | • | | |
| Tyr-tic-phe-phe-OH | | | | | • | | |
| UNII-7LG286J8GV | | | | | • | | |
| urapidil | | | | • | | | • |
| Uroxatral | | | | • | | | |
| Valoron | | | | | • | | |
| Vanoxeamine | | • | | | | | |
| Vanoxerine | | • | | | | | |
| venlafaxine | | | | | | | • |
| Ventipulmin | | | | • | | | |
| Ventolin | | | | • | | | |
| Verton | | | | • | | | |
| viloxazine | | | | • | | | |
| Viloxazine hydrochloride | | | | • | | | |
| Vistaril | | | • | | | | |
| Volinanserin | | | | | | | • |
| Vuf 9153 | | | • | | | | |
| Way 100635 | | | | | | | • |
| Way-100135 | | | | | | | • |
| Win-35428 | | • | | | | | |
| wortmannin | | | | | | | • |
| Wyamine sulfate | | | | • | | | |
| Xamoterol | | | | • | | | |
| Xamoterol hemifumarate | | | | • | | | |
| XANOMELINE | • | | | | | | |
| Xanomeline tartrate | • | | | | | | |
| xylamidine | | | | | | | • |
| Xylamidine tosylate | | | | | | | • |
| xylazine | | | | • | | | |
| Xylazine hydrochloride | | | | • | | | |
| Xyzall | | | • | | | | |
| Yohimbine | | | | • | | | |
| YOHIMBINE HYDROCHLORIDE | | | | • | | | |
| Zacopride | | | | | | | • |
| ZACOPRIDE HYDROCHLORIDE | | | | | | | • |
| ZATOSETRON | | | | | | | • |
| ZATOSETRON MALEATE | | | | | | | • |
| Zebeta | | | | • | | | |
| Zelmac | | | | | | | • |
| Zelnorm | | | | | | | • |
| Zeneca ZD7114 | | | | • | | | |

TABLE 1-continued

Neurotransmitter receptor modulating agents

| Low Molecular Weight Compound | Muscarinic | Dopaminergic | Histaminergic | Adrenergic | Opioid | Antitussive | Serotonergic |
|---|---|---|---|---|---|---|---|
| Zetidoline | • | | | | | | |
| Zimeldine | | | | | | | • |
| Zimeldine hydrochloride | | | | | | | • |
| Zimelidine | | | | | | | • |
| Zimelidine dihydrochloride | | | | | | | • |
| ZINTEROL | | | | • | | | |
| ZINTEROL HYDROCHLORIDE | | | | • | | | |
| Zipeprol | | | | | | • | |
| Ziprasidone | | • | | | | | • |
| Ziprasidone hydrochloride | | • | | | | | • |
| Ziprasidone mesylate | | • | | | | | |
| Zofran | | | | | | | • |
| Zolantidine | | | • | | | | |
| zolmitriptan | | | | | | | • |
| Zuclopenthixol | | • | | | | | |
| Zyrtec | | | • | | | | |

1. Muscarinic Receptor Antagonists

A muscarinic receptor is a G-protein coupled acetylcholine receptor. There are five known subtypes of muscarinic receptors: $M_1$ receptors, $M_2$ receptors, $M_3$ receptors, $M_4$ receptors, and $M_5$ receptors. A muscarinic receptor antagonist is an agent able to inhibit one or more characteristic responses of a muscarinic receptor or receptor subtype. As a non-limiting example, an antagonist may competitively or non-competitively bind to (1) a muscarinic receptor, (2) an agonist or partial agonist (or other ligand) of the muscarinic receptor, and/or (3) a downstream signaling molecule to inhibit the muscarinic receptor's function. As shown in the Examples, benztropine, carbetapentane, clemastine, ipratropium, and atropine have been shown to antagonize the function of a muscarinic receptor and/or are known antagonists of a muscarinic receptor. Therefore, in some embodiments, the muscarinic receptor antagonist is a compound selected from benztropine, carbetapentane, clemastine, ipratropium, atropine, and salts, prodrugs, racemic mixtures, conformational and/or optical isomers, crystalline polymorphs, and isotopic variants thereof. Alternatively, any of the muscarinic receptor modulators listed in Table 1 can be used to antagonize a muscarinic receptor. Thus, in some embodiments, the muscarinic receptor antagonist is a muscarinic receptor modulator compound listed in Table 1. The compounds described in Table 1 are readily available.

In some embodiments, the neurotransmitter receptor modulating agent is benztropine or a salt thereof (e.g., benztropine mesylate). In some embodiments, the neurotransmitter receptor modulating agent is clemastine or a salt thereof (e.g., clemastine fumarate).

2. Dopamine Receptor Antagonists

A dopamine receptor is a G-protein coupled receptor, for which the neurotransmitter dopamine is the primary endogenous ligand. There are five known subtypes of dopamine receptors: $D_1$ and $D_5$ receptors, the $D_1$-like receptors, activate adenylyl cyclase, while the $D_2$, $D_3$, and $D_4$ receptors, the $D_2$-like receptors, inhibit adenylyl cyclase and activate $K^+$ channels. A dopamine receptor antagonist is an agent able to inhibit one or more characteristic responses of a dopamine receptor or receptor subtype. As a non-limiting example, an antagonist may competitively or non-competitively bind to (1) a dopamine receptor, (2) an agonist or partial agonist (or other ligand) of the dopamine receptor, and/or (3) a downstream signaling molecule to inhibit the dopamine receptor's function. As shown in the Examples, benztropine, GBR12935, and trifluoperazine have been shown to antagonize the function of a dopamine receptor and/or are known antagonists of a dopamine receptor. Therefore, in some embodiments, the dopamine receptor antagonist is a compound selected from benztropine, GBR12935, trifluoperazine, and salts, prodrugs, racemic mixtures, conformational and/or optical isomers, crystalline polymorphs, and isotopic variants thereof. Alternatively, any of the dopamine receptor modulators listed in Table 1 can be used to antagonize a dopamine receptor. Thus, in some embodiments, the dopamine receptor antagonist is a dopamine receptor modulator compound listed in Table 1. The compounds described in Table 1 are readily available.

In some embodiments, the neurotransmitter receptor modulating agent is benztropine or a salt thereof (e.g., benztropine mesylate). In some embodiments, the neurotransmitter receptor modulating agent is trifluoperazine or a salt thereof (e.g., trifluoperazine hydrochloride).

3. Histamine Receptor Antagonists

A histamine receptor is a G-protein coupled receptor, for which the neurotransmitter histamine is the primary endogenous ligand. There are four known subtypes of histamine receptors: $H_1$ receptors, $H_2$ receptors, $H_3$ receptors, and $H_4$ receptors. A histamine receptor antagonist is an agent able to inhibit one or more characteristic responses of a histamine receptor or receptor subtype. As a non-limiting example, an antagonist may competitively or non-competitively bind to (1) a histamine receptor, (2) an agonist or partial agonist (or other ligand) of the histamine receptor, and/or (3) a downstream signaling molecule to inhibit the histamine receptor's function. As shown in the Examples, clemastine has been shown to antagonize the function of a histamine receptor. Therefore, in some embodiments, the histamine receptor antagonist is clemastine or a salt, prodrug, racemic mixture, conformational and/or optical isomer, crystalline polymorph, or isotopic variant thereof. Alternatively, any of the histamine receptor modulators listed in Table 1 can be used to antagonize a histamine receptor. Thus, in some embodiments, the histamine receptor antagonist is a histamine receptor modulator compound listed in Table 1. The compounds described in Table 1 are readily available.

In some embodiments, the neurotransmitter receptor modulating agent is clemastine or a salt thereof (e.g., clemastine fumarate).

4. Beta Adrenergic Receptor Modulators

A beta adrenergic receptor is a subtype of the adrenergic receptor, a G-protein coupled receptor, for which catecholamines (e.g., epinephrine and norepinephrine) are the primary endogenous ligand. There are three known subtypes of beta adrenergic receptors: $\beta_1$ receptors, $\beta_2$ receptors, and $\beta_3$ receptors. A beta adrenergic receptor antagonist is an agent able to inhibit one or more characteristic responses of a beta adrenergic receptor or receptor subtype. As a non-limiting example, an antagonist may competitively or non-competitively bind to (1) a beta adrenergic receptor, (2) an agonist or partial agonist (or other ligand) of the beta adrenergic receptor, and/or (3) a downstream signaling molecule to inhibit the beta adrenergic receptor's function. As a non-limiting example, pindolol is able to antagonize the function of a beta adrenergic receptor. A beta adrenergic receptor agonist is an agent able to induce or stimulate one or more characteristic responses of a beta adrenergic receptor or receptor subtype. As shown in the Examples, pindolol, salmeterol, salbutamol, and albuterol have been shown to agonize the function of a beta adrenergic receptor and/or are known agonists of a beta adrenergic receptor. Therefore, in some embodiments, the beta adrenergic receptor modulator is a compound selected from pindolol, salmeterol, salbutamol, albuterol, and salts, prodrugs, racemic mixtures, conformational and/or optical isomers, crystalline polymorphs, and isotopic variants thereof. Alternatively, any of the beta adrenergic receptor modulators listed in Table 1 can be used to modulate a beta adrenergic receptor. Thus, in some embodiments, the beta adrenergic receptor modulator is a beta adrenergic receptor modulator compound listed in Table 1. The compounds described in Table 1 are readily available.

In some embodiments, the neurotransmitter receptor modulating agent is salmeterol or a salt thereof (e.g., salmeterol xinfoate). In some embodiments, the neurotransmitter receptor modulating agent is salbutamol or a salt thereof (e.g., salbutamol hemisulfate).

5. Opioid Receptor Modulators

An opioid receptor is a G-protein coupled receptor, for which opioids are the primary endogenous ligand. An opioid receptor antagonist is an agent able to inhibit one or more characteristic responses of an opioid receptor or receptor subtype. As a non-limiting example, an antagonist may competitively or non-competitively bind to (1) an opioid receptor, (2) an agonist or partial agonist (or other ligand) of a receptor, and/or (3) a downstream signaling molecule to inhibit a receptor's function. An opioid receptor agonist is an agent able to induce or stimulate one or more characteristic responses of an opioid receptor or receptor subtype. For example, an agonist may activate an opioid receptor. As shown in the Examples, carbetapentane, Snc-80, and BD-1047 have been shown to modulate the function of an opioid receptor. Therefore, in some embodiments, the opioid receptor antagonist is a compound selected from carbetapentane, Snc-80, BD-1047, and salts, prodrugs, racemic mixtures, conformational and/or optical isomers, crystalline polymorphs, and isotopic variants thereof. Alternatively, any of the opioid receptor modulators listed in Table 1 can be used to modulate an opioid receptor. Thus, in some embodiments, the opioid receptor modulator is an opioid receptor modulator compound listed in Table 1. The compounds described in Table 1 are readily available.

B. Identification of Modulating Agents

A number of different screening protocols can be utilized to identify agents that stimulate increased myelination of nerves. In general terms, the screening methods involve screening a plurality of agents to identify an agent that increases the number of cells in a sample having a differentiated, myelinating cell fate (e.g., mature myelinating oligodendrocyte). In some embodiments, an agent promotes or increases OPC differentiation when it increases the percentage of OPCs (e.g., in a sample comprising a plurality of OPCs) that differentiate to a mature myelinating cell fate by at least about 5%, 10%, 15%, 20%, 25%, 30%, 40%, 50%, or more as compared to the percentage of OPCs that differentiate to a mature myelinating cell fate in the absence of the agent.

1. Marker Assays

In some embodiments, agents that stimulate increased myelination of nerves are identified by screening for induction of markers of mature myelinating oligodendrocytes. In some embodiments, samples comprising a plurality of OPCs are contacted with a candidate agent, incubated under conditions suitable for the differentiation of OPCs, and evaluated for the presence or absence of one or more markers of mature myelinating oligodendrocytes. Examples of markers of mature myelinating oligodendrocytes include, but are not limited to, myelin basic protein (MBP), myelin oligodendrocyte glycoprotein (MOG), 2'3'-cyclic-nucleotide 3' phosphodiesterase (CNP), GalC, O1, or O4.

Markers of mature myelinating oligodendrocytes can be detected using any number of established analytical techniques. For example, detection can be accomplished by detecting nucleic acid (e.g., by in situ hybridization or RT-PCR) or protein (e.g., by immunoassay or Western blot analysis) levels, followed by visualization and/or quantification using any one of a variety of methods known in the art. In some embodiments, a marker of mature myelinating oligodendrocytes is detected by in situ hybridization. In situ hybridization techniques are generally described in *In Situ Hybridization: A Practical Approach* (Wilkinson, D. G., ed.), Oxford University Press, 1992. In some embodiments, a marker of mature myelinating oligodendrocytes is detected by immunoassay. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. In some embodiments, the immunoassay is an immunofluorescence assay.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

2. Cells and Reagents

The primary screens for identifying agents that induce OPC differentiation and/or stimulate increased myelination of nerves can be performed in cell-based assays using cultured OPC cell lines or OPCs derived from a subject (e.g., from a mammal).

OPCs can be derived from any of a variety of sources. In some embodiments, OPCs are harvested from a tissue, for example, brain tissue, spinal cord tissue, or optic nerve tissue. The tissue can be from a rodent (e.g., rat or mouse), chicken, dog, cat, rabbit, cow, sheep, goat, or primate (e.g., a monkey, a chimpanzee, or a human). In some embodiments, OPCs are derived from fetal tissue. In some embodiments, OPCs are derived from adult tissue. Alternatively, OPCs can be derived from culturing stem cells (e.g., neural stem cells or embryonic stem cells) or from other cells that can be induced to give rise to OPCs (e.g., bone marrow stromal cells).

Examples of conditions suitable for OPC differentiation are described in the Examples section below. Cell culture conditions are described in more detail, e.g., in Picot, *Human Cell Culture Protocols (Methods in Molecular Medicine)* 2010 ed., and in Davis, *Basic Cell Culture* 2002 ed. OPCs are cultured with growth factor, for example, PDGFαα. As a non-limiting example, OPCs are proliferated in culture on poly-D-Lysine coated cell culture dishes using OPC media (Neurobasal media, B27 supplement without vitamin A, non-essential amino acids) containing 30 ng/mL PDGFαα. For differentiation, OPCs are seeded on poly-D-Lysine coated cell culture dishes using OPC media containing 2 ng/mL PDGFαα and treated with compounds dissolved in DMSO (<1% final concentration). Differentiating OPCs are incubated at 37° C., 5% $CO_2$ for 6 days. At the end of 6 days, cells are fixed with 4% paraformaldehyde for immunofluorescence analysis or are harvested for biochemical analysis.

3. Candidate Agents

The agents that are screened for the ability to promote OPC differentiation can be any small chemical compound, or a biological entity, such as a polypeptide, sugar, nucleic acid or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Bio-chemica Analytika (Buchs, Switzerland) and the like.

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a Log P over 5 (or M Log P over 4.15); and/or having more than 10 H-bond acceptors (expressed as the sum of Ns and Os). See, e.g., Lipinski et al., *Adv Drug Delivery Res* 23:3-25 (1997). Compound classes that are substrates for biological transporters are typically exceptions to the rule.

In some embodiments, the agents are from a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks." For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 1522 (1996) and U.S. Pat. No. 5,593, 853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

In some embodiments, candidate agents are able to penetrate the blood-brain barrier. In some embodiments, candidate agents have a low molecular weight (i.e., a molecular weight of no more than 800 kDa). In some embodiments, candidate agents are screened for one or more other criteria, such as toxicity or brain pharmacokinetics.

4. Validation

Agents that are initially identified by any of the foregoing screening methods can be further tested to validate the apparent activity. In some embodiments, validation assays are in vitro assays. In some embodiments, such studies are conducted with suitable animal models. The basic format of such methods involves administering a lead compound identified during an initial screen to an animal that serves as a disease model for humans and then determining if the disease (e.g., a demyelinating disease) is in fact modulated and/or the disease or condition is ameliorated. The animal models utilized in validation studies generally are mammals of any kind. Specific examples of suitable animals include, but are not limited to, primates, mice, rats and zebrafish.

III. Methods Using Neurotransmitter Receptor Modulating Agents

The neurotransmitter receptor modulating agents described herein can be used in various therapeutic and/or prophylactic methods. In one aspect, the present invention provides methods of inducing oligodendrocyte precursor cell (OPC) differentiation to a mature myelinating cell fate (e.g., myelinating oligodendrocytes). In some embodiments, the method comprises contacting the OPC with a neurotransmitter receptor modulating agent as described herein and culturing the OPC under conditions suitable for OPC differentiation. In some embodiments, the neurotransmitter receptor modulating agent is selected from a muscarinic receptor antagonist, a dopamine receptor antagonist, a histamine receptor antagonist, a beta adrenergic receptor modulator, and an opioid receptor modulator. In some embodiments, the OPC is cultured in the presence of the neurotransmitter receptor modulating agent for at least 2 days, at least 3 days, at least 4 days, at least 5 days, at least 6 days or longer under conditions suitable for OPC differentiation. Differentiation to a mature myelinating cell fate can be determined by detecting the presence of one or more biological markers of mature myelinating oligodendrocytes. Marker assays for detecting the presence or level of myelinating oligodendrocytes are described herein, for example in Section II(B) above.

In another aspect, the present invention provides methods of stimulating increased myelination of nerves in a subject in need thereof. In some embodiments, the method comprises administering to the subject a neurotransmitter receptor modulating agent as described herein; thereby stimulating increased myelination of nerves in the subject. In some embodiments, the neurotransmitter receptor modulating agent is a compound selected from a muscarinic receptor antagonist, a dopamine receptor antagonist, a histamine receptor antagonist, a beta adrenergic receptor modulator, and an opioid receptor modulator.

In some embodiments, a subject in need of a method of stimulating increased myelination of nerves is a subject having a demyelinating disease. Thus, in yet another aspect, the present invention provides methods of treating and/or ameliorating a subject having a demyelinating disease. In some embodiments, a subject in need of a method of stimulating increased myelination of nerves is a subject at risk of having a demyelinating disease. Thus, in yet another aspect, the present invention provides methods of preventing a demyelinating disease or delaying the occurrence of a demyelinating disease.

In some embodiments, the method comprises administering to the subject a neurotransmitter receptor modulating agent selected from a muscarinic receptor antagonist, a dopamine receptor antagonist, a histamine receptor antagonist, a beta adrenergic receptor modulator, and an opioid receptor modulator. In some embodiments, the neurotransmitter receptor modulating agent is a compound listed in Table 1 (e.g., a muscarinic receptor modulator compound, dopamine receptor modulator compound, histamine receptor modulator compound, beta adrenergic receptor modulator compound, or opioid receptor modulator compound listed in Table 1). In some embodiments, the neurotransmitter receptor modulating agent is benztropine, cerbetapentane, clemastine, pindolol, ipratropium, atropine, GBR12935, Snc-80, BD-1047, salmeterol, albuterol, or trifluoperazine, or a salt thereof. In some embodiments, the neurotransmitter receptor modulating agent is benztropine, clemastine, salmeterol, salbutamol, trifluoperazine, or a salt thereof. In some embodiments, the neurotransmitter receptor modulating agent is benztropine or a salt thereof (e.g., benztropine mesylate).

In some embodiments, the demyelinating disease is multiple sclerosis, idiopathic inflammatory demyelinating disease, transverse myelitis, Devic's disease, progressive multifocal leukoencephalopathy, optic neuritis, leukodystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or human T-cell lymphotropic virus (HTLV)-associated myelopathy.

In some embodiments, the demyelinating disease is multiple sclerosis (MS). There are several subtypes of MS, including relapsing-remitting multiple sclerosis (RRMS), secondary progressive multiple sclerosis (SPMS), primary progressive multiple sclerosis (PPMS), and progressive relapsing multiple sclerosis (PRMS). In some embodiments, the subject has RRMS. In some embodiments, the subject has SPMS. In some embodiments, the subject has PPMS. In some embodiments, the subject has PRMS. A subject may initially be diagnosed as having one subtype of MS (e.g., RRMS), and subsequently the subtype of MS afflicting the subject may convert to another subtype of MS (e.g., from RRMS to SPMS). It is contemplated that the methods of the present invention can be applied to treat a subject whose subtype of MS converts to another subtype of MS.

In some embodiments, a subject in need thereof (e.g., a subject having a demyelinating disease or at risk for having a demyelinating disease) is administered a neurotransmitter receptor modulating agent in combination with at least one other therapy. In some embodiments, the at least one other therapy is an immunomodulatory agent. As used herein, an "immunomodulatory agent" refers to a disease-modifying drug which alters the course of a demyelinating disease (e.g., multiple sclerosis, idiopathic inflammatory demyelinating disease, transverse myelitis, Devic's disease, progressive multifocal leukoencephalopathy, optic neuritis, leukodystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or HTLV-associated myelopathy).

In some embodiments, an immunomodulatory agent is a disease-modifying drug that alters the course of multiple sclerosis (e.g., RRMS, SPMS, PPMS, or PRMS). For example, a disease-modifying drug can reduce the frequency or severity of an MS relapse and/or reduce development of lesions or scars at regions of demyelination. In some embodiments, an immunomodulatory agent is an immunosuppressant (i.e., an agent that suppresses or prevents an immune response). In some embodiments, an immunomodulatory agent is an agent that modulates an immune response (e.g., by stimulating the induction of suppressor T cells). Examples of immunomodulatory agents for the treatment of MS include, but are not limited to, interferons (e.g., interferon-β, e.g., interferon beta-1a or interferon beta-1b), glatiramer acetate, mitoxantrone, fingolimod (FTY720), or monoclonal antibodies (e.g., natalizumab, rituximab, daclizumab, or alemtuzumab). Thus, in some embodiments, the method of the present invention comprises administering to a subject having MS a neurotransmitter receptor modulating agent (e.g., a compound selected from a muscarinic receptor antagonist, a dopamine receptor antagonist, a histamine receptor antagonist, a beta adrenergic receptor antagonist, and an opioid receptor modulator) in combination with fingolimod (FTY720), interferon beta-1a, interferon beta-1b, glatiramer acetate, mitoxantrone, natalizumab, rituximab, daclizumab, or alemtuzumab.

In another aspect, the present invention provides methods of enhancing the therapeutic effect of an immunomodulatory agent in a subject in need thereof. It has been surprisingly found that in mouse models of demyelinating disease, administering a combination of a neurotransmitter receptor modulating agent and an immunomodulatory agent results in a significantly larger decrease in the clinical severity of the demyelinating disease as compared to the decrease in the clinical severity of the demyelinating disease that can be achieved with either the neurotransmitter receptor modulating agent or the immunomodulatory agent alone. Thus, in some embodiments, the method comprises administering to a subject an immunomodulatory agent and a neurotransmitter receptor modulating agent; thereby enhancing the therapeutic effect of the immunomodulatory agent in the subject. In some embodiments, the subject has a demyelinating disease or is at risk of having a demyelinating disease.

Furthermore, it has also surprisingly been found that administering a neurotransmitter receptor modulating agent, in combination with an immunomodulatory agent at a dose that, on its own, is insufficient to be therapeutic for the treatment of a demyelinating disease, results in a therapeutic effect that is greater than the therapeutic effect from administering each agent alone. Thus, in another aspect, the present invention provides methods of treating a subject in need thereof by administering an immunomodulatory agent and a neurotransmitter receptor modulating agent, wherein the immunomodulatory agent is administered at a subtherapeutic dose. In some embodiments, the subject has a demyelinating disease or is at risk of having a demyelinating disease.

In some embodiments, the demyelinating disease is multiple sclerosis, idiopathic inflammatory demyelinating disease, transverse myelitis, Devic's disease, progressive multifocal leukoencephalopathy, optic neuritis, leukodystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or HTLV-associated myelopathy. In some embodiments, the demyelinating disease is multiple sclerosis, e.g., relapsing-remitting multiple sclerosis (RRMS), secondary progressive multiple sclerosis (SPMS), primary progressive multiple sclerosis (PPMS), or progressive relapsing multiple sclerosis (PRMS). In some embodiments, the subject is initially diagnosed as having one subtype of MS (e.g., RRMS), and subsequently the subtype of MS afflicting the subject converts to another subtype of MS (e.g., from RRMS to SPMS).

In some embodiments, the neurotransmitter receptor modulating agent is selected from a muscarinic receptor antagonist, a dopamine receptor antagonist, a histamine receptor antagonist, a beta adrenergic receptor modulator, and an opioid receptor modulator, and the immunomodulatory agent is selected from fingolimod (FTY720), interferon beta-1a, interferon beta-1b, glatiramer acetate, mitoxantrone, natalizumab, rituximab, daclizumab, and alemtuzumab. In some embodiments, the neurotransmitter receptor modulating agent is a muscarinic receptor modulator compound, a dopamine receptor modulator compound, a histamine receptor modulator compound, a beta adrenergic receptor modulator compound, or an opioid receptor modulator compound listed in Table 1, and the immunosuppressant is fingolimod (FTY720), interferon beta-1a, interferon beta-1b, glatiramer acetate, mitoxantrone, natalizumab, rituximab, daclizumab, or alemtuzumab. In some embodiments, the neurotransmitter receptor modulating agent is benztropine, clemastine, salmeterol, salbutamol, or trifluoperazine, or a salt thereof, and the immunomodulatory agent is fingolimod (FTY720), interferon beta-1a, interferon beta-1b, glatiramer acetate, mitoxantrone, natalizumab, rituximab, daclizumab, or alemtuzumab. In some embodiments, the neurotransmitter receptor modulating agent is benztropine and the immunomodulatory agent is fingolimod (FTY720), interferon beta-1a, or interferon beta-1b.

Therapeutic doses for the immunomodulatory agents fingolimod (FTY720), interferon beta-1a, interferon beta-1b, glatiramer acetate, mitoxantrone, and natalizumab are known in the art. See, e.g., Kappos et al., *N Engl J Med* 362:387-401 (2010); Cohen et al., *N Engl J Med* 362:402-15 (2010); Gottesman et al., *Mult Scler* 12:271-80 (2006); Hurwitz et al., *Clin Ther* 30:1102-12 (2008); Gaindh et al., *Expert Opin Biol Ther* 8:1823-29 (2008); Koch-Henriksen et al., *Neurology* 66:1056-60 (2006); Benatar, *Lancet* 360:1428 (2008); Jacobs et al., *Ann Neurol* 39:285-94 (1996); *Lancet* 352:1498-1504 (1998); Johnson et al., *Neurology* 45:1268-76 (1995); Johnson et al., *Neurology* 50:701-08 (1998); Comi et al., *Ann Neurol.* 69:75-82 (2011); Calabresi *Nat Clin Pract Neurol* 3:540-1 (2007); and Polman et al., *N Engl J Med* 354:899-910 (2006); the contents of each of which are incorporated by reference herein in their entirety.

In some embodiments, the immunomodulatory agent (e.g., fingolimod, interferon beta-1a, interferon beta-1b, glatiramer acetate, mitoxantrone, or natalizumab) is administered at a therapeutically effective dose. In some embodiments, the immunomodulatory agent (e.g., fingolimod, interferon beta-1a, interferon beta-1b, glatiramer acetate, mitoxantrone, or natalizumab) is administered at a subtherapeutic dose, e.g., at a dose that is less than about 75%, less than about 70%, less than about 60%, less than about 50%, less than about 40%, less than about 30%, less than about 25%, less than about 20%, less than about 15%, less than about 10%, or less than about 5% of the dose that is conventionally administered for the immunomodulatory agent.

Fingolimod (FTY720) is conventionally administered at a therapeutically effective dose of from about 0.5 mg per day to about 1.5 mg per day (e.g., about 0.5, about 0.6, about 0.7, about 0.8, about 0.9, about 1.0, about 1.1, about 1.2, about 1.3, about 1.4, or about 1.5 mg per day). See, e.g., Kappos et al., *N Engl J Med* 362:387-401 (2010). Thus, in some embodiments, a subtherapeutic dose of fingolimod is from about 0.005 mg per day to about 0.375 mg per day (e.g., about 0.005, about 0.01, about 0.02, about 0.03, about 0.04, about 0.05, about 0.06, about 0.07, about 0.08, about 0.09, about 0.1, about 0.15, about 0.2, about 0.25, about 0.3, about 0.35, or about 0.375 mg per day).

Interferon beta-1a is conventionally administered at a therapeutically effective dose of about 30 μg per week. See e.g., Jacobs et al., *Ann Neurol* 39:285-94 (1996). Thus, in some embodiments, a subtherapeutic dose of interferon beta-1a is from about 0.3 µg per week to about 23 µg per week (e.g., about 0.3, about 0.5, about 0.75, about 1, about 2, about 3, about 4, about 5, about 6, about 7, about 8, about 9, about 10, about 11, about 12, about 13, about 14, about 15, about 16, about 17, about 18, about 19, about 20, about 21, about 22, or about 23 µg per week).

Interferon beta-1b is conventionally administered at a therapeutically effective dose of from about 250 µg every other day to about 500 µg every other day. See, e.g., Gottesman et al., *Mult Scler* 12:271-80 (2006). Thus, in some embodiments, a subtherapeutic dose of interferon beta-1b is from about 2 µg every other day to about 190 µg every other day (e.g., about 2, about 5, about 10, about 20, about 30, about 40, about 50, about 60, about 70, about 80, about 90, about 100, about 110, about 120, about 130, about 140, about 150, about 160, about 170, about 180, or about 190 µg every other day).

In some embodiments, the neurotransmitter receptor modulating agent (e.g., a muscarinic receptor antagonist, a dopamine receptor antagonist, a histamine receptor antagonist, a beta adrenergic receptor modulator, or an opioid receptor modulator listed in Table 1) is administered at a therapeutically effective dose. In some embodiments, the neurotransmitter receptor modulating agent (e.g., muscarinic receptor antagonist, dopamine receptor antagonist, histamine receptor antagonist, beta adrenergic receptor modulator, or opioid receptor modulator listed in Table 1) is administered at a subtherapeutic dose, e.g., at a dose that is less than about 75%, less than about 70%, less than about 60%, less than about 50%, less than about 40%, less than about 30%, less than about 25%, less than about 20%, less than about 15%, less than about 10%, or less than about 5% of the dose that is conventionally administered for the neurotransmitter receptor modulating agent. In some embodiments, the neurotransmitter receptor modulating agent that is administered at a therapeutically effective dose or at a subtherapeutic dose is benztropine, clemastine, salmeterol, salbutamol, trifluoperazine, or a salt thereof. In some embodiments, the neurotransmitter receptor modulating agent that is administered at a therapeutically effective dose or at a subtherapeutic dose is benztropine or a salt thereof (e.g., benztropine mesylate). As a non-limiting example, a therapeutically effective dose of benztropine may be from about 1 mg per day to about 10 mg per day (e.g., about 1, about 2, about 3, about 4, about 5, about 6, about 7, about 8, about 9, or about 10 mg per day). Thus, in some embodiments, a subtherapeutic dose of benztropine may be from about 0.01 mg per day to about 0.75 mg per day (e.g., about 0.01, about 0.05, about 0.10, about 0.015, about 0.20, about 0.25, about 0.30, about 0.35, about 0.40, about 0.45, about 0.50, about 0.55, about 0.60, about 0.65, about 0.70, or about 0.75 mg per day).

In some embodiments, a neurotransmitter receptor modulating agent (e.g., a muscarinic receptor antagonist, a dopamine receptor antagonist, a histamine receptor antagonist, a beta adrenergic receptor modulator, or an opioid receptor modulator listed in Table 1, e.g., benztropine, clemastine, salmeterol, salbutamol, trifluoperazine, or a salt thereof) is administered at a therapeutically effective dose and an immunomodulatory agent (e.g., fingolimod, interferon beta-1a, interferon beta-1b, glatiramer acetate, mitoxantrone, or natalizumab) is administered at a therapeutically effective dose. In some embodiments, the neurotransmitter receptor modulating agent is benztropine or a salt thereof (e.g., benztropine mesylate) and the immunomodulatory agent is fingolimod (FTY720), interferon beta-1a, or interferon beta-1b. In some embodiments, benztropine is administered at a therapeutically effective dose of from about 1 mg per day to about 10 mg per day; fingolimod is administered at a therapeutically effective dose of from about 0.5 mg per day to about 1.5 mg per day; interferon beta-1a is administered at a therapeutically effective dose of about 30 µg per week; and/or interferon beta-1b is administered at a therapeutically effective dose of from about 250 µg every other day to about 500 µg every other day.

In some embodiments, a neurotransmitter receptor modulating agent (e.g., a muscarinic receptor antagonist, a dopamine receptor antagonist, a histamine receptor antagonist, a beta adrenergic receptor modulator, or an opioid receptor modulator listed in Table 1, e.g., benztropine, clemastine, salmeterol, salbutamol, trifluoperazine, or a salt thereof) is administered at a therapeutically effective dose and an immunomodulatory agent (e.g., fingolimod, interferon beta-1a, interferon beta-1b, glatiramer acetate, mitoxantrone, or natalizumab) is administered at a subtherapeutic dose, e.g., at a dose that is less than about 75%, less than about 70%, less than about 60%, less than about 50%, less than about 40%, less than about 30%, less than about 25%, less than about 20%, less than about 15%, less than about 10%, or less than about 5% of the dose that is conventionally administered for the immunomodulatory agent. In some embodiments, the neurotransmitter receptor modulating agent is benztropine or a salt thereof (e.g., benztropine mesylate) and the immunomodulatory agent is fingolimod (FTY720), interferon beta-1a, or interferon beta-1b. In some embodiments, benztropine is administered at a therapeutically effective dose of from about 1 mg per day to about 10 mg per day; fingolimod is administered at a subtherapeutic dose of from about 0.005 mg per day to about 0.375 mg per day; interferon beta-1a is administered at a subtherapeutic dose of from about 0.3 µg per week to about 23 µg per week; and/or interferon beta-1b is administered at a subtherapeutic dose of from about 2 µg every other day to about 190 µg every other day.

In some embodiments, a neurotransmitter receptor modulating agent (e.g., muscarinic receptor antagonist, dopamine receptor antagonist, histamine receptor antagonist, beta adrenergic receptor modulator, or opioid receptor modulator listed in Table 1, e.g., benztropine, clemastine, salmeterol, salbutamol, trifluoperazine, or a salt thereof) is administered at a subtherapeutic dose, e.g., at a dose that is less than about 75%, less than about 70%, less than about 60%, less than about 50%, less than about 40%, less than about 30%, less than about 25%, less than about 20%, less than about 15%, less than about 10%, or less than about 5% of the dose that is conventionally administered for the neurotransmitter receptor modulating agent, and an immunomodulatory agent (e.g., fingolimod, interferon beta-1a, interferon beta-1b, glatiramer acetate, mitoxantrone, or natalizumab) is administered at a therapeutically effective dose. In some embodiments, the neurotransmitter receptor modulating agent is benztropine or a salt thereof (e.g., benztropine mesylate) and the immunomodulatory agent is fingolimod (FTY720), interferon beta-1a, or interferon beta-1b. In some embodiments, benztropine is administered at a subtherapeutic dose of from about 0.01 mg per day to about 0.75 mg per day; fingolimod is administered at a therapeutically effective dose of from about 0.5 mg per day to about 1.5 mg per day; interferon beta-1a is administered at a therapeutically effective dose of about 30 µg per week; and/or interferon beta-1b is administered at a therapeutically effective dose of from about 250 µg every other day to about 500 µg every other day.

In some embodiments, a neurotransmitter receptor modulating agent (e.g., muscarinic receptor antagonist, dopamine receptor antagonist, histamine receptor antagonist, beta adrenergic receptor modulator, or opioid receptor modulator listed in Table 1, e.g., benztropine, clemastine, salmeterol, salbutamol, trifluoperazine, or a salt thereof) is administered at a subtherapeutic dose, e.g., at a dose that is less than about 75%, less than about 70%, less than about 60%, less than about 50%, less than about 40%, less than about 30%, less than about 25%, less than about 20%, less than about 15%, less than about 10%, or less than about 5% of the dose that is conventionally administered for the neurotransmitter receptor modulating agent, and an immunomodulatory agent (e.g., fingolimod, interferon beta-1a, interferon beta-1b, glatiramer acetate, mitoxantrone, or natalizumab) is administered at a subtherapeutic dose, e.g., at a dose that is less than about 75%, less than about 70%, less than about 60%, less than about 50%, less than about 40%, less than about 30%, less than about 25%, less than about 20%, less than about 15%, less than about 10%, or less than about 5% of the dose that is conventionally administered for the immunomodulatory agent. In some embodiments, the neurotransmitter receptor modulating agent is benztropine or a salt thereof (e.g., benztropine mesylate) and the immunomodulatory agent is fingolimod (FTY720), interferon beta-1a, or interferon beta-1b. In some embodiments, benztropine is administered at a subtherapeutic dose of from about 0.01 mg per day to about 0.75 mg per day; fingolimod is administered at a subtherapeutic dose of from about 0.005 mg per day to about 0.375 mg per day; interferon beta-1a is administered at a subtherapeutic dose of from about 0.3 μg per week to about 23 μg per week; and/or interferon beta-1b is administered at a subtherapeutic dose of from about 2 μg every other day to about 190 μg every other day.

In some embodiments, a neurotransmitter receptor modulating agent (e.g., a muscarinic receptor antagonist, a dopamine receptor antagonist, a histamine receptor antagonist, a beta adrenergic receptor modulator, or an opioid receptor modulator listed in Table 1, e.g., benztropine, clemastine, salmeterol, salbutamol, trifluoperazine, or a salt thereof) is administered at a therapeutically effective dose and an immunomodulatory agent (e.g., fingolimod, interferon beta-1a, interferon beta-1b, glatiramer acetate, mitoxantrone, or natalizumab) is administered at a therapeutically effective dose for the treatment or prevention of a demyelinating disease (e.g., multiple sclerosis). In some embodiments, a neurotransmitter receptor modulating agent (e.g., a muscarinic receptor antagonist, a dopamine receptor antagonist, a histamine receptor antagonist, a beta adrenergic receptor modulator, or an opioid receptor modulator listed in Table 1, e.g., benztropine, clemastine, salmeterol, salbutamol, trifluoperazine, or a salt thereof) is administered at a therapeutically effective dose and an immunomodulatory agent (e.g., fingolimod, interferon beta-1a, interferon beta-1b, glatiramer acetate, mitoxantrone, or natalizumab) is administered at a subtherapeutic dose for the treatment or prevention of a demyelinating disease (e.g., multiple sclerosis). In some embodiments, a neurotransmitter receptor modulating agent (e.g., a muscarinic receptor antagonist, a dopamine receptor antagonist, a histamine receptor antagonist, a beta adrenergic receptor modulator, or an opioid receptor modulator listed in Table 1, e.g., benztropine, clemastine, salmeterol, salbutamol, trifluoperazine, or a salt thereof) is administered at a subtherapeutic dose and an immunomodulatory agent (e.g., fingolimod, interferon beta-1a, interferon beta-1b, glatiramer acetate, mitoxantrone, or natalizumab) is administered at a therapeutically effective dose for the treatment or prevention of a demyelinating disease (e.g., multiple sclerosis). In some embodiments, a neurotransmitter receptor modulating agent (e.g., a muscarinic receptor antagonist, a dopamine receptor antagonist, a histamine receptor antagonist, a beta adrenergic receptor modulator, or an opioid receptor modulator listed in Table 1, e.g., benztropine, clemastine, salmeterol, salbutamol, trifluoperazine, or a salt thereof) is administered at a subtherapeutic dose and an immunomodulatory agent (e.g., fingolimod, interferon beta-1a, interferon beta-1b, glatiramer acetate, mitoxantrone, or natalizumab) is administered at a subtherapeutic dose for the treatment or prevention of a demyelinating disease (e.g., multiple sclerosis).

IV. Pharmaceutical Compositions

In another aspect, the present invention provides pharmaceutical compositions for use in the treatment of a demyelinating disease (e.g., multiple sclerosis, idiopathic inflammatory demyelinating disease, transverse myelitis, Devic's disease, progressive multifocal leukoencephalopathy, optic neuritis, leukodystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or human T-cell lymphotropic virus (HTLV)-associated myelopathy). In some embodiments, the composition comprises a mixture of a neurotransmitter receptor modulating agent and an immunomodulatory agent. In some embodiments, the pharmaceutical composition comprises a neurotransmitter receptor modulating agent selected from a muscarinic receptor antagonist, a dopamine receptor antagonist, a histamine receptor antagonist, a beta adrenergic receptor modulator, and an opioid receptor modulator and an immunomodulatory agent selected from interferon beta-1a, interferon beta-1b, glatiramer acetate, mitoxantrone, fingolimod (FTY720), natalizumab, rituximab, daclizumab, and alemtuzumab. In some embodiments, the pharmaceutical composition comprises a neurotransmitter receptor modulating agent selected from benztropine, clemastine, salmeterol, salbutamol, trifluoperazine, and salts thereof and an immunomodulatory agent selected from interferon beta-1a, interferon beta-1b, glatiramer acetate, mitoxantrone, fingolimod (FTY720), natalizumab, rituximab, daclizumab, and alemtuzumab. In some embodiments, the pharmaceutical composition comprises benztropine or a salt thereof and an immunomodulatory agent selected from interferon beta-1a, interferon beta-1b, and fingolimod (FTY720).

In some embodiments, one or both of the neurotransmitter receptor modulating agent and the immunomodulatory agent are formulated as a therapeutically effective or optimal dose. In some embodiments, one or both of the neurotransmitter receptor modulating agent and the immunomodulatory agent are formulated as a subtherapeutic dose. In some embodiments, the neurotransmitter receptor modulating agent is formulated as a therapeutically effective or optimal dose and the immunomodulatory agent is formulated as a subtherapeutic dose. In some embodiments, the immunomodulatory agent is formulated as a therapeutically effective or optimal dose and the neurotransmitter receptor modulating agent is formulated as a subtherapeutic dose. Suitable dosage ranges for therapeutically effective and subtherapeutic doses of neurotransmitter receptor modulating agents and immunomodulatory agents are described above.

An agent for use in any of the therapeutic methods of the present invention (e.g., an agent that stimulates increased myelination as described herein, or an immunomodulatory agent as described herein) may be in any pharmaceutically acceptable form, including any pharmaceutically acceptable salts, prodrugs, racemic mixtures, conformational and/or optical isomers, crystalline polymorphs and isotopic variants of the neurotransmitter receptor modulating agents.

A combination of a neurotransmitter receptor modulating agent and an immunomodulatory agent can be incorporated into a variety of formulations for therapeutic or prophylactic administration. More particularly, a combination of a neurotransmitter receptor modulating agent and an immunomodulatory agent can be formulated into pharmaceutical compositions, e.g., a single composition, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of an agent of the present invention can be achieved in various ways, including oral, buccal, parenteral, intravenous, intradermal (e.g., subcutaneous, intramuscular), transdermal, etc., administration. Moreover, the agent can be administered in a local rather than systemic manner, for example, in a depot or sustained release formulation.

Formulations

Suitable formulations for use in the present invention are found in *Remington: The Science and Practice of Pharmacy*, 21st Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In some embodiments, an agent is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropyl cellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

For oral administration, an agent of the present invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The agents can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, an agent of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active agents in water-soluble form. Additionally, suspensions of the active agents can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the agents can take the form of tablets or lozenges formulated in conventional manner.

In addition to the formulations described previously, an agent of the present invention can also be formulated as a depot preparation. Such long acting formulations can be administered by implantation (for example subcutaneously or intramuscularly) or by intramuscular injection. Thus, for example, the agents can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the neurotransmitter receptor modulating compounds as described herein with an effective amount of other therapeutic agents as combination partners, particularly those used for treating demyelinating diseases, such as immunomodulary agents. An effective amount of the agent and/or combination partner will, of course, be dependent on the subject being treated, the severity of the affliction and the manner of administration. Determination of an effective amount is well within the capability of those skilled in the art, especially in light of the detailed disclosure provided herein. Generally, an efficacious or effective amount of an agent is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics,* 11th Ed., Brunton, Lazo and Parker, Eds., McGraw-Hill (2006), and in *Remington: The Science and Practice of Pharmacy,* 21st Ed., Gennaro, Ed., Lippencott Williams & Wilkins (2003), both of which are hereby incorporated herein by reference. In some embodiments, one or both of a neurotransmitter receptor modulating agent and an immunomodulary agent are formulated in a therapeutically effective dose. In some embodiments, one or both of a neurotransmitter receptor modulating agent and an immunomodulary agent are formulated in a subtherapeutic dose. In some embodiments, a neurotransmitter receptor modulating agent is formulated in a therapeutically effective dose and an immunomodulary agent is formulated in a subtherapeutic dose. In some embodiments, an immunomodulary agent is formulated in a therapeutically effective dose and a neurotransmitter receptor modulating agent is formulated in a subtherapeutic dose.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Administration

Administration of a neurotransmitter receptor modulating agent and/or an immunomodulatory agent can be achieved in various ways, including oral, buccal, parenteral, including intravenous, intradermal, subcutaneous, intramuscular, transdermal, transmucosal, intranasal, etc., administration. When a neurotransmitter receptor modulating agent and an immunomodulatory agent are co-administered, the neurotransmitter receptor modulating agent can be administered by the same or different route of administration as the immunomodulatory agent. In some embodiments, a compound of the present invention (e.g., a neurotransmitter receptor modulating agent and/or an immunomodulatory agent) is administered systemically.

The dosages and frequency of administration will depend upon various factors generally appreciated by those of skill in the art, including, e.g., the severity of a subject's disease. Generally, daily doses can range from about 0.001-100 mg/kg total body weight, from about 0.01-50 mg/kg, or from about 0.01 mg/kg-10 mg/kg. However, doses in the range of 10-500 mg/kg per day may be effective and well tolerated. The principal determining factor in defining the appropriate dose is the amount of a particular compound necessary to be therapeutically effective in a particular context. Repeated administrations may be required in order to achieve longer lasting immune tolerance. Single or multiple administrations of the compositions can be carried out with the dose levels and pattern being selected by the treating physician.

In some embodiments, a compound of the present invention (e.g., a neurotransmitter receptor modulating agent and/or an immunomodulatory agent) is administered to a subject in need thereof over an extended period of time. The methods can be carried out for at least 20 days, in some embodiments for at least 40, 60, 80 or 100 days, and in some embodiments for at least 150, 200, 250, 300, 350 days, 1 year or longer. In some embodiments, a compound of the present invention (e.g., a neurotransmitter receptor modulating agent and/or an immunomodulatory agent) is administered to a subject in need thereof at or after the onset of one or more symptoms of a demyelinating disease. In some embodiments, a compound of the present invention (e.g., a neurotransmitter receptor modulating agent and/or an immunomodulatory agent) is administered to a subject in need thereof prior to the onset of symptoms of a demyelinating disease (i.e., prophylactically).

Co-administration

In some embodiments, the methods of the present invention comprise co-administering a neurotransmitter receptor modulating agent and an immunomodulatory agent. Co-administered agents can be administered together or separately, simultaneously or at different times. When administered, the neurotransmitter receptor modulating agent and the immunomodulatory agent independently can be administered once, twice, three, four times daily or more or less often, as needed. In some embodiments, the agents are administered once daily. In some embodiments, the agents are administered at the same time or times, for instance as an admixture. One or more of the agents can be administered in a sustained-release formulation.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents (i.e., the neurotransmitter receptor modulating agent and the immunomodulatory agent are administered as a single formulation). In other embodiments, the active agents can be formulated separately (i.e., the neurotransmitter receptor modulating agent and the immunomodulatory agent are administered as separate formulations). In another embodiment, the active and/or adjunctive agents may be linked or conjugated to one another.

In some embodiments, one or both of a neurotransmitter receptor modulating agent and an immunomodulatory agent can be administered prophylactically to prevent undesirable recurrence of the symptoms of the demyelinating disease (e.g., to prevent or delay the recurrence of clinical attacks in MS), or therapeutically to achieve a desired reduction in symptoms of the demyelinating disease and maintain such reduction in symptoms of the demyelinating disease for a sustained period of time.

V. Kits

In another aspect, the present invention provides kits for use in the treatment of a demyelinating disease (e.g., multiple sclerosis, idiopathic inflammatory demyelinating disease, transverse myelitis, Devic's disease, progressive multifocal leukoencephalopathy, optic neuritis, leukodystrophy, Guillain-Barre syndrome, chronic inflammatory demyelinating polyneuropathy, autoimmune peripheral neuropathy, Charcot-Marie-Tooth disease, acute disseminated encephalomyelitis, adrenoleukodystrophy, adrenomyeloneuropathy, Leber's hereditary optic neuropathy, or human T-cell lymphotropic virus (HTLV)-associated myelopathy). In some embodiments, the kit comprises a neurotransmitter receptor modulating agent selected from a muscarinic receptor antagonist, a dopamine receptor antagonist, a histamine receptor antagonist, a beta adrenergic receptor modulator, and an opioid receptor modulator. In some embodiments, the kit comprises a neurotransmitter receptor modulating agent selected from a compound listed in Table 1. In some embodiments, the kit comprises a neurotransmitter receptor modulating agent selected from benztropine, clemastine, salmeterol, salbutamol, trifluoperazine, and salts thereof. In some embodiments, the kit comprises benztropine or a salt thereof.

In some embodiments, a kit of the present invention further comprises an immunomodulatory agent. In some embodiments, the kit comprises a neurotransmitter receptor modulating agent and an immunomodulatory agent for the treatment of MS (e.g., interferon-$\beta$, e.g., interferon beta-1a or interferon beta-1b, glatiramer acetate, mitoxantrone, fingolimod (FTY720), natalizumab, rituximab, daclizumab, or alemtuzumab). In some embodiments, the kit comprises a neurotransmitter receptor modulating agent selected from benztropine, clemastine, salmeterol, salbutamol, trifluoperazine, and salts thereof and an immunomodulatory agent selected from interferon beta-1a, interferon beta-1b, glatiramer acetate, mitoxantrone, fingolimod (FTY720), natalizumab, rituximab, daclizumab, and alemtuzumab. In some embodiments, the kit comprises benztropine or a salt thereof and an immunomodulatory agent selected from interferon beta-1a, interferon beta-1b, and fingolimod (FTY720).

In some embodiments, a kit comprises a neurotransmitter receptor modulating agent as described herein and an immunomodulatory agent in a single formulation. In some embodiments, a kit comprises a neurotransmitter receptor modulating agent as described herein and an immunomodulatory agent in separate formulations. Suitable formulations for the neurotransmitter receptor modulating agent and immunomodulatory agent are described herein. In some embodiments, a kit provides a neurotransmitter receptor modulating agent as described herein and one or more additional therapeutic agents (e.g., an immunomodulatory agent) independently in uniform dosage formulations throughout the course of treatment. In some embodiments, a kit provides a neurotransmitter receptor modulating agent as described herein and one or more additional therapeutic agents (e.g., an immunomodulatory agent) independently in graduated dosages over the course of treatment, either increasing or decreasing, but usually increasing to an efficacious dosage level, according to the requirements of an individual. In some embodiments, a kit comprises a neurotransmitter receptor modulating agent as described herein in a therapeutically effective dose and an immunomodulatory agent in a therapeutically effective dose. In some embodiments, a kit comprises a neurotransmitter receptor modulating agent as described herein in a therapeutically effective dose and an immunomodulatory agent in a sub-therapeutic dose.

EXAMPLES

The following examples are offered to illustrate, but not to limit the claimed invention.

Example 1: Small Molecule Screen to Identify Inducers of OPC Differentiation A large-scale small molecule screen was conducted to identify small molecules that promote the differentiation of oligodendrocyte precursor cells (OPCs) to a mature myelinating fate. High content imaging was used to detect in-well differentiation of rat optic nerve derived OPCs. Rat optic nerve derived OPCs were expanded en masse in OPC media containing 30 ng/mL PDGFαα. To screen for small molecule inducers of OPC differentiation, OPCs (cultured for fewer than 15 passages) were plated in poly-D-lysine coated 384 well culture plates in OPC Media containing 2 ng/mL PDGFαα and immediately treated with compounds at a final concentration of 6 µM (0.6% DMSO). Compound treated cells were incubated at 37° C., 5% $CO_2$ for 6 days. At the end of 6 days, cells were fixed in 4% paraformaldehyde and subjected to immunofluorescence analysis. Anti-Myelin Basic Protein monoclonal antibody (a.a. 129-138, clone 1 monoclonal antibody, Millipore) (1:1000 dilution) in blocking buffere solution (3% BSA, 0.3% Triton X-100 in PBS) was added to fixed and washed cells and incubated at 4° C. overnight. The primary antibody solution was removed and cells were washed with PBS prior to incubation with a blocking buffer solution containing goat anti-mouse IgG Alexa fluor488 (Invitrogen) secondary antibody (1:1000 dilution) and DAPI (2 ug/mL) for 1 hr at 25° C. The secondary antibody solution was washed with PBS and plates were imaged using an OPERA high content screening system (Perkin Elmer). A cell scoring based image analysis algorithm was used to identify and score MBP positive cells. Hits were identified as compounds that induced >400 cells/field and >5% MBP positive cells/field. The average values for DMSO negative controls were consistently <0.5% MBP positive. A total of 6058 compounds comprised of commercially available small molecule screening collections (LOPAC, Tocris, Enzo) were screened. A total of 104 primary hits were identified. These consisted of a number of known OPC differentiating inducing agents (e.g., retenoids, sterols, nucleoside analogues, Rho kinase inhibitors), as well as a number of previously unidentified OPC differentiation inducing agents (e.g., neurotransmitter modulating agents).

Identified primary hits were subsequently evaluated by determing EC50 values in multiple replicate experiments using the primary assay format for determing OPC differentiation. Cells were treated with compounds serially diluted in DMSO (10 dilutions of 1:3 across a range of 71 µM to 4 nM). Staining and imaging was performed as described for the primary screen. $EC_{50}$ values were determined using appropriate curve fitting equations in Graphpad Prism 5.0. FIG. 1A shows the EC50 for six identified hits (carbetapentane, clemastine, benztropine, trifluoperazine, salmeterol, and GBR12935), all of which are FDA-approved blood-brain barrier-penetrating drugs. FIG. 1 also shows the ability of these six identified hits to induce differentiation of OPCs (as measured by the percentage of myelin basic protein (MBP)-positive cells) at varying concentrations (FIG. 1B). For each of these agents, when the OPC sample was cultured with an agent at maximum potency, the percentage of resulting MBP-positive cells was at least 10% (FIG. 1C). For GBT12935, the percentage of resulting MBP-positive cells was over 15%. These results show that carbetapentane, clemastine, benztropine, trifluoperazine, salmeterol, and GBR12935 all promote OPC differentiation.

Example 2: Validation of Hits from Small Molecule Screen

Several classes of neurotransmitter receptor modulating agents that were identified by the primary screen were selected based on FDA approval status, known toxicity, and brain pharmacokinetics for evaluation in subsequent in vitro and in vivo validation assays. The ability of compounds to induce robust differentiation of OPCs to a fully mature myelinating oligodendrocyte cell fate was evaluated in vitro using quantitative RT-PCR, western blotting and immunofluorescence analysis techniques. The ability of compounds to induce remyelination in vivo (in the presence of inflammatory insult) was evaluated using a proteolipid protein (PLP) induced Experimental Autoimmune Encephalitis (EAE) mouse model of relapsing multiple sclerosis.

Quantitative RT-PCR ("qRT-PCR") and Western blot analysis were performed on OPC samples that had been cultured with DMSO (negative control), T3 (positive control), benztropine, carbetapentane, clemastine, trifluoperazine, GBR12935, or salmeterol to measure the levels of expression of MBP and MOG, markers for myelinating oligodendrocytes. As shown in FIG. 2A, OPC samples cultured with benztropine, carbetapentane, clemastine, GBR12935, or salmeterol all were positive for MBP and MOG expression. qRT-PCR showed two-fold induction of expression, or greater, of MBP and MOG for OPC samples cultured with benztropine, carbetapentane, clemastine, trifluoperazine, GBR12935, or salmeterol (FIG. 2B-C).

Figure 3:
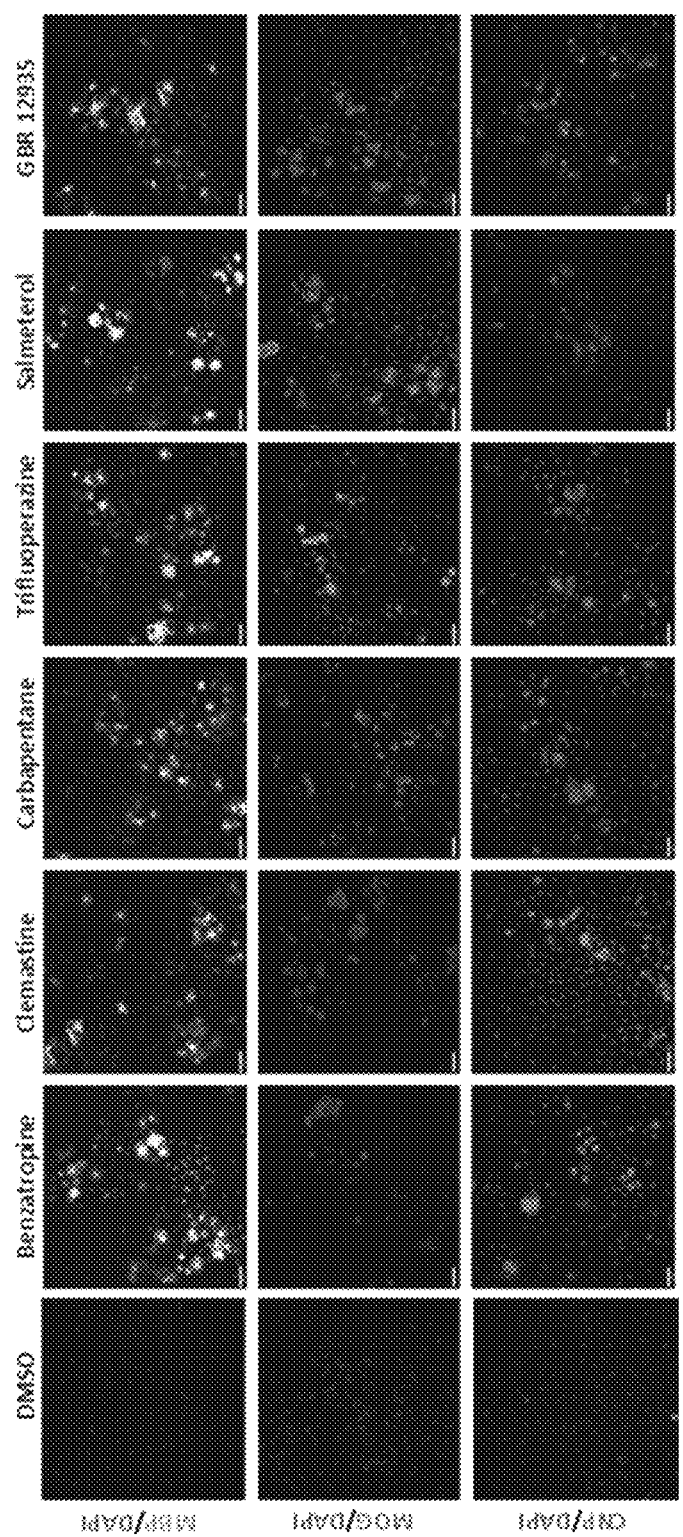
FIG. 3. Immunofluorescence analysis of compound treated OPCs using mature oligodendrocyte specific markers. Immunofluorescence staining using specific antibodies for MBP, MOG, and 2',3'-cyclic nucleotide 3' phosphodiesterase (CNP). Nuclei were identified using DAPI. Compound treatment of OPCs at $EC_{90}$ concentrations for 6 days induces the robust expression of mature oligodendrocyte markers.
Figure 4:
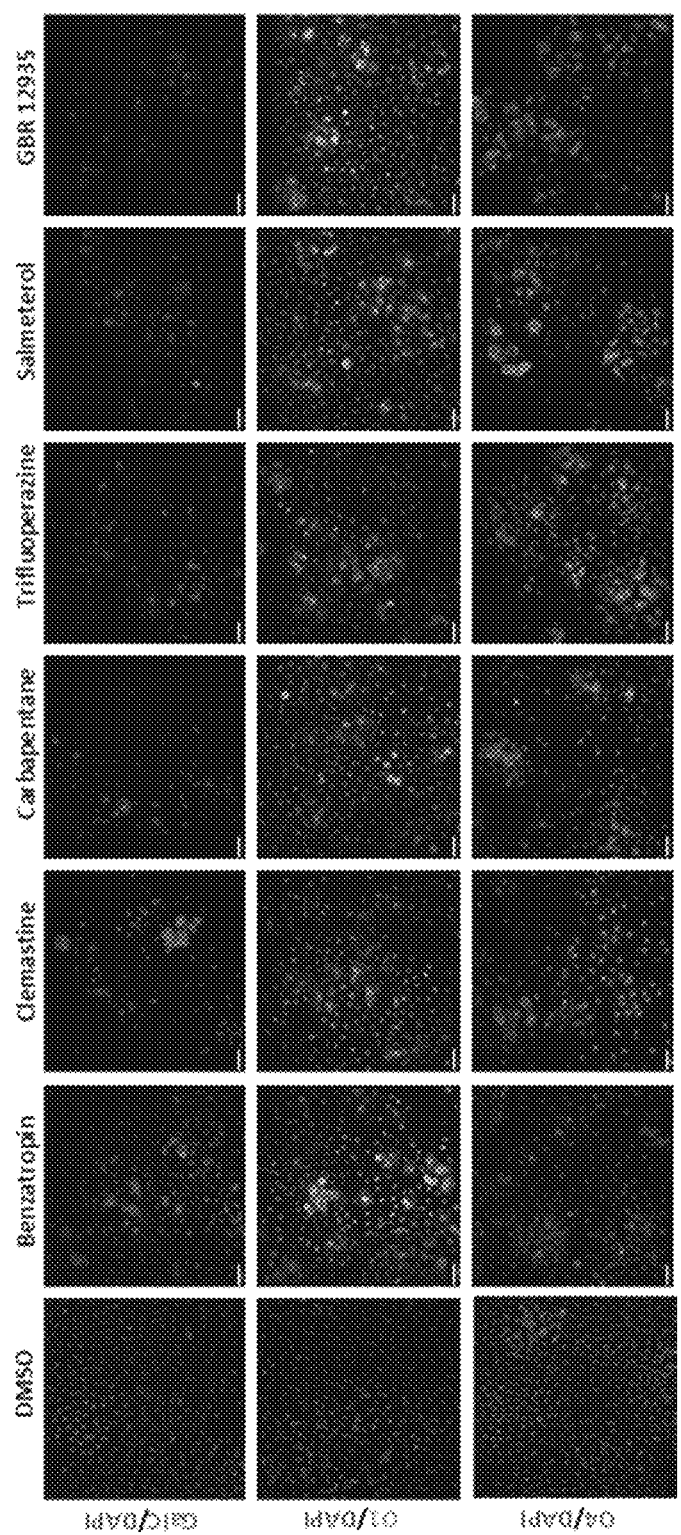
FIG. 4. Immunofluorescence analysis of compound treated OPCs using mature oligodendrocyte specific markers. Immunofluorescence staining using specific antibodies for galactocereberoside (GalC), oligodendrocyte marker O1 (O1) and oligodendrocyte marker O4 (O4). Nuclei were identified using DAPI. Compound treatment of OPCs at $EC_{90}$ concentrations for 6 days induces the robust expression of mature oligodendrocyte markers.

Immunofluorescence was also used to confirm that the hits were able to induce oligodendrocyte maturation. As shown in FIGS. 3 and 4, immunofluorescence analysis confirmed the presence of multiple markers of mature myelinating oligodendrocytes (MBP, MOG, CNP, GalC, O1, and O4) following treatment of in vitro cultures with benztropine, carbetapentane, clemastine, trifluoperazine, GBR12935, or salmeterol.

Figure 5A:
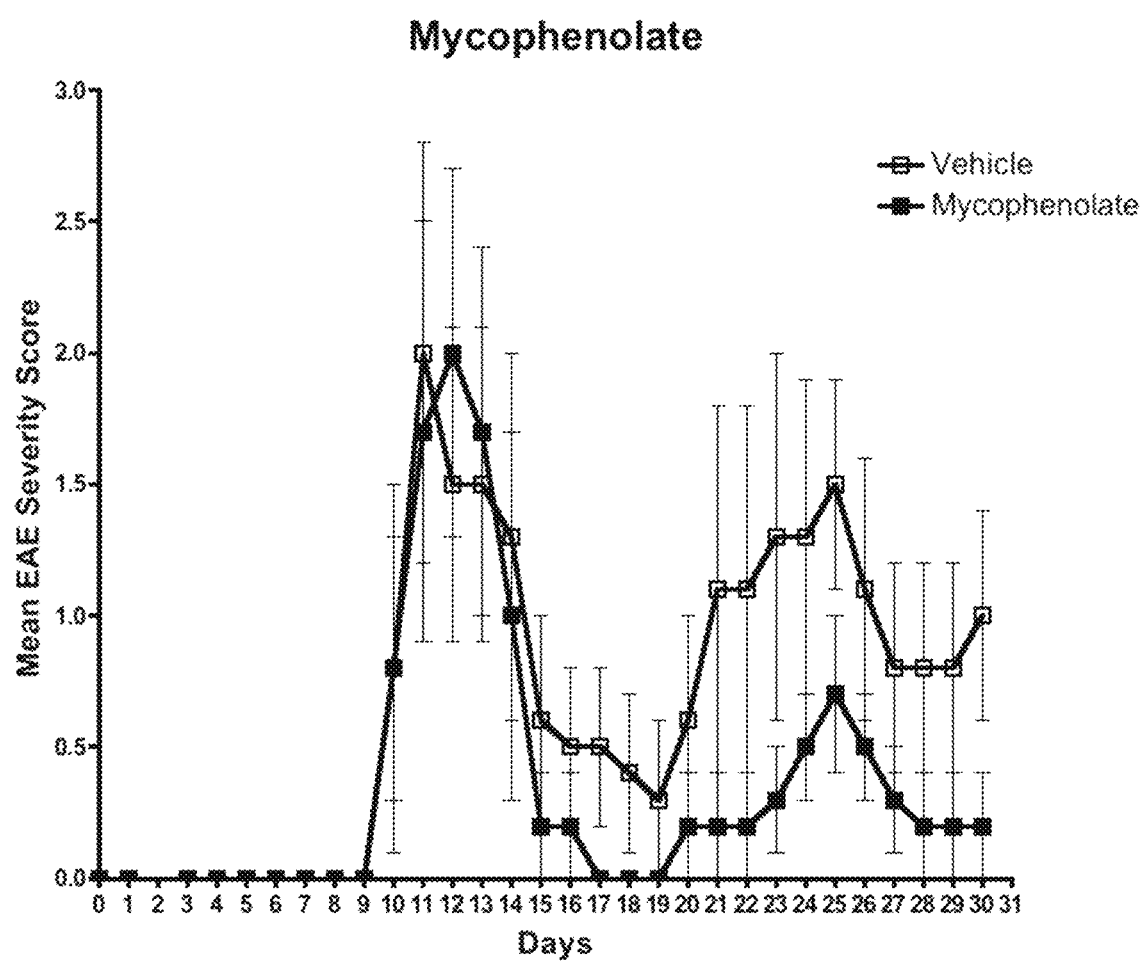

Two of the compounds, trifluoperazine and benztropine, were tested in vivo in proteolipid protein (PLP) induced Experimental Autoimmune Encephalitis (EAE) mice, a model of multiple sclerosis. 10 week old SJL mice were immunized with PLP emulsion and pertussis toxin to induce EAE. EAE symptoms developed in mice within 10 days after immunization. Animals that developed EAE showed neurological deficits ranging from impaired tail movements to paralysis in all 4 limbs with the most severe symptoms lasting for about 4 days, followed by a period of remission. Compounds were administered daily via intraperitoneal injection of 100 ul in sterile saline at 10 mg/kg alone or in combination with mycophenolate motefil in sterile saline at pH 5 at 20 mg/kg. Compound administration was initiated at disease onset (day 10) while mycophenolate motefil administration was initiated on Day 14. The mice were scored daily on a standard EAE scale of 0-5. MS-like symptoms were induced in 65-100% of the mice. Mycophenolate motefil, used at a sub-optimal dose showed a decrease in severity of the relapse (FIG. 5A). Trifluoperazine showed a modest decrease in recovery time following the acute phase (FIG. 5D-E). Each of trifluoperazine and benztropine alone significantly reduced the intensity of relapse measured as significantly lower EAE scores for compound treated animals compared to vehicle controls (FIG. 5B, D). In the presence of mycophenolate motefil no relapse was observed in animals treated with compounds (FIG. 5C, E). Thus, trifluoperazine and benztropine prevented relapse and improved motor and cognitive function as compared to the controls.

In another set of experiments, four compounds (benztropine, clemastine, trifluoperazine, and salbutamol) were tested in vivo in a EAE model. As shown in FIG. 34A, mice treated with benztropine (10 mg/kg) in a prophylactic mode showed a significantly decreased clinical severity in both acute and relapse phase of the disease as compared to vehicle treated mice. In a therapeutic mode, each of benztropine (FIG. 34C), trifluoperazine (FIG. 34D), clemastine (FIG. 34E), and salbutamol (FIG. 34E) showed a significantly decreased clinical severity in the relapse phase of the disease as compared to vehicle treated mice.

The pharmacological mechanisms of identified OPC differentiation-inducing agents was also investigated. It was determined that multiple pharmacological mechanisms exist for inducing OPC differentiation with identified agents. For example, as shown in FIG. 6A, muscarinic receptor agonism with carbachol inhibited the OPC differentiation induced by benztropine, carbetapentane, and clemastine, suggesting the mechanism at least some OPC differentiation-inducing agents is muscarinic receptor antagonism. Other muscarinic receptor antagonists, atropine and ipratropium, also induce OPC differentiation. However, carbachol did not inhibit OPC differentiation induced by salmeterol, GBR12935, or trifluoperazine, suggesting these agents induce OPC differentiation by one or more pharmacological mechanisms.

Example 3: A Stem Cell-Based Strategy for the Treatment of Multiple Sclerosis Studies aimed at evaluating the presence and relative densities of OPCs at sites of chronically demyelinated MS lesions indicate that it is not a failure of repopulation or migration of OPCs, but rather inhibition of OPC differentiation at sites of injury that contributes to disease progression (D. M. Chari, W. F. Blakemore, *Glia*, 37, 307 (2002); D. M. Chari et al., *J Neurosci Res*, 73, 787 (2003); G. Wolswijk, *J Neurosci*, 18, 601 (1998); A. Chang et al., *N Engl J Med*, 346, 165 (2002); T. Kuhlmann et al., *Brain*, 131, 1749 (2008)). As such, the identification of drug-like small molecules that selectively induce differentiation of OPCs at sites of demyelinated lesions would have a significant impact on the development of new, effective treatments for MS (D. Kremer et al., *Ann Neurol*, 69, 602 (2011)).

Primary rodent and human OPCs proliferate in vitro when cultured in serum-free media containing PDGF (C. Ffrench-Constant, M. C. Raff, *Nature*, 319, 499 (1986); M. C. Raff et al., *J Exp Biol*, 132, 35 (1987)). Upon withdrawal of PDGF, immature OPCs cease to proliferate, but also fail to efficiently differentiate to a mature myelin basic protein (MBP) positive fate (FIG. 11). Addition of triiodothryonine (T3), a known inducer of OPC differentiation (M. C. Nunes et al., *Nat Med*, 9, 439 (2003); N. Billon et al., *Dev Biol*, 235, 110 (2001); N. Billon et al., *EMBO J*, 21, 6452 (2002); Y. M. Tokumoto, D. G. Tang, M. C. Raff, *EMBO J* 20, 5261 (2001); Fernandes, 2004; L. Calza, M. Fernandez, L. Giardino, *J Mol Endocrinol*, 44, 13 (2010)), at the time of mitogen withdrawal results in the differentiation of OPCs to MBP positive oligodendrocytes following 6 days of culture (FIG. 11). Unfortunately, T3 has multiple physiological effects that make it unattractive as an OPC differentiation-based therapeutic.

To identify small drug-like molecules that induce OPC differentiation, we developed a high content imaging assay that is based on the induction MBP expression in primary rat optic nerve derived OPCs cultured for 6 days under basal differentiation conditions. The assay was adapted to 384 well format and used to screen collections of known biologically active compounds, as well as a collection of ~50K structurally diverse drug-like molecules. This led to the identification of multiple previously identified inducers of OPC differentiation including retinoids, corticosteroids, nucleoside analogs, Rho-kinase inhibitors and ErbB inhibitors (M. J. Latasa et al., *Glia*, 58, 1451 (2010); C. E. Buckley et al., *Neuropharmacology*, 59, 149 (2010); L. Joubert et al., *J Neurosci Res*, 88, 2546 (2010); A. S. Baer et al., *Brain* 132, 465 (2009); A. S. Paintlia et al., *Mol Pharmacol*, 73, 1381 (2008); C. Ibanez et al., *Prog Neurobiol*, 71, 49 (2003); L. Giardino, C. Bettelli, L. Calza, *Neurosci Lett*, 295, 17 (2000)), which have limited therapeutic potential due to off-target activities, toxicity, or a demonstrated lack of in vivo efficacy. Surprisingly, among the most effective inducers of OPC differentiation was benztropine ($EC_{50}$~350 nM), for which OPC differentiation activity has not previously been reported (FIGS. 7A and 12). We chose to further investigate the activity of this compound, as it is an orally available, well-tolerated, FDA approved drug that readily crosses the blood brain barrier, and therefore has the potential to move rapidly to proof of concept studies as a new treatment for MS.

Figure 13:
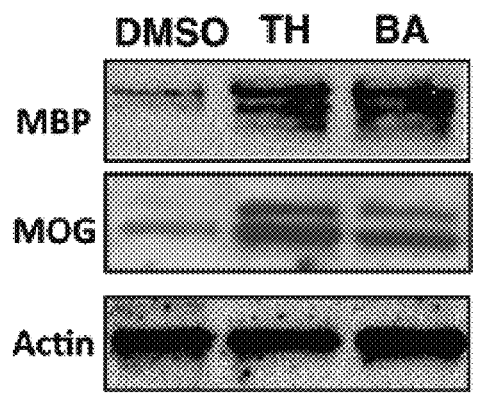
FIG. 13. Benztropine induces differentiation of OPCs to mature oligodendrocytes. OPCs were plated in differentiation medium (Neurobasal medium, B27 supplement without Vitamin A, non-essential amino acids, L-Glutamine, 2 ng/ml PDGF) and treated with DMSO (<0.01%), benztropine [1.5 uM] or thyroid hormone [1 uM]. After 6 days in culture, cells were analyzed for MBP and MOG expression by Western blot.
Figure 14:
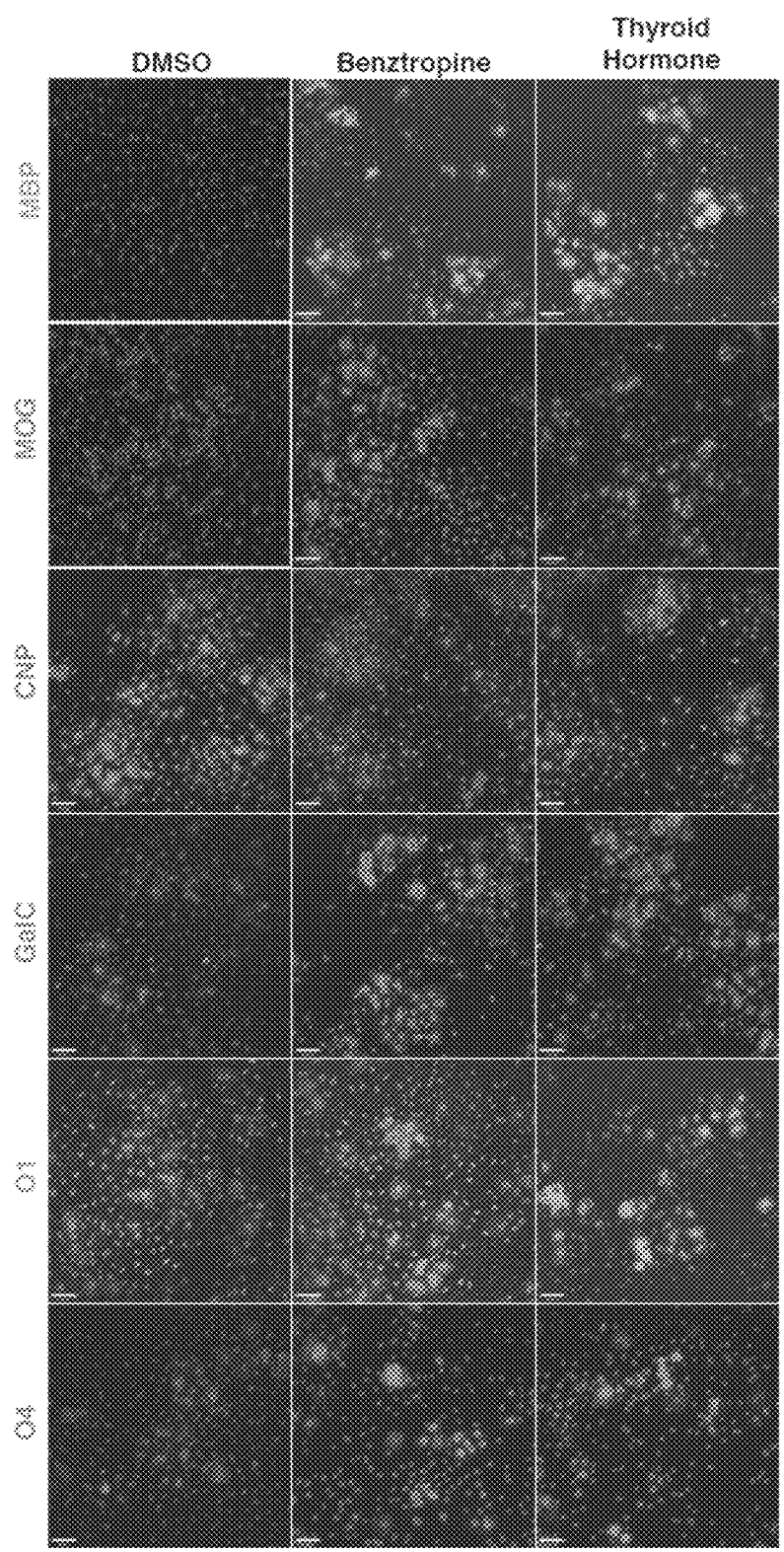
FIG. 14. Compound treatment induces the differentiation of OPCs to mature oligodendrocytes. OPCs were plated in differentiation medium (Neurobasal medium, B27 supplement without Vitamin A, non-essential amino acids, L-Glutamine, 2 ng/ml PDGF) and treated with DMSO (<0.01%), benztropine [1.5 uM] or thyroid hormone [1 uM] for 6 days. Cells were fixed and immunostained for MBP, MOG, CNP, GalC, O1, or O4. Representative images of DMSO, benztropine and thyroid hormone treated cells show expression of mature oligodendrocyte markers in benztropine and thyroid hormone treated cells, but not in DMSO treated cells.
Figure 15:
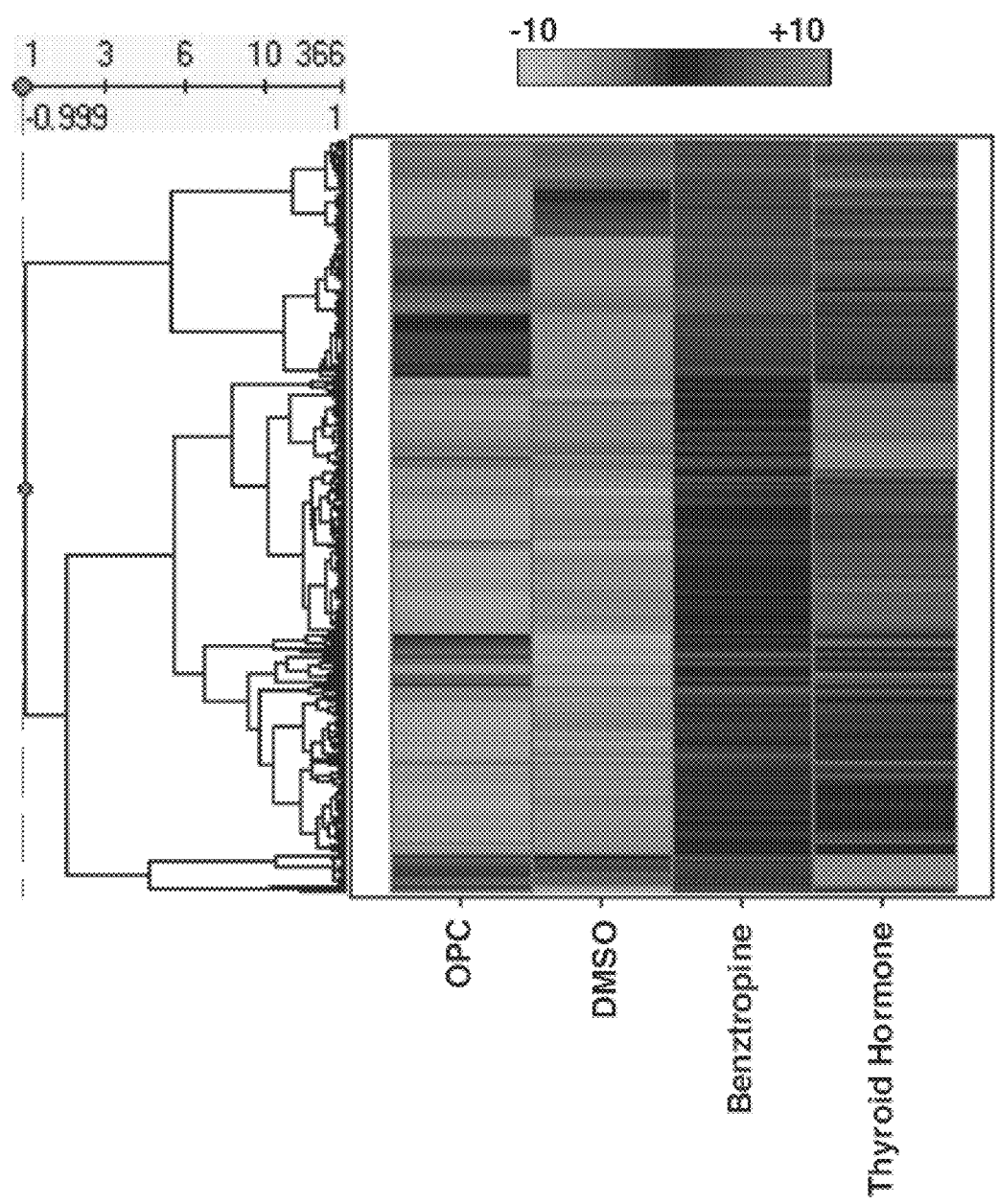
FIG. 15. Gene expression profile of OPCs differentiated to oligodendrocytes by benztropine treatment. OPCs were plated in differentiation medium and treated with DMSO (<0.1%), benztropine [2.3 uM] or thyroid hormone [1 uM] for 6 days. OPCs from the same passage were also pelleted and frozen. Total RNA was isolated from the cells and gene expression analysis was performed using rat genome arrays from Affymetrix. Global clustering analysis of mRNA expression probe sets that displayed a >2-fold change in expression across samples shows clustering of benztropine treated samples with thyroid hormone treated samples while gene expression profiles of DMSO treated cells cluster with OPCs. Data are represented as fold change over DMSO treated controls. Increased expression of mature oligodendrocyte genes was seen in compound treated cells as compared to DMSO treated cells.

Benztropine-induced in vitro differentiation of rodent OPCs was confirmed by evaluating the transcription and translation levels of the oligodendrocyte specific markers MBP and myelin oligodendroglial glycoprotein (MOG) by RT-PCR and Western blot analysis, respectively (FIGS. 7B and 13). Additionally, in vitro OPC differentiation activity was assessed by immunofluorescent analysis using multiple markers specifically expressed in mature oligodendrocytes (including MBP, MOG, 2',3'-cyclic-nucleotide 3'-phosphodiesterase (CNP), galactocerebrosidase (GalC), oligodendrocyte marker O1 (O1) and oligodendrocyte marker O4 (O4)) following six days of compound treatment (FIG. 14). Furthermore, global gene expression profiles of OPCs treated for 6 days with benztropine were found to cluster with those obtained from T3 treated positive control cells (FIG. 15). Downregulation of OPC specific genes required for proliferation (e.g., Idr2, Egr1, Sox11; V. A. Swiss et al., *PLoS One*, 6, e18088 (2011)), and upregulation of mature myelinatingoligodendrocyte specific genes (e.g., lipid metabolism, myelin related proteins (V. A. Swiss et al., PLoS One, 6, e18088 (2011)) was observed following treatment of OPCs with benztropine (FIG. 16). In order to determine the stage of OPC differentiation at which benztropine is active (Gard, *Neuron*, 3, 615 (1990); A. L. Gard, S. E. Pfeiffer, *Dev Biol*, 159, 618 (1993); D. Avossa, S. E. Pfeiffer, *J Neurosci Res*, 34, 113 (1993); R. Aharoni et al., *Proc Natl Acad Sci U.S.A.*, 102, 19045 (2005)), we treated OPCs for differing durations starting at multiple time points (FIG. 17). Maximal induction of MBP expression was observed when compound was added within 48 hours of PDGF withdrawal and left to incubate for 5 days (FIG. 17), indicating that this drug likely acts on immature A2B5 positive OPCs and not on an intermediate "pre-oligodendrocyte" stage of differentiation.

Figure 18:
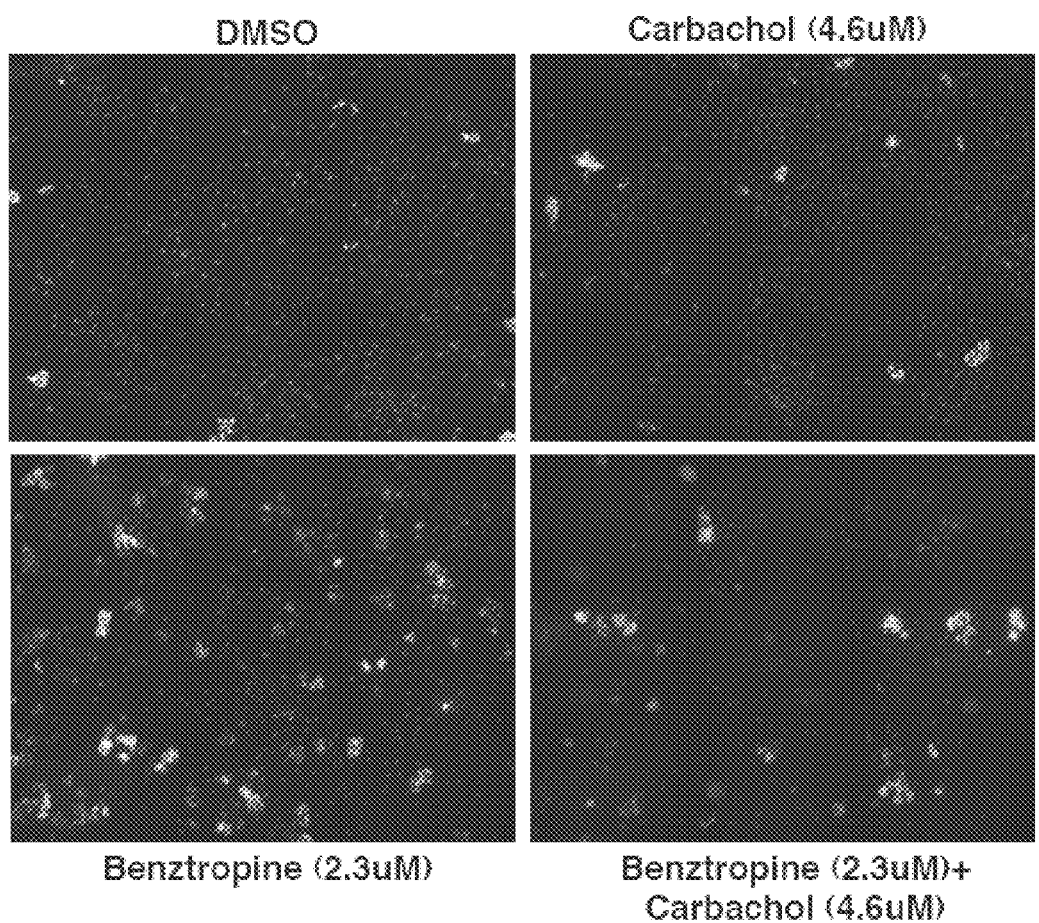
FIG. 18. Carbachol antagonizes benztropine induced OPC differentiation. OPCs were plated in basal differentiation media and co-treated with benztropine [2.3 uM] and carbachol [0 uM, 0.6 uM or 4.7 uM] for 6 days and stained for MBP (green).
Figure 21:
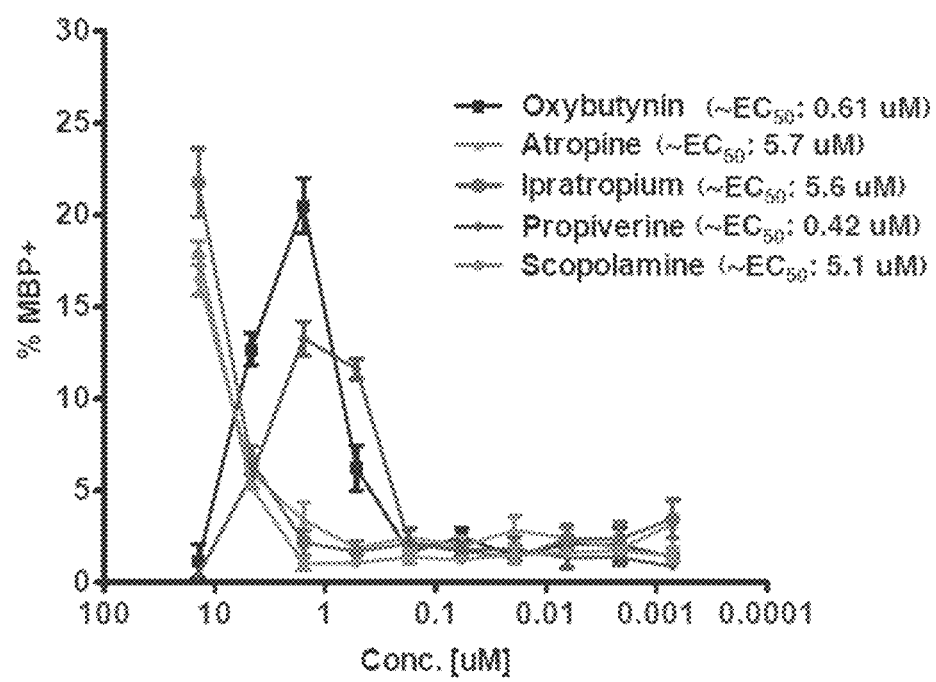
FIG. 21. Muscarinic antagonists induce differentiation of OPCs to oligodendrocytes. OPCs were plated in differentiation medium (2 ng/ml PDGF) and treated with various concentrations of compounds for 6 days. Cells were fixed and immunostained for MBP. Selective muscarinic antagonists oxybutynin, atropine, ipratropium, propiverine, and scopolamine induced differentiation of OPCs in a dose dependent manner. $EC_{50}$ values for compound induced differentiation are indicated.
Figure 22:
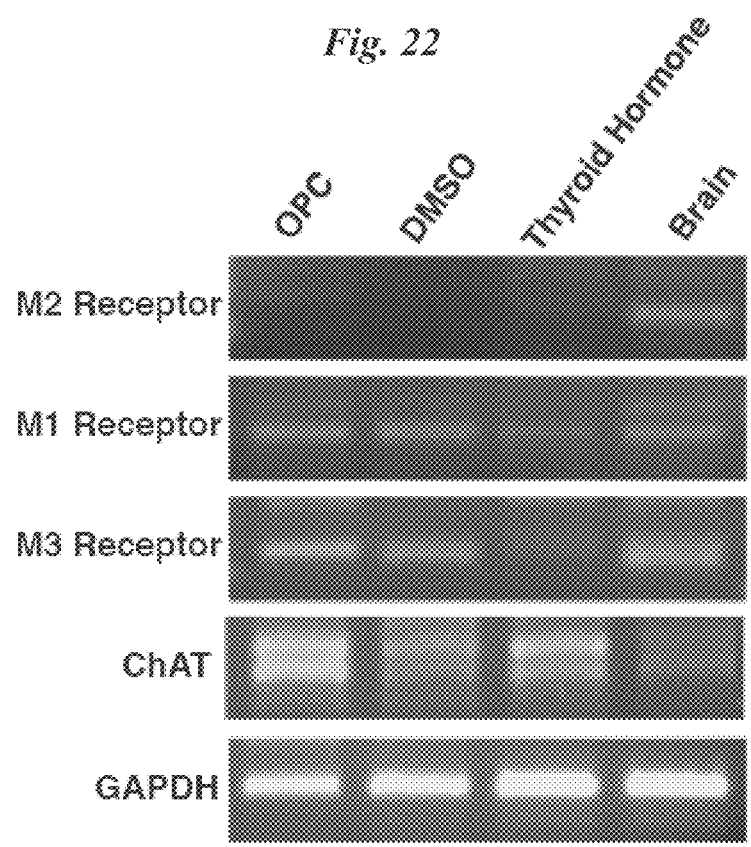
FIG. 22. OPCs express muscarinic receptors and choline acetyl transferase. Total RNA was isolated from OPCs treated with DMSO (<0.1%) or thyroid hormone [1 uM] for 6 days, or from whole rat brain. RNA was reverse transcribed to cDNA and gene expression of muscarinic receptors $M_1$, $M_2$, or $M_3$ was detected by PCR using gene specific primers.
Figure 23A:
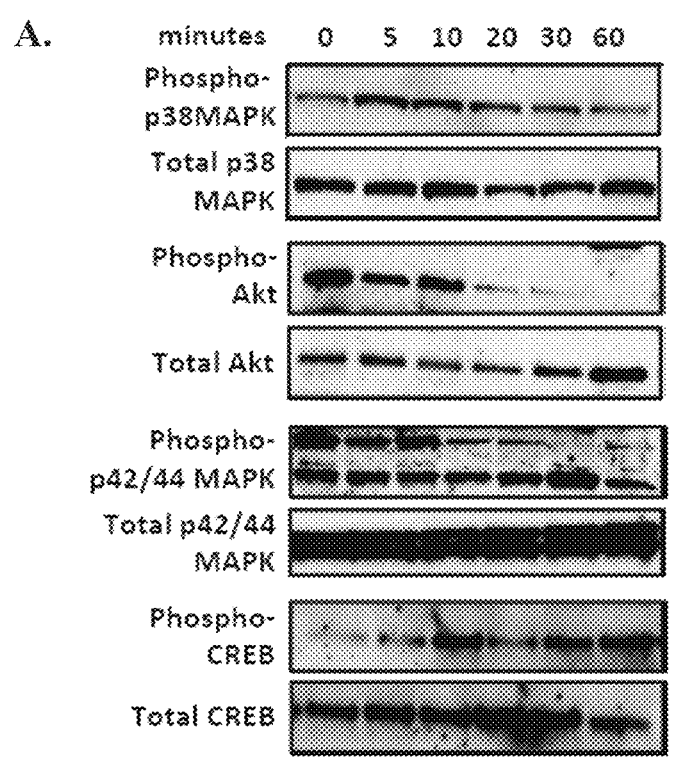
FIG. 23A-C. Antagonism of $M_1/M_3$ muscarinic signaling pathway by benztropine primes OPCs for differentiation. (A) OPCs were treated with benztropine [10 uM] for the indicated times and pelleted for Western blot analysis of total protein. Benztropine inhibits signaling proteins downstream of $M_1/M_3$ muscarinic receptors by down-regulating phosphorylation of Akt, p42MAP Kinase, and increasing phosphorylation of p38MAP Kinase and CREB. (B) OPCs were plated in basal differentiation conditions and treated with benztropine [1.5 uM], thyroid hormone [1 uM] or DMSO (<0.1%). OPCs from the same passage were also pelleted and frozen. Total RNA was isolated from the cells, reverse transcribed to first strand cDNA and used as a template for qRT-PCR. Gene specific FAM labeled probes were used to detect expression levels of various genes, with probes for beta-actin and GAPDH as internal controls. Gene expression shows a downregulation in cell cycle genes such as Cyclin D1, Cyclin D2, c-Fos, c-Jun indicating an exit from cell cycle. (C) Signaling pathway downstream of the $M_1/M_3$ muscarinic receptors.
Figure 23B:
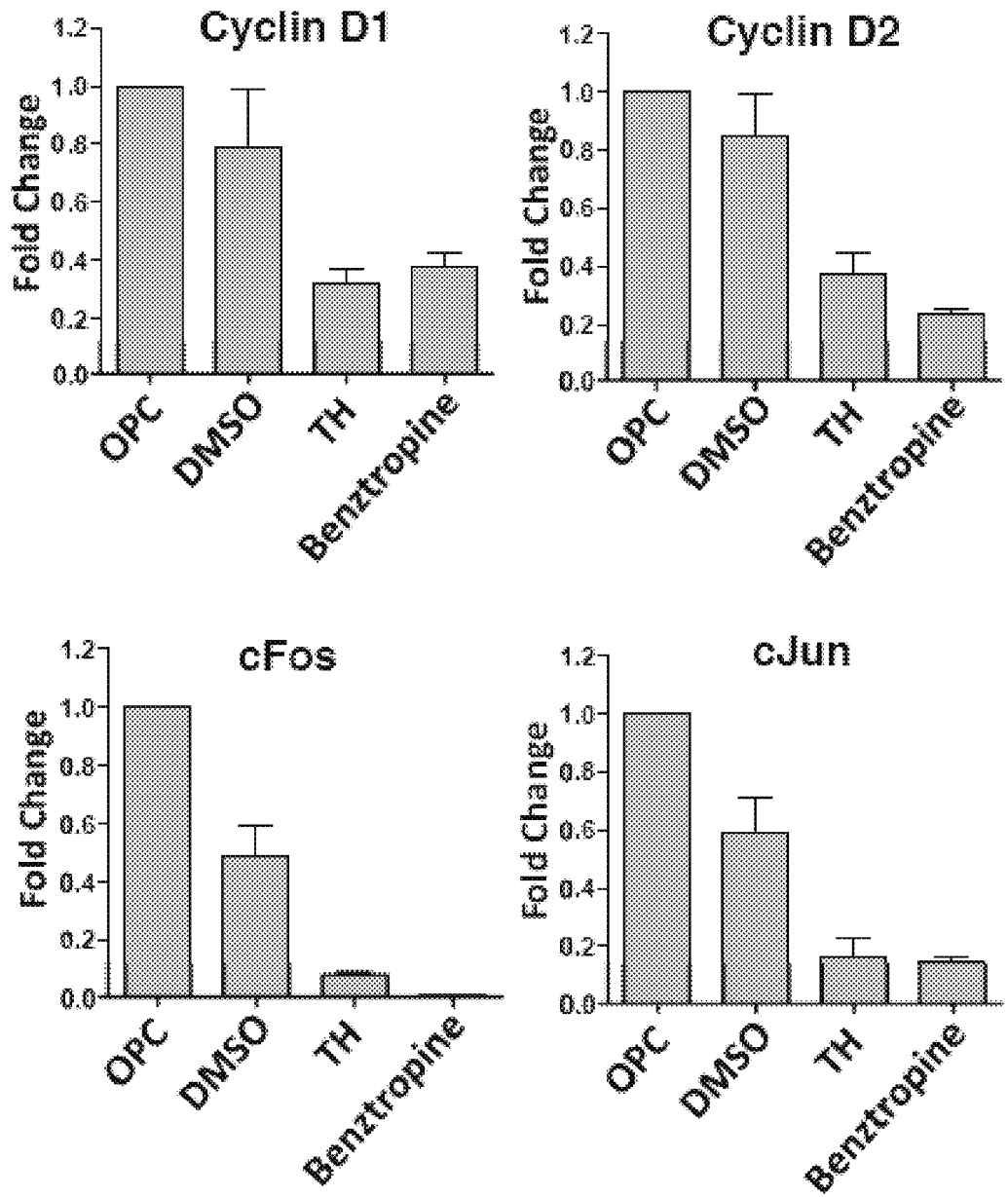
Figure 23C:
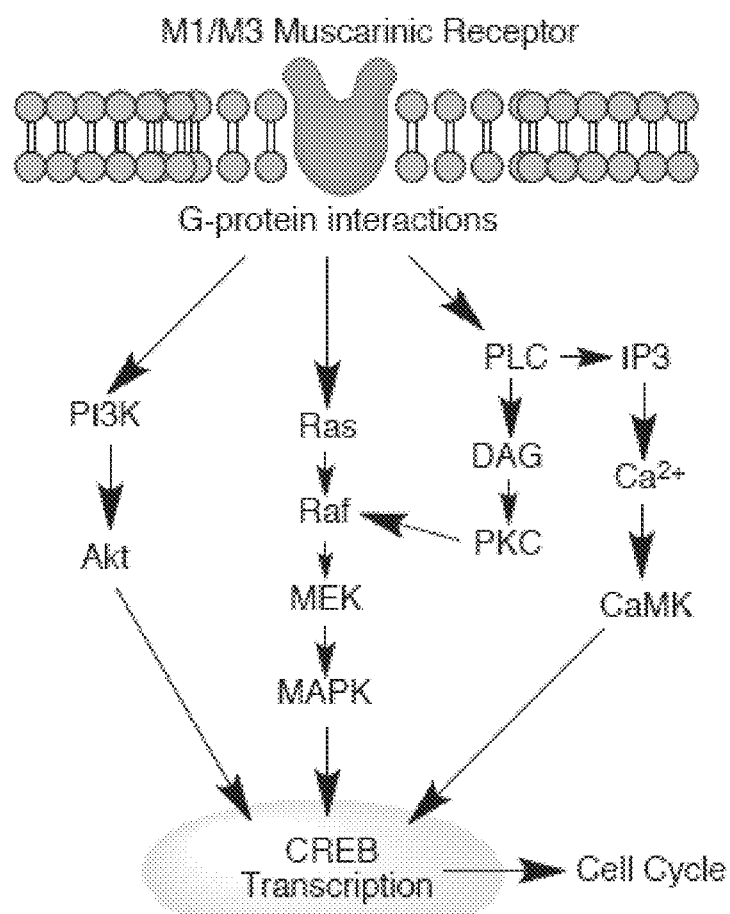

Benztropine is used clinically for the management of Parkinson's disease and its pharmacological activity is thought to result from anticholinergic activity that decreases the imbalance between dopamine and acetylcholine (A. J. Eshleman et al., *Mol Pharmacol*, 45, 312 (1994); R. Katsenschlager et al., *Cochrane Database Syst Rev*, CD003735 (2003); J. T. Coyle and S. H. Snyder, *Science*, 166, 899 (1969)). In addition to its anticholinergic activity, Benztropine is a centrally acting anti-histamine and dopamine re-uptake inhibitor (G. E. Agoston et al., *J Med Chem*, 40, 4329 (1997); J. L. Katz et al., *J Pharmacol Exp Therap*, 309, 605 (2004); D. Simoni et al., *J Med Chem*, 48, 3337 (2005)). In order to determine the mechanism of action of benztropine, we evaluated the ability of selective agonists of muscarinic acetylcholine receptors (mAChRs) (e.g., carbachol) or histaminergic receptors (e.g., histamine and histamine trifloromethyl-toluidine (HTMT)) to block benztropine activity. Potent inhibition of benztropine induced OPC differentiation was observed in the presence of carbachol (FIGS. 7C and 18), whereas histamine or HTMT showed no observable effect (FIG. 19). In addition, neither the dopamine receptor antagonist haloperidol, nor the dopamine receptor agonist quinpirole affected the induction of OPC differentiation by benztropine (FIG. 20). Quinpirole did not induce significant differentiation when used alone either (data not shown). We therefore next evaluated a panel of mAChR antagonists (atropine, oxybutynin, scopolamine, ipratropium, and propiverine) and found that all induced OPC differentiation in a dose dependent manner (FIG. 21). OPCs express mAChRs, predominantly subtypes $M_1$, $M_3$, and $M_5$ (F. Ragheb et al., *J Neurochem*, 77, 1396 (2001)). We confirmed expression of these receptors, as well as the acetylcholine synthesizing enzyme, choline acetyl transferase, in OPCs by RT-PCR (FIG. 22). Carbachol induced activation of mAChRs triggers protein kinase-C dependent activation of the MAPK/ERK pathway leading to modulation of c-Fos expression (F. Ragheb et al., *J Neurochem*, 77, 1396 (2001)). Western blot analysis of benztropine treated OPCs was consistent with general inhibition of this pathway (i.e., decreased phospho-p42/44 MAPK and phospho-Akt and stimulated phosphorylation of p38 MAPK and CREB) (FIG. 23A). Additionally, transcript levels of cyclin D1, cyclin D2, c-Fos, and c-Jun were significantly decreased in benztropine treated OPCs, consistent with a mechanism involving general inhibition of MAPK/ERK dependent cell cycle progression (FIG. 23B). Activation of $M_1$ and $M_3$ mAChRs is coupled to downstream signal transduction events through phospholipase C, which results in increased intracellular calcium concentrations (F. Ragheb et al., *J Neurochem*, 77, 1396 (2001)) (FIG. 23C). $M_2$ and $M_4$ mAChR activation inhibits adenylatecyclase, leading to decreased intracellular cAMP levels (C. C. Felder, *FASEB J*, 9, 619 (1995); M. Lopez-Ilasaca et al., *Science*, 275, 394 (1997)). In OPCs, benztropine inhibits carbachol induced calcium influx, but has no effect on cAMP levels (FIG. 24). Together, these results suggest that benztropine induces OPC differentiation by a mechanism involving direct antagonism of $M_1$/$M_3$ muscarinic receptors. Acetylcholine is a known regulator of OPC proliferation and, as such, muscarinic receptor subtypes represent a reasonable class of therapeutic targets for the modulation of OPC proliferation and differentiation (F. De Angelis et al., *Dev Neurobiol*, (2011)).

Figure 25:
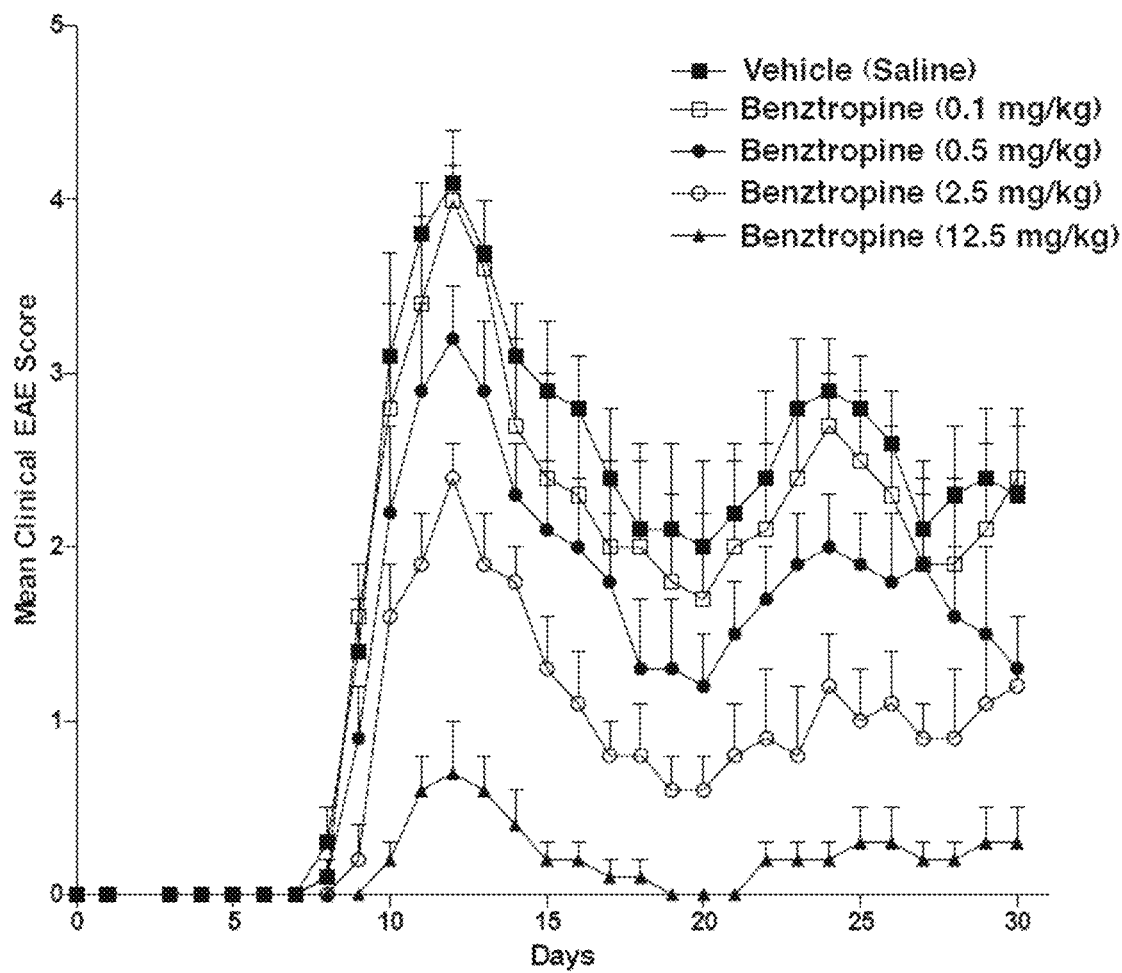
FIG. 25. Dose dependent activity of prophylactic benztropine in the EAE model. EAE was induced in mice using PLP and pertussis toxin. Benztropine dissolved in saline at various doses was injected via I.P. injection daily using the prophylactic mode followed by scoring clinical symptoms. Prophylactic dosing is defined as administration of compound commenced on the day of PLP injection. Error bars indicate standard deviation of the mean within each group of 8 mice.

We next examined the activity of benztropine in the myelin proteolipid protein (PLP)-induced experimental autoimmune encephalomyelitis (EAE) rodent model of relapsing-remitting MS (D. A. Sipkins, *J Neuroimmunol*, 104, 1 (2000); T. Owens, S. Sriram, *Neurol Clin*, 13, 51 (1995)). This model is most commonly used to evaluate the potential efficacy of immunomodulatory agents, but can also be used to determine the effectiveness of promyelinating agents that function by enhancing OPC differentiation (M. Fernandez et al., *Proc Natl Acad Sci U.S.A*, 101, 16363 (2004); X. Lee et al., *J Neurosci*, 27, 220 (2007); reviewed in R. J. Franklin, C. Ffrench-Constant, *Nat Rev Neurosci*, 9, 839 (2008)). Benztropine (10 mg/kg) was dosed prophylactically using a daily intraperitoneal (IP) injection regimen initiated at the onset of immunization of 8 week old SJL mice with PLP. Benztropine dramatically decreased the severity of the acute phase of disease and virtually eliminated the observation of a relapse phase as compared to vehicle treated controls (FIGS. 8A and 25). We next evaluated efficacy when the drug is dosed therapeutically, by starting daily injections at the first sign of disease onset. Treatment with benztropine in this mode again led to functional recovery, with significant decreases in clinical severity in remission phases observed and the occurrence of relapse again virtually eliminated (FIG. 8A). In fact, treatment with benztropine in this mode resulted in decreases in observed clinical severity that exceeded those observed for the immunomodulating MS drugs FTY720 or interferon-β (dosed at near maximally tolerated doses) (FIG. 8A).

Figure 8C:
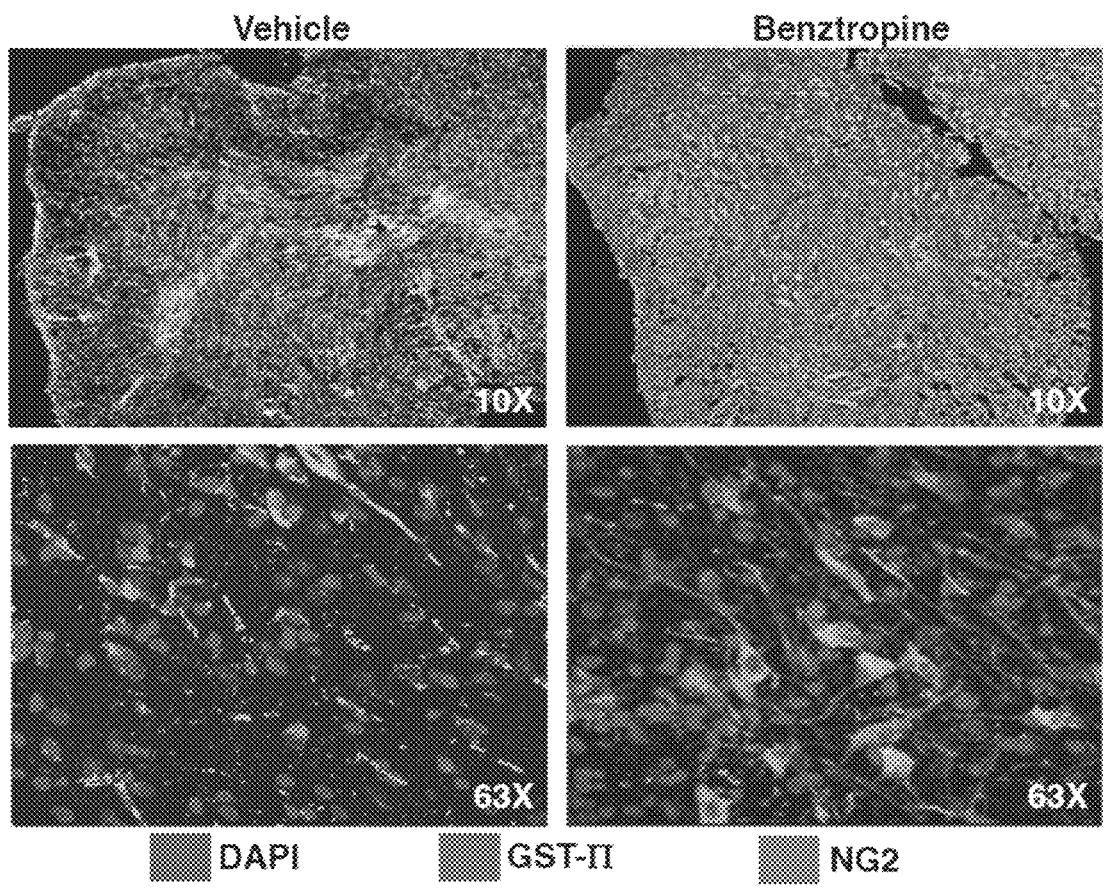
Figure 26:
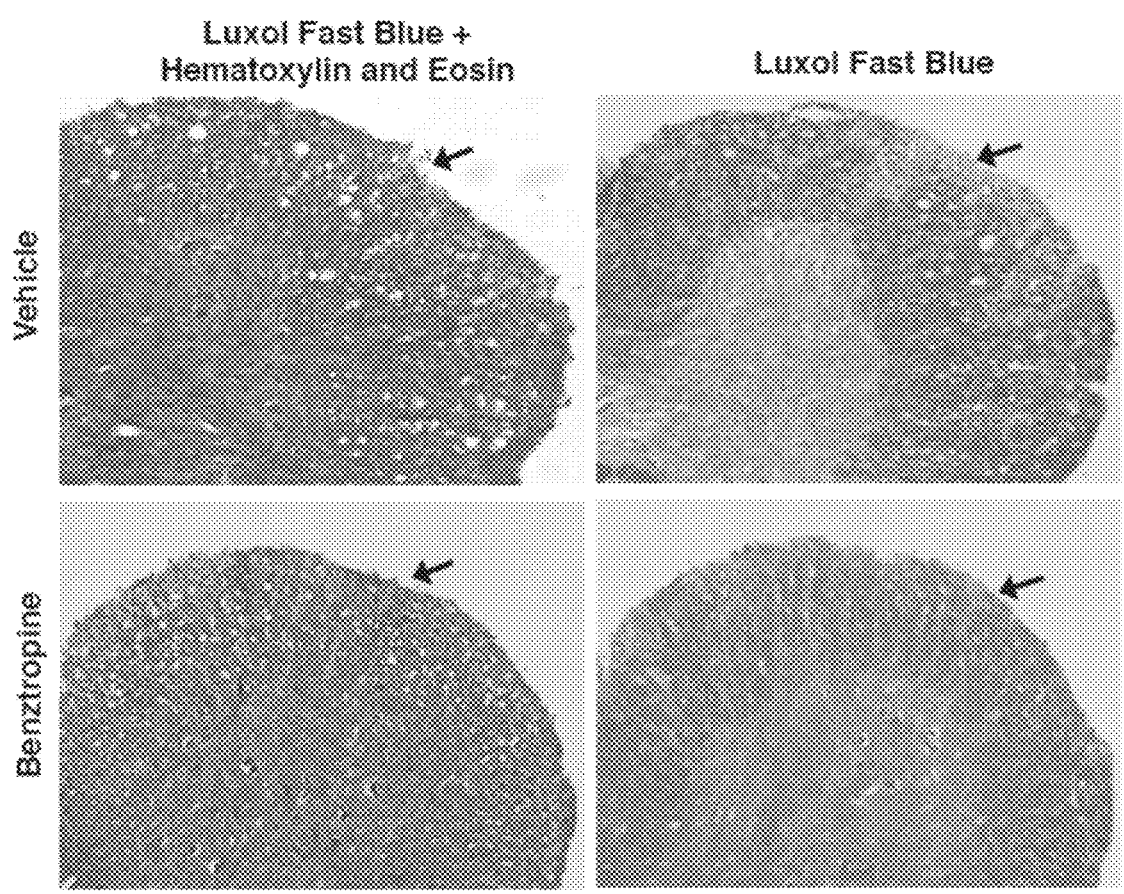
FIG. 26. Benztropine treatment induces remyelination in vivo in the PLP induced EAE models for MS. Benztropine does not block lymphocyte infiltration in EAE mice, but leads to significantly increased LFB staining, indicating the presence of myelin in areas infiltrated by lymphocytes as compared to vehicle treated mice. EAE was induced in mice by injecting PLP and pertussis toxin and the mice were treated with benztropine (10 mg/kg) or vehicle controls at the first appearance of EAE symptoms. Spinal cords were isolated from mice representative of the average group scores during the relapse phase of EAE, sectioned and stained with Luxol Fast Blue and H&E (left panel) and Luxol Fast Blue only (right panel). Arrows point to regions of lymphocyte infiltration.

In parallel experiments, during relapse phases (day 23-25), we isolated spinal cords from benztropine or vehicle treated mice and stained sections from multiple regions of each spinal cord with luxol fast blue (LFB) (to visualize myelin) or H&E (to visualize infiltrating immune cells). Sections from both vehicle and benztropine treated mice showed significant infiltration by H&E reactive immune cells (FIG. 26). In vehicle treated mice, areas of infiltration corresponded to areas with significant demyelination (FIG. 26). In contrast, in benztropine treated mice, a large number of immune cell infiltrated areas stained positive for LFB, consistent with a stem cell versus immunomodulatory mechanism (FIG. 26). We further evaluated drug-enhanced remyelination using confocal microscopy, by examining regions of T-cell infiltration in spinal cord sections stained with markers of mature oligodendrocytes (GST-π) and immature OPCs (NG2) (FIG. 8B). Quantitative image analysis of multiple random fields per group indicates that benztropine treatment causes a significant increase in the number of GST-π positive mature oligodendrocytes from ~500 to ~1100 per field (FIG. 8C), whereas the number of NG2 positive cells did not differ significantly with treatment (FIG. 8C). The observed increase in mature oligodendrocyte numbers at sites of T-cell infiltration is consistent with a mechanism of benztropine-induced clinical recovery that involves the stimulation of OPC differentiation, leading to enhanced remyelination, in the context of an inflammatory environment. Notably, general toxicity was not observed in drug treated mice, nor was it observed in this histological analysis (i.e., drug induced demyelination was not observed) following 4 weeks of daily injections at 10 mg/kg.

The primary immunological processes involved in MS and EAE are T-cell mediated and the primary treatment paradigms are based on immunomodulatory drugs (T. Kopadze et al., *Arch Neurol*, 63, 1572 (2006); J. M. Greer et al., *J Immunol*, 180, 6402 (2007), M. P. Pender and J. M. Greer, *curr Allergy Asthma Rep*, 7, 285 (2007)). In order to determine whether the efficacy of benztropine in the EAE model results at least in part from a T-cell inhibitory activity, we evaluated the effects of benztropine on T-cell activation and proliferation. Benztropine had no effect on T-cell activation or proliferation in vitro, as determined by evaluating $CD4^+/CD69^+$ and $CD4^+/CD25^+$ populations and using a CFSE assay, respectively (FIG. 27). We evaluated the effect of benztropine on the immune system in vivo in SJL mice in which EAE had or had not been induced with PLP. In either diseased or healthy animals, benztropine had no effect on the number of circulating splenocytes, $CD4^+$ cells, $CD8^+$ cells, $CD4^+/CD44Hi$ cells and $CD8^+/CD44Hi$ cells (FIGS. 28 and 29). A minor but significant decrease in B-cell numbers was observed following treatment with benztropine (FIGS. 28 and 29). Treatment with benztropine had no effect on cytokine production, as determined by evaluating CD4$^+$/IL2$^+$, CD4$^+$/IFN-$\gamma^+$, CD4$^+$/IL-10$^+$ and CD4$^+$/TNF-$\alpha^+$ T-cell populations isolated from drug or vehicle treated normal or diseased mice (FIGS. 28 and 29). We also tested the effects of benztropine on T-cell dependent responses induced by TNP-LPS and TNP-Ficoll and on T-cell independent responses produced by TNP-KLH. Benztropine had no effect on IgG and IgM production in response to any of these antigens (FIG. 30).

Figure 32:
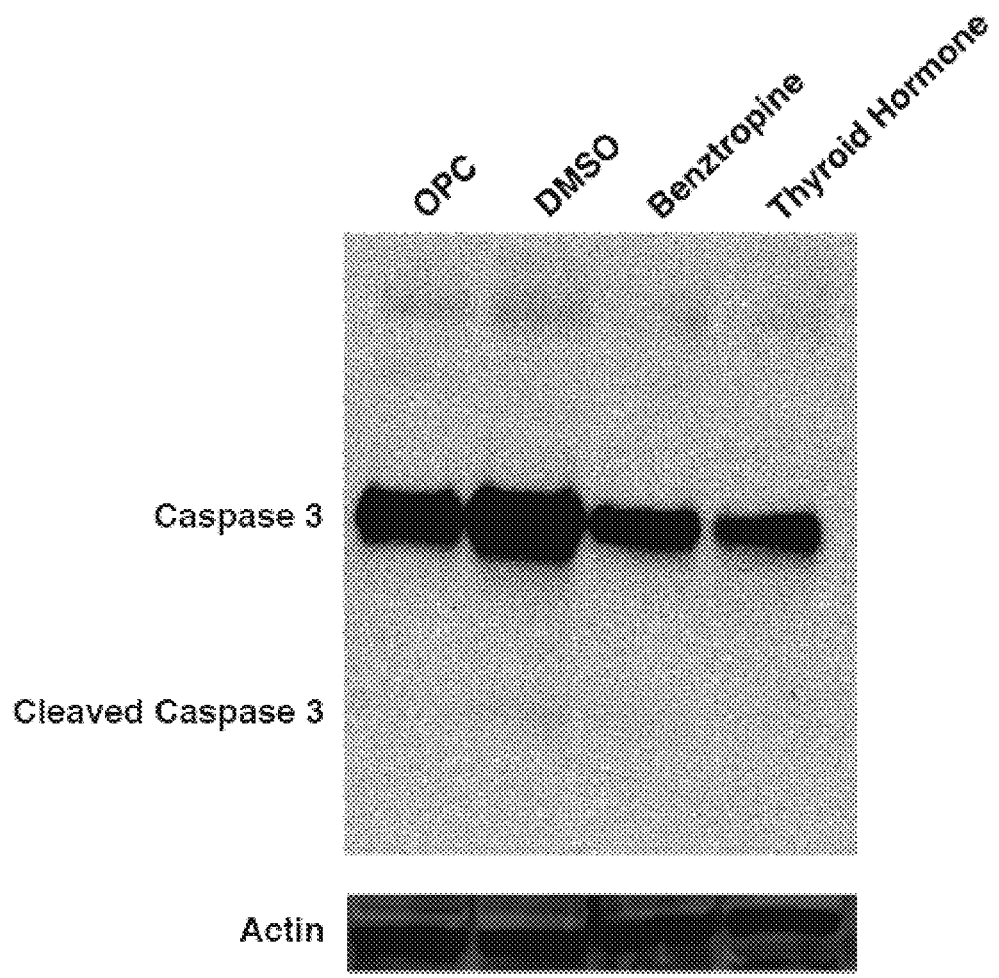
FIG. 32. Western blot analysis of cleaved caspase activity in differentiated OPCs. OPCs were plated in basal differentiation media and treated with benztropine [1.5 uM], thyroid hormone [1 uM] or DMSO [<0.1%] for 6 days. Total protein was isolated and analyzed by Western blot using a specific antibody for the expression of caspase 3 and cleaved caspase 3. No expression of cleaved caspase 3 was detected in the compound treated cells or in untreated OPCs.

We further evaluated the ability of benztropine to induce OPC differentiation and enhance remyelination in vivo using the T-cell independent cuprizone-induced model of demyelination. In this model, mice are fed the copper chelatorbis(cyclohexylidenehydrazide) (cuprizone), which results in oxidative/nitrative stress that causes mitochondrial dysfunction and leads to CNS demyelination (P. Mana et al., *Am J Pathol*, 168, 1464 (2006); M. Lindner et al., *Glia*, 56, 1104 (2008); P. Mana et al., *J Neuroimmunol*, 210, 13 (2009); L. Liu et al., *Nat Neurosci*, 13, 319 (2010); A. J. Steelman, J. P. Thompson, J. Li, *Neurosci Res*, 72, 32 (2012)). The demyelinated lesions observed in this model are reminiscent of pattern III MS lesions and involve minimal contribution from hematogenous immune cells (L. Liu et al., *Nat Neurosci*, 13, 319 (2010); C. Lucchinetti et al., *Ann Neurol* 47, 707 (2000); L. T. Remington et al., *Am J Pathol*, 170, 1713 (2007)). Inclusion of 0.2% (w/v) cuprizone in the diet of C57BL/6 mice induces a demyelination program that proceeds with a defined series of events over a characteristic time course, wherein the corpus callosum shows peak demyelination following 6-7 weeks of feeding (T. Skripuletz et al., *Am J Pathol*, 172, 1053 (2008)). Spontaneous remyelination is observed 2-4 weeks following cuprizone withdrawal (T. Skripuletz et al., *Am J Pathol*, 172, 1053 (2008)). By administering drugs at the time when a cuprizone-free diet is reintroduced, the efficacy of promyelinating agents can be examined by evaluating the relative kinetics of OPC dependent remyelination (T. Skripuletz et al., *Am J Pathol*, 172, 1053 (2008)). Following 7 weeks of exposure, upon withdrawal of cuprizone, we administered benztropine (10 mg/kg) intraperitoneally to 15 week old C57BL/6 mice. Drug or vehicle treated mice were sacrificed in groups of 5 weekly for 5 weeks, following drug treatment, and remyelination was quantitatively evaluated by staining the corpus callosum regions of harvested brains with LFB (FIG. 9A, B). Significant demyelination was clearly observed following seven weeks of treatment with cuprizone, as compared to control animals. Consistent with an enhancement of OPC differentiation and accelerated remyelination, a significant increase in myelin staining in the corpus callosum was observed at week 2 following treatment with benztropine, as compared to the spontaneous remyelination observed in vehicle controls (FIG. 9A, B). As expected, at later time points spontaneous remyelination was relatively complete and significant differences were not observed between drug and vehicle treated animals. A lack of difference at these later time points indicates that, even following 5 weeks of treatment at efficacious doses, benztropine is not toxic to mature oligodendrocytes. These data again suggest that benztropine enhances the process of in vivo remyelination, by directly inducing OPC differentiation. Benztropine could also enhance remyelination by exerting a protective effect on a "pre-oligodendrocyte" intermediate cell type or by a process involving a combination of both effects. Caspase-3 activation results from both intrinsic and extrinsic apoptotic pathways and serves as a general indicator of stress induced cell death. Benztropine treatment was not found inhibit caspase-3 activation on days 2, 4, and 6 of differentiation, as determined by western blot and immunofluorescence analysis (FIG. 32). However, cleaved caspase-3 was barely detectable in OPCs at any time point in DMSO treated controls, indicating that failed OPC differentiation does not likely result from stress induced cell death.

For the treatment of MS, an OPC differentiation inducing drug would most likely be introduced clinically as part of a combination therapy with an immunosuppressive drug. Using the PLP induced EAE model, we therefore evaluated the clinical efficacy of benztropine when combined with either of two immunomodulating drugs approved for the treatment of MS, interferon-$\beta$ and FTY720 (L. Kappos et al., *N Engl J Med*, 355, 1124 (2006); M. Fujino et al., *J Pharmacol Exp Ther*, 305, 70 (2003); L. Jacobs et al., *Arch Neurol*, 39, 609 (1982); M. Huber et al., *J Neurol*, 235, 171 (1988)). The former reduces T-cell proliferation and alters cytokine expression (A. Noronha, A. Toscas, M. A. Jensen, *J Neuroimmunol*, 46, 145 (1993); A. Noronha, A. Toscas, M. A. Jensen, *Ann Neurol*, 27, 207 (1990)), while the latter is an S1P agonist that regulates T-cell trafficking (V. Brinkmann et al., *J Biol Chem*, 277, 21453 (2002); V. Brinkmann et al., *Nat Rev Drug Discov*, 9, 883 (2010)). We determined whether the combination of an OPC inducing drug with either interferon-$\beta$ or FTY720 would improve efficacy and/or decrease the dose of the immunosuppressive agent required to achieve maximal benefit. Initially, all three drugs were dosed individually over a range of concentrations, to determine suboptimal and maximal effective/tolerated doses of each in the models (FIGS. 25 and 33 A,B). Benztropine was then administered with either of two existing immune modulating treatments for MS, and as described below, these combinations resulted in significant benefits in the EAE model. Addition of 2.5 mg/kg benztropine to 1 mg/kg FTY720 (FIG. 10A) or 10,000 U/mouse interferon-$\beta$ (FIG. 10B) resulted in a significant decrease in observed clinical severity, as compared to that observed when either FTY720 or interferon-$\beta$ was dosed alone. Further, the combination of 2.5 mg/kg benztropine with a suboptimal dose of FTY720 (0.1 mg/kg) resulted in a significant decrease in clinical severity that was greater than that observed when either drug was dosed alone and was comparable to the clinical efficacy observed when FTY720 was dosed alone at near the maximal observed tolerated dose of 1 mg/kg (FIG. 10C). This observation may prove clinically relevant as FTY720 treatment is associated with bradycardia which is dose dependent.

We have identified a centrally acting FDA approved drug that, when dosed alone in the most clinically relevant model of MS, significantly decreases disease severity. Benztropine enhances remyelination, leading to functional recovery, by directly stimulating the differentiation of OPCs by a mechanism involving antagonism of $M_1/M_3$ muscarinic receptors expressed on immature OPCs. Evidence that this drug functions by directly stimulating remyelination, and not by inhibiting demyelination, is provided by the observed lack of effect of benztropine on in vitro and in vivo T-cell biology and by the observed promyelinating activity of benzotropine in the T-cell independent cuprizone-induced model of demyelination. Inclusion of benztropine in treatment regimens involving existing approved immunomodulatory drugs resulted in enhanced functional recovery and significantly decreases the dosages of the latter that are required to achieve an equivalent level of efficacy. To our knowledge, these results provide the first in vivo evidence supporting the notion that a benefit can be achieved by treating MS-like symptoms using the combination of an immunomodulator with a remyelination enhancer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising:
    a neurotransmitter receptor modulating agent, wherein the neurotransmitter receptor modulating agent is a muscarinic receptor antagonist and wherein the muscarinic receptor antagonist is benztropine, clemastine, or a salt thereof; and
    an immunomodulatory agent useful for treating multiple sclerosis, wherein the immunomodulatory agent is a sphingosine 1-phosphate (S1P) agonist and wherein the S1P agonist is fingolimod (FTY720) or a salt thereof,
    wherein the neurotransmitter receptor modulating agent and the immunomodulatory agent are formulated in a single pharmaceutical composition and wherein the immunomodulatory agent is formulated as a subtherapeutic dose.

2. The composition of claim 1, wherein the muscarinic receptor antagonist is benztropine or a salt thereof.

3. The composition of claim 1, wherein the composition is formulated for systemic administration.

4. The composition of claim 1, wherein the composition is formulated for oral administration.

5. The composition of claim 1, wherein the muscarinic receptor antagonist is clemastine or a salt thereof.

6. A kit comprising:
    a neurotransmitter receptor modulating agent that is a muscarinic receptor antagonist, wherein the muscarinic receptor antagonist is benztropine, clemastine, or a salt thereof; and
    an immunomodulatory agent useful for treating multiple sclerosis, wherein the immunomodulatory agent is a S1P agonist, and wherein the S1P agonist is fingolimod (FTY720) or a salt thereof;
    wherein the immunomodulatory agent is formulated as a subtherapeutic dose.

7. The kit of claim 6, wherein the neurotransmitter receptor modulating agent and the immunomodulatory agent are formulated in a single pharmaceutical composition.

8. The kit of claim 6, wherein the muscarinic receptor antagonist is benztropine or a salt thereof.

9. The kit of claim 6, wherein the muscarinic receptor antagonist is clemastine or a salt thereof.

* * * * *